US012590094B2

(12) United States Patent
Lasmézas et al.

(10) Patent No.: US 12,590,094 B2
(45) Date of Patent: Mar. 31, 2026

(54) COMPOUNDS FOR THE TREATMENT OF NEURODEGENERATIVE AND METABOLIC DISORDERS

(71) Applicant: UNIVERSITY OF FLORIDA RESEARCH FOUNDATION, INCORPORATED, Gainesville, FL (US)

(72) Inventors: Corinne Lasmézas, Palm Beach Gardens, CA (US); Minghai Zhou, Jupiter, FL (US); Thomas D. Bannister, Palm Beach Gardens, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1000 days.

(21) Appl. No.: 17/610,758

(22) PCT Filed: May 14, 2020

(86) PCT No.: PCT/US2020/032903
§ 371 (c)(1),
(2) Date: Nov. 12, 2021

(87) PCT Pub. No.: WO2020/232255
PCT Pub. Date: Nov. 19, 2020

(65) Prior Publication Data

US 2023/0041523 A1 Feb. 9, 2023

Related U.S. Application Data

(60) Provisional application No. 62/847,600, filed on May 14, 2019.

(51) Int. Cl.

| | |
|---|---|
| ***C07D 487/04*** | (2006.01) |
| ***A61K 31/352*** | (2006.01) |
| ***C07D 217/04*** | (2006.01) |
| ***C07D 217/10*** | (2006.01) |
| ***C07D 277/42*** | (2006.01) |
| ***C07D 311/30*** | (2006.01) |
| ***C07D 401/06*** | (2006.01) |
| ***C07D 401/14*** | (2006.01) |
| ***C07D 405/14*** | (2006.01) |
| ***C07D 413/14*** | (2006.01) |
| ***C07D 417/04*** | (2006.01) |
| ***C07D 471/04*** | (2006.01) |
| ***C07D 513/04*** | (2006.01) |
| ***C07H 17/07*** | (2006.01) |

(52) U.S. Cl.
CPC .......... *C07D 487/04* (2013.01); *A61K 31/352* (2013.01); *C07D 217/04* (2013.01); *C07D 217/10* (2013.01); *C07D 277/42* (2013.01); *C07D 311/30* (2013.01); *C07D 401/06* (2013.01); *C07D 401/14* (2013.01); *C07D 405/14* (2013.01); *C07D 413/14* (2013.01); *C07D 417/04* (2013.01); *C07D 471/04* (2013.01); *C07D 513/04* (2013.01); *C07H 17/07* (2013.01)

(58) Field of Classification Search
CPC .. C07D 487/04; C07D 217/04; C07D 217/10; C07D 277/42; C07D 311/30; C07D 401/16; C07D 401/14; C07D 405/14; C07D 413/14; C07D 417/04; C07D 471/04; C07D 513/04; C07H 17/07
USPC .......................................................... 514/157
See application file for complete search history.

(56) References Cited

FOREIGN PATENT DOCUMENTS

| | | | |
|---|---|---|---|
| WO | 2006003147 | A1 | 1/2006 |
| WO | 2017015660 | A1 | 1/2017 |
| WO | 2017160864 | A1 | 9/2017 |

OTHER PUBLICATIONS

Lundin et al.. "Two novel fusion inhibitors of human respiratory syncytial virus", Antiviral Res. Dec. 2010;88(3):317-24. doi: 10.1016/j.antiviral.2010.10.004. Epub Oct. 19, 2010.
International Search Report of PCT/US2020/032903, 2020.
Written Opinion of PCT/US2020/032903, 2020.

*Primary Examiner* — Kristin A Vajda
(74) *Attorney, Agent, or Firm* — Gregory Finch; Finch Paolino, LLC

(57) ABSTRACT

Compounds described herein may be used for the treatment of neurodegenerative diseases linked to protein misfolding, including prion diseases, Alzheimer's disease, Parkinson's disease (PD) and amyotrophic lateral sclerosis (ALS), and also other neurodegenerative, degenerative, metabolic and ischemic conditions. Indeed, NAD metabolism impairment is also a critical feature in brain ischemia/reperfusion injury, Wallerian degeneration, kidney failure, multiple sclerosis, aging, and metabolic disorders such as diabetes mellitus. Therapies that elevate or stabilize NAD levels may thus have broad potential for treating many severely debilitating neurological and metabolic conditions. Evidence is provided herein with compounds from 8 lead series for NAD restoring properties and for therapeutic efficacy in cellular and/or animal models of prion disease, PD and ALS.

5 Claims, 16 Drawing Sheets

Figure 2A
carbazoles (e.g., DMCM)
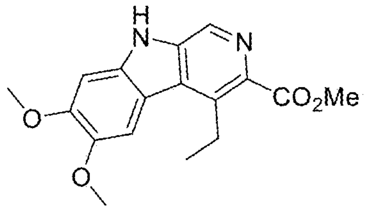
SR1-75869
Mol Wt. = 314
cLogP = 2.2
HBD = 1
HBA = 4
tPSA = 69
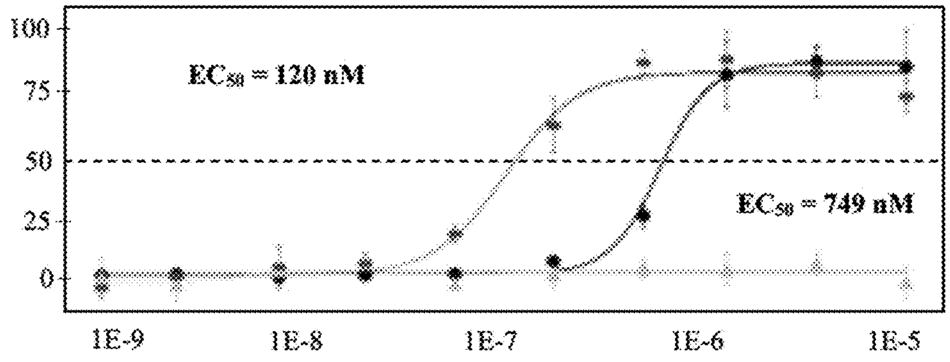
Figure 2B
pyrazolopyrimidines
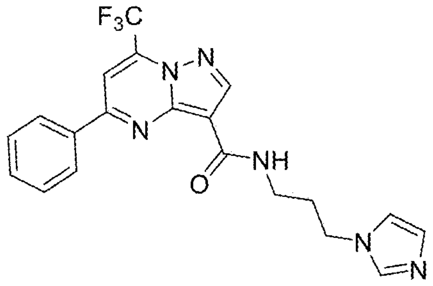
SR1-293229
Mol Wt. = 414
cLogP = 3.0
HBD = 1
HBA = 4
tPSA = 73
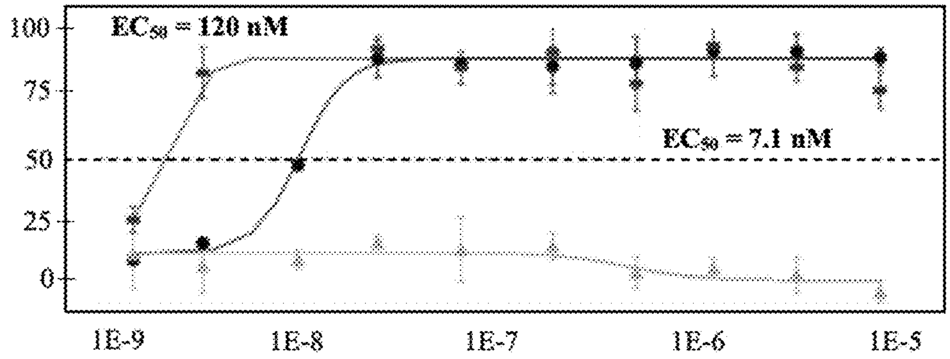

Figure 2C
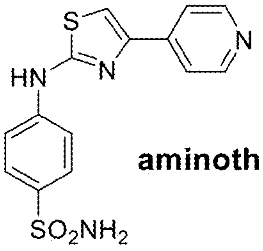
aminothiazoles
SR1-477186
Mol Wt. = 332
cLogP = 2.7
HBD = 3
HBA = 4
tPSA = 97
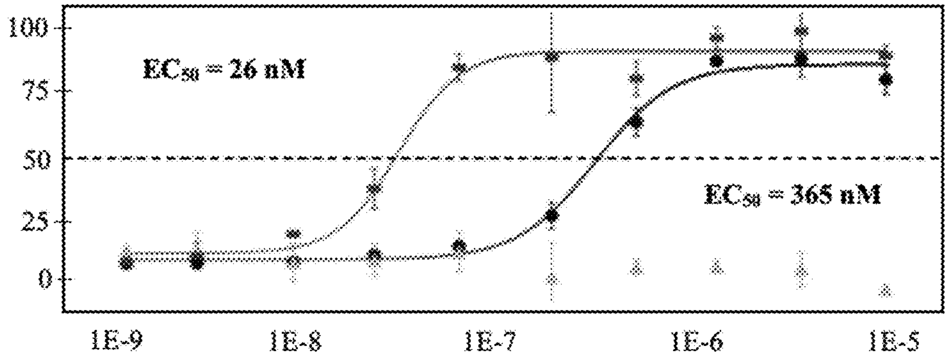
Figure 2D
triazolophthalazines
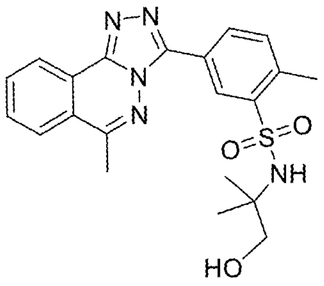
SR1-115259
Mol Wt. = 426
cLogP = 2.9
HBD = 2
HBA = 6
tPSA = 107
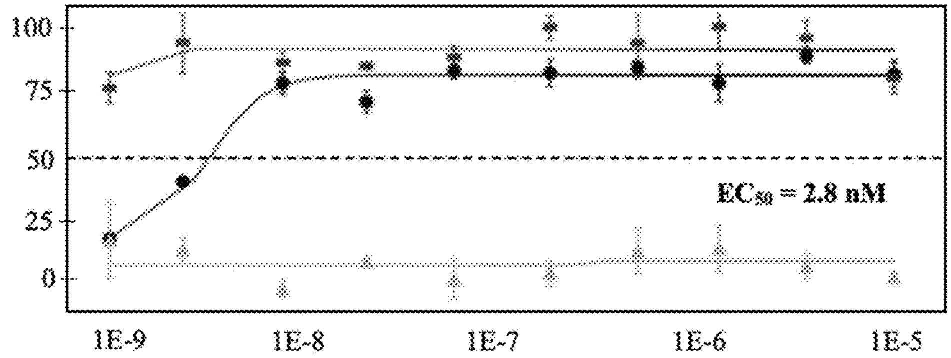

Figure 2E
aminophthalazines (e.g., vatalanib)
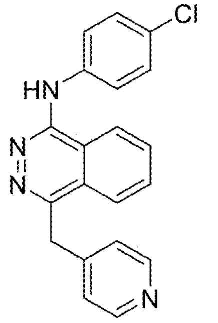
SR5-1457
aka vatalanib
Mol Wt. = 347
cLogP = 4.7
HBD = 1
HBA = 3
tPSA = 49
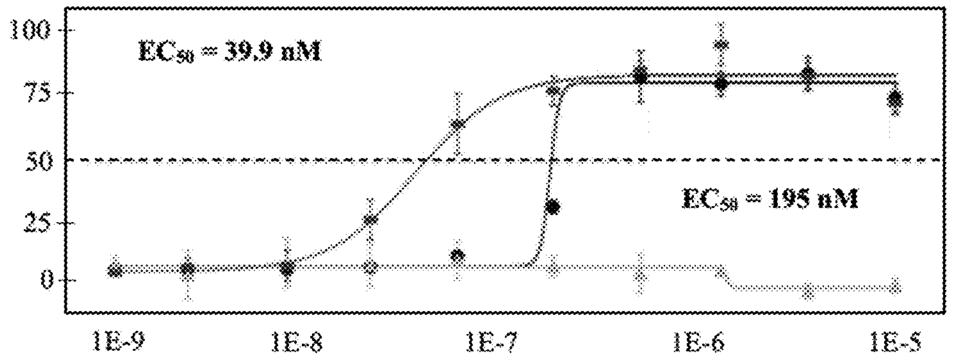
Figure 2F
flavonoids
(e.g., nobiletin)
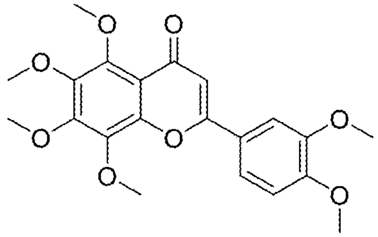
SR1-712262
aka nobiletin
Mol Wt. = 402
cLogP = 2.1
HBD = 0
HBA = 8
tPSA = 82
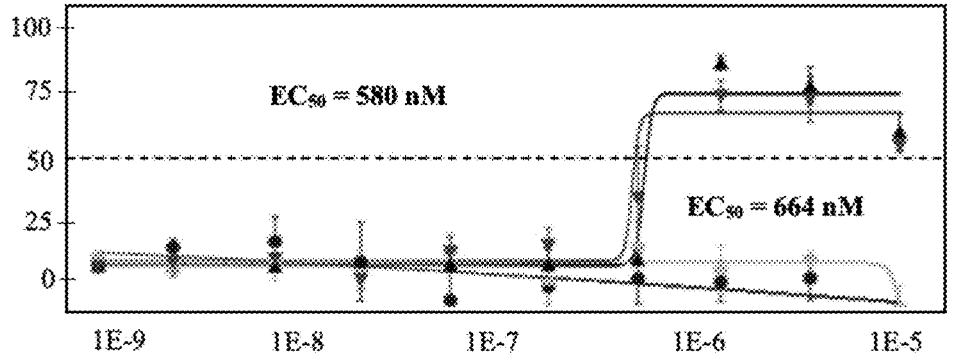

Figure 2G
Alkaloids (e.g., palmatine chloride)
SR1-841226
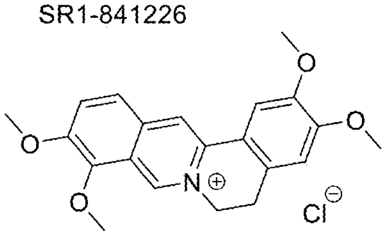
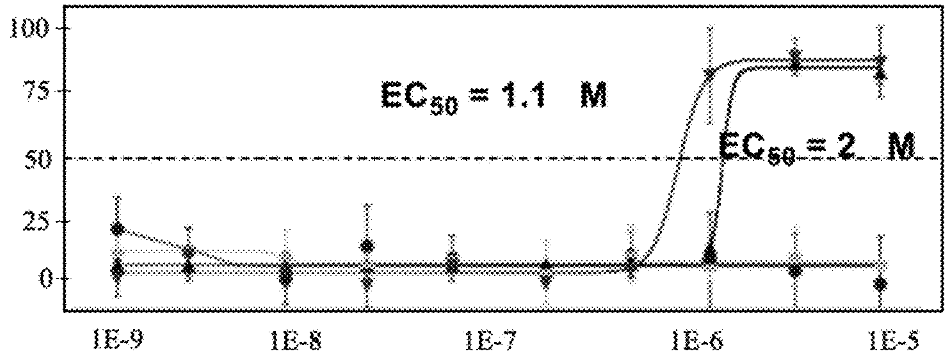
Figure 2H
3-heteroaryl quinolines
(e.g. DMPQ)
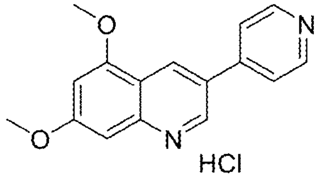
SR1-597957
aka DMPQ HCl
Mol Wt. = 266 (free base)
cLogP = 3.1
HBD = 0
HBA = 4
tPSA = 43
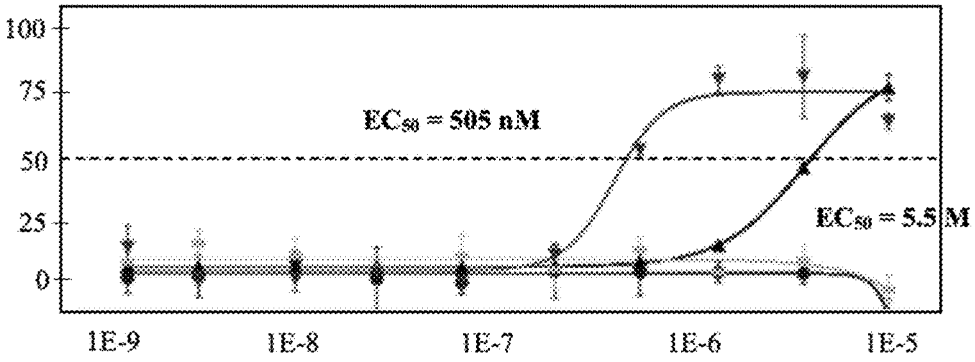

Figure 10
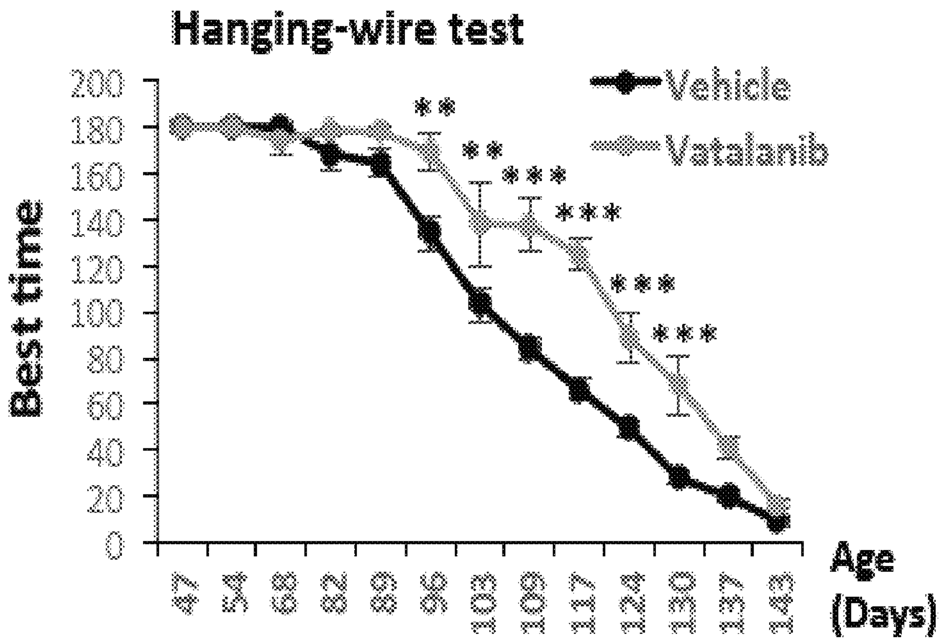
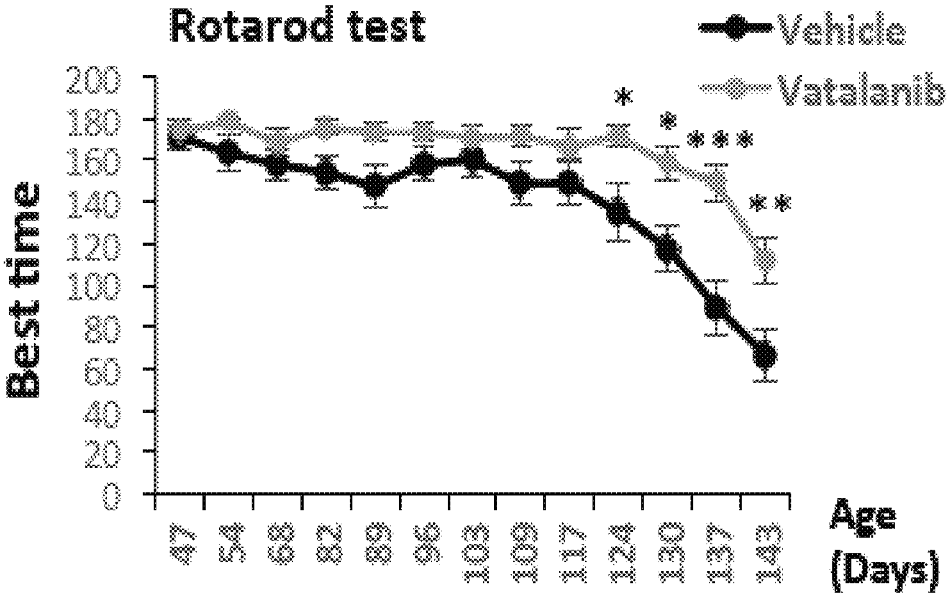

Figure 11

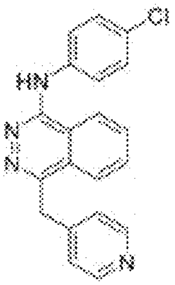

CGP 79787 / vatalanib
VEGF-R activity:
$IC_{50}$ = 77 nM (Flt-1), 37 nM (KDR)

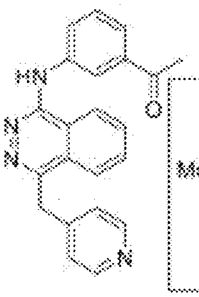

properties
Mol. Weight: 354
cLogP: 3.6
HBD: 1
HBA: 4
tPSA: 68 example 70A in WO9835958A1
VEGF-R activity
$IC_{50}$ = 1.0 μM (Flt-1)

SR5-1457
neuroprotective activity $IC_{50}$ = 39.9 nM
NAD restoration $IC_{50}$ = 195 nM

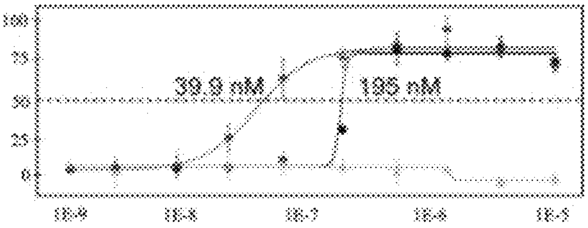

SR1-134005
neuroprotective activity $IC_{50}$ = 6.3 nM
NAD restoration $IC_{50}$ = 105 nM

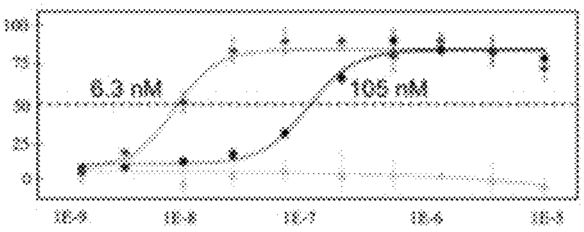

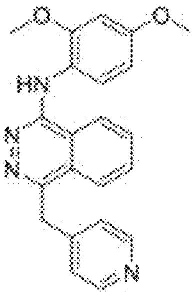

example 67T in WO9835958A1
VEGF-R activity
$IC_{50}$ >1 μM (Flt-1)

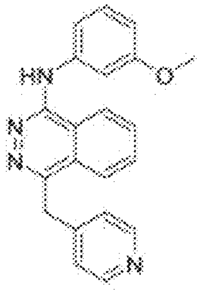

example 32F in WO9835958A1
VEGF-R activity
$IC_{50}$ = 793 nM (Flt-1)

SR1-151915
neuroprotective activity $IC_{50}$ = 71.4 nM
NAD restoration $IC_{50}$ = 280 nM

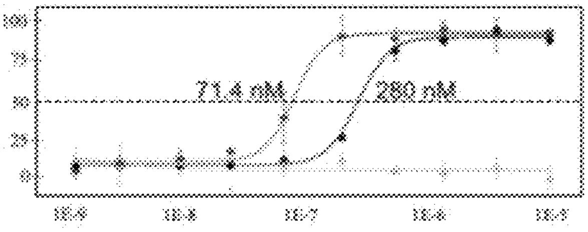

SR1-151911
neuroprotective activity
44% @ 6.4 μM

Figure 16

NAMPT activation assay – multiple leads

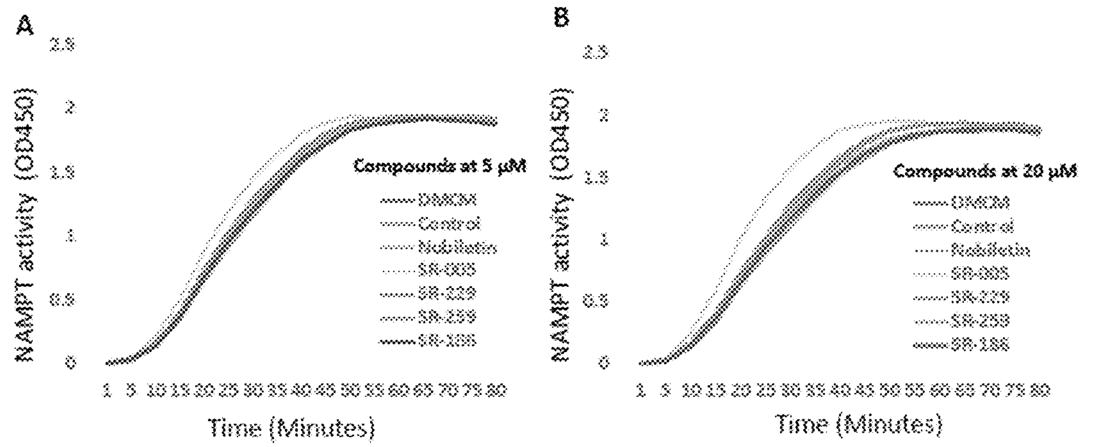

NAMPT activation assay – SR-005 dose response

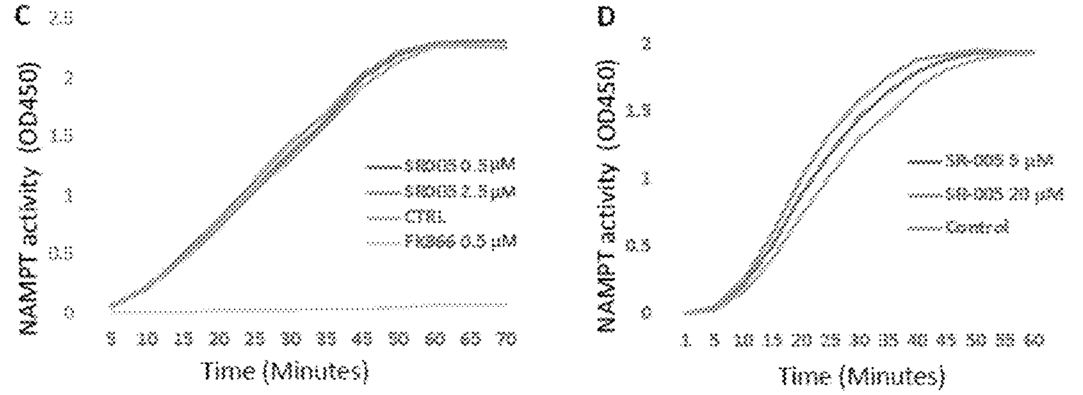

| Compound | Activity rate (A25-A10) / (T25-10) | Activity increase (percentage from control) |
|---|---|---|
| SR-005 0.5 µM | 0.050323 | 2.4 % |
| SR-005 2.5 µM | 0.059493 | 7.8 % |
| Control | 0.049124 | |

| Compound | Activity rate (A25-A10) / (T25-10) | Activity increase (percentage from control) |
|---|---|---|
| SR-005 5 µM | 0.065322 | 13.8 % |
| SR-005 20 µM | 0.072219 | 25.8 % |
| Control | 0.057419 | |

NAMPT activation assay – vatalanib

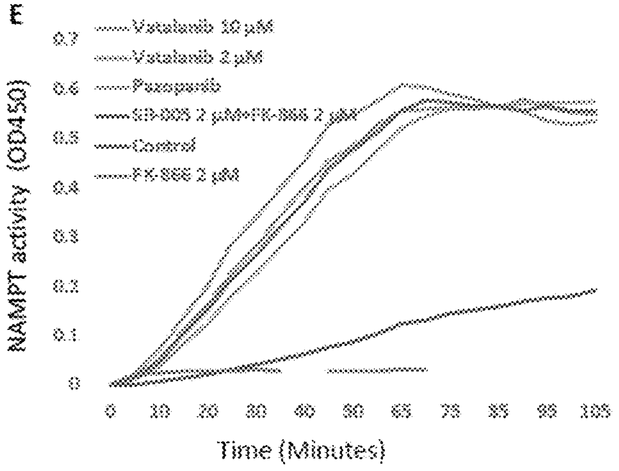

| Compound | Activity rate (A30-A10) / (T30-10) | Activity increase (percentage from control) |
|---|---|---|
| Vatalanib 10 µM | 0.01354 | 24.2 % |
| Vatalanib 2 µM | 0.01139 | 4.5% |
| Control | 0.0109 | |

COMPOUNDS FOR THE TREATMENT OF NEURODEGENERATIVE AND METABOLIC DISORDERS

CROSS-REFERENCES TO RELATED APPLICATIONS

This application is a U.S. National Stage Entry of the International Patent Application No. PCT/US2020/032903 filed on May 14, 2020, which claims the benefit of priority of U.S. Provisional Application No. 62/847,600 filed on May 14, 2019, which are incorporated herein in their entireties and for all purposes.

STATEMENT OF GOVERNMENT SUPPORT

This invention was made with government support under grant numbers 5R01NS085223 and R21NS093488 awarded by the National Institutes of Health. The government has certain rights in the invention.

BACKGROUND

A number of fatal neurodegenerative diseases, including prion diseases such as Creutzfeldt-Jakob disease (CJD), Alzheimer's (AD), Parkinson's (PD), frontotemporal dementia (FTD) and amyotrophic lateral sclerosis (ALS), are characterized by toxicity resulting from protein misfolding, and are called protein misfolding neurodegenerative diseases (PMNDs). Proteins involved in these diseases misfold and form aggregates of various sizes. Some of these aggregates are highly toxic for neurons, a phenomenon also referred to as proteotoxicity. Protein aggregates can also exhibit "prion-like" properties, in the sense that they propagate from cell to cell and act as seeds to amplify the misfolding and aggregation process within a cell. Such toxic misfolded proteins include the prion protein PrP in CJD, Aβ and tau in AD; α-synuclein and tau in PD; tau, TDP-43 and C9ORF72 in FTD; SOD1, TDP43, FUS and C9ORF72 in ALS. PD belongs to a broader group of diseases called synucleinopathies, characterized by the accumulation of misfolded α-synuclein aggregates. Lewy body dementia is also a synucleinopathy. FTD belongs to another group of PMNDs termed tauopathies, a group that also includes chronic traumatic encephalopathy (CTE) and progressive supranuclear palsy (PSP). There are also non-neurological diseases involving protein misfolding, such as diabetes mellitus where the proteins IAPP and proinsulin form protein aggregates that are toxic for pancreatic beta-cells.

Poor knowledge of the mechanisms of neurotoxicity has hampered the development of effective therapies for PMNDs. To study such mechanisms, a model that uses misfolded and toxic prion protein (TPrP) has been developed, and in particular TPrP reproducibly induces neuronal death in cell culture and after intracerebral injection[1]. TPrP induces death of more than 60% of cultured neurons at nanomolar concentration, whereas the natively folded counterpart of the prion protein, NTPrP, does not. Therefore, this model provides a highly efficient system to study mechanisms of neuronal death that follow exposure to a misfolded protein. Certain mechanisms for prion-induced toxicity, and the knowledge of how to thwart them, were thought to be more broadly applicable to other PMNDs. Thus, as demonstrated herein, TPrP-based studies spurred the development of new neuroprotective approaches for treating devastating PMNDs.

SUMMARY

There are no disease-modifying treatments currently available for any protein misfolding neurodegenerative disease (PMND). Current treatments, when they exist at all, alleviate certain disease symptoms but neither slow down the progression of the underlying pathogenic mechanisms nor halt neuronal loss. The compounds described herein, in contrast, are capable of interfering with fundamental mechanisms of neurotoxicity linked to alterations in NAD metabolism, thereby sparing neurons from further injury. The approach described herein may therefore provide first-in-kind disease-modifying treatments for PMNDs and other diseases associated with an impairment of NAD metabolism.

Provided is, in various embodiments, a method for inhibiting NAD consumption and/or increasing NAD synthesis in a patient, comprising administering to the patient an effective amount of a compound comprising any of the species, or a member of any of the genera, of chemical structures disclosed and claimed herein for the purpose.

Provided is, in various embodiments, a method for preventing or inhibiting NAD depletion in a patient, or a method for improving a condition linked to alterations of NAD metabolism in a patient, comprising administering to the patient an effective amount of a compound comprising any of the species, or a member of any of the genera, of chemical structures disclosed and claimed herein for the purpose. The condition can comprise a metabolic disorder, diabetes, aging, a neurodegenerative disease, neuronal degeneration associated with multiple sclerosis, hearing loss or retinal damage, brain or cardiac ischemia, kidney failure, traumatic brain injury, or an axonopathy.

Provided is, in various embodiments, a method for providing protection from toxicity of misfolded proteins in a patient, comprising administering to the patient an effective amount of a compound comprising any of the species, or a member of any of the genera, of chemical structures disclosed and claimed herein for the purpose.

Provided is, in various embodiments, a method for preventing or treating a protein misfolding neurodegenerative disease in a patient, comprising administering to the patient an effective amount of a compound comprising any of the species, or a member of any of the genera, of chemical structures disclosed and claimed herein for the purpose. The disease can be a prion disease such as Creutzfeldt-Jakob disease (CJD), Parkinson's disease (PD) or other synucleinopathies, Alzheimer's disease (AD), amyotrophic lateral sclerosis (ALS), or tauopathies such as frontotemporal dementia (FTD), chronic traumatic encephalopathy (CTE), and progressive supranuclear palsy (PSP).

Further provided are novel compounds that may be useful for the methods described herein.

Provided is, in various embodiments, a compound having a Formula (I), (I)

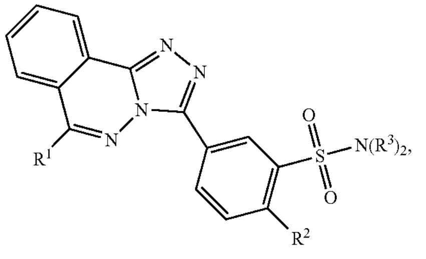

or a pharmaceutically acceptable salt thereof.

In Formula (I):

Each $R^1$ and $R^2$ are independently H, $(C_1\text{-}C_4)$alkyl, or $(C_1\text{-}C_4)$alkoxy; and Each $R^3$ is independently selected H, $(C_1\text{-}C_4)$alkyl optionally substituted with OH, $(C_1\text{-}C_4)$alkoxy, or heteroaryl, and provided that both $R^3$ are not H; or, both $R^3$ together with the nitrogen atom to which they are bonded form a 5- to 7-membered heterocyclyl ring comprising at least on additional heteroatom selected from O, S, S═O, S(═O)═O, or NR, wherein R is $(C_1\text{-}C_4)$alkyl optionally substituted with —OH or $(C_1\text{-}C_4)$alkoxyl.

Provided is, in various embodiments, a compound having a Formula (II).

(II)

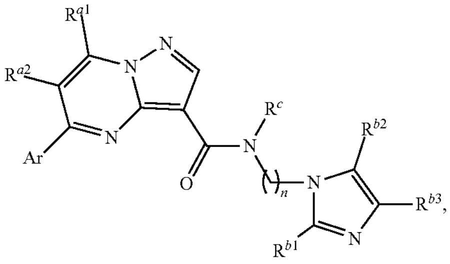

or a pharmaceutically acceptable salt thereof.

In Formula (II):

Each $R^{a1}$ and $R^{a2}$ is independently hydrogen, $(C_1\text{-}C_4)$alkyl, $(C_1\text{-}C_4)$haloalkyl, $(C_1\text{-}C_4)$alkoxyl, $(C_1\text{-}C_4)$haloalkoxyl, 2 to 4 membered heteroalkyl, cycloalkyl, heterocycloalkyl, aryl, or heteroaryl;

Each $R^{b1}$, $R^{b2}$, and $R^{b3}$ is independently hydrogen, halo, $(C_1\text{-}C_4)$alkyl, $—S(O)_2R^d$, $—S(O)_2OR^d$, or $(C_1\text{-}C_4)$haloalkyl; or $R^{b2}$ and $R^{b3}$ are joined together to form an aryl or heteroaryl;

Each $R^c$ and $R^d$ is independently hydrogen or $(C_1\text{-}C_4)$alkyl;

Ar is mono- or bi-cyclic aryl or heteroaryl, optionally substituted with one or more halo, $(C_1\text{-}C_4)$alkyl, $(C_1\text{-}C_4)$haloalkyl, $(C_1\text{-}C_4)$alkoxyl, $(C_1\text{-}C_4)$haloalkoxyl, or heteroaryl; and n=2, 3, 4, or 5.

Provided is, in various embodiments, a compound having a Formula (III), (III)

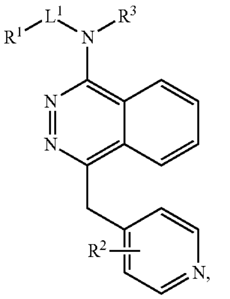

or a pharmaceutically acceptable salt thereof.

In Formula (III):

$L^1$ is a bond, $C_1\text{-}C_4$ alkylene, or 2 to 4-membered heteroalkylene;

$R^1$ is mono- or bi-cyclic cycloalkyl, heterocycloalkyl, aryl, alkylaryl, or heteroaryl, wherein the cycloalkyl, heterocycloalkyl, aryl, alkylaryl or heteroaryl is optionally substituted with one or more selected from halo, $(C_1\text{-}C_4)$alkyl, hydroxy$(C_1\text{-}C_4)$alkyl, $(C_1\text{-}C_4)$alkoxyl, $—C(═O)(C_1\text{-}C_4)$alkyl, $—C(═O)N(R)_2$, or $—C(═NR)(C_1\text{-}C_4)$alkyl, wherein the $(C_1\text{-}C_4)$alkyl is unsubstituted or substituted with heterocycloalkyl;

Each R is independently H, —OH, $(C_1\text{-}C_4)$alkyl, or $(C_1\text{-}C_4)$alkoxyl, or two R together with the nitrogen atom to which it is bonded form a heterocycloalkyl, optionally further comprising an O atom in the heterocyclyl ring;

$R^2$ occurs 0, 1, or 2 times, and is $(C_1\text{-}C_4)$alkyl, $(C_1\text{-}C_4)$haloalkyl, or $SO_2N(R^4)_2$; and each $R^3$ and $R^4$ is independently H, or $(C_1\text{-}C_4)$alkyl.

Provided is, in various embodiments, a compound having a Formula (IV).

(IV)

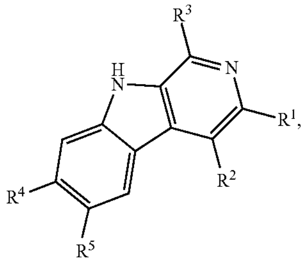

or a pharmaceutically acceptable salt thereof.

In Formula (IV):

$R^1$ is hydrogen, $(C_1\text{-}C_4)$alkyl, —C(O)OH, $—C(O)O—(C_1\text{-}C_4)$alkyl, $—C(O)NHNHR^6$, $—C(O)NR^6—((C_1\text{-}C_4)$alkylene)-$NHR^6$, $—C(O)NR^6(C_1\text{-}C_4)$alkyl, or $—C(O)NR^6$-cycloalkylene-$NHR^6$;

$R^3$ is hydrogen or $(C_1\text{-}C_4)$alkyl;

Each $R^2$, $R^4$, $R^5$ is independently hydrogen, halo, $(C_1\text{-}C_4)$alkyl, $—C(O)O—(C_1\text{-}C_4)$alkyl, $(C_1\text{-}C_4)$alkoxyl, $(C_1\text{-}C_4)$haloalkyl, or CN; and Each $R^6$ is hydrogen or $(C_1\text{-}C_4)$alkyl.

Provided is, in various embodiments, a compound having a Formula (V).

(V)

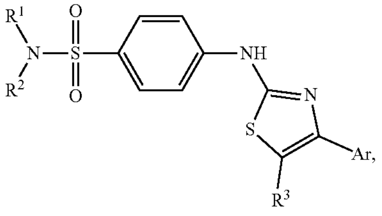

or a pharmaceutically acceptable salt thereof.

In Formula (V):

Ar is mono- or bi-cyclic aryl or heteroaryl, optionally substituted one or more with halo, $(C_1\text{-}C_4)$alkyl, $(C_1\text{-}C_4)$haloalkyl, CN, $—S(O)_2NH_2$, oxo, $—NH_2$, $(C_1\text{-}C_4)$alkoxyl, or $—NHC(O)(C_1\text{-}C_4)$alkyl;

Each $R^1$ and $R^2$ is independently hydrogen, $(C_1\text{-}C_4)$alkyl, aryl or heteroaryl, wherein the aryl or heteroaryl is optionally substituted with halo or ($C_1$-$C_4$)alkyl, or $R^1$ and $R^2$ attached to nitrogen join together to form a 5 to 6 membered heterocycloalkyl; and $R^3$ is hydrogen, or hydroxy-($C_1$-$C_4$)alkyl.

Other aspects of the inventions are disclosed infra.

BRIEF DESCRIPTION OF THE FIGURES

FIGS. 2A, 2B, 2C, 2D, 2E, 2F, 2G, 2H show structures and dose-response curves of 8 series of lead compounds (cell viability in the presence of TPrP, red; NAD quantification in the presence of TPrP, black; cell viability counter-screen in naïve cells, green; NAD quantification counter-screen in naïve cells, blue): FIG. 2A carbazoles; FIG. 2B pyrazolopyrimidines; FIG. 2C aminothiazoles; FIG. 2D triazolophthalazines; FIG. 2E aminophthalazines; FIG. 2F flavonoids (nobiletin); FIG. 2G alkaloids (palmatine); FIG. 2H 3-heteroarylquinolines (DMPQ).

The cell viability assay was performed in 1536-well plates. PK1 neuroblastoma cells (80 cells/well) were treated with 4 μg/ml TPrP for 3 days in 5 μl volume total. TPrP was prepared as described in Zhou, et. al., *Proc Natl Acad Sci USA* 109, 3113-3118 (2012)[1]. Compounds were added in 0.6% DMSO in a 30 nl volume in a 10-point, 4 logs titration at the doses indicated. Cell viability was measured using CellTiter-Glo® (Promega). NAD was quantified using NAD+/NADH-Glo™ (Promega).

Figure 3:
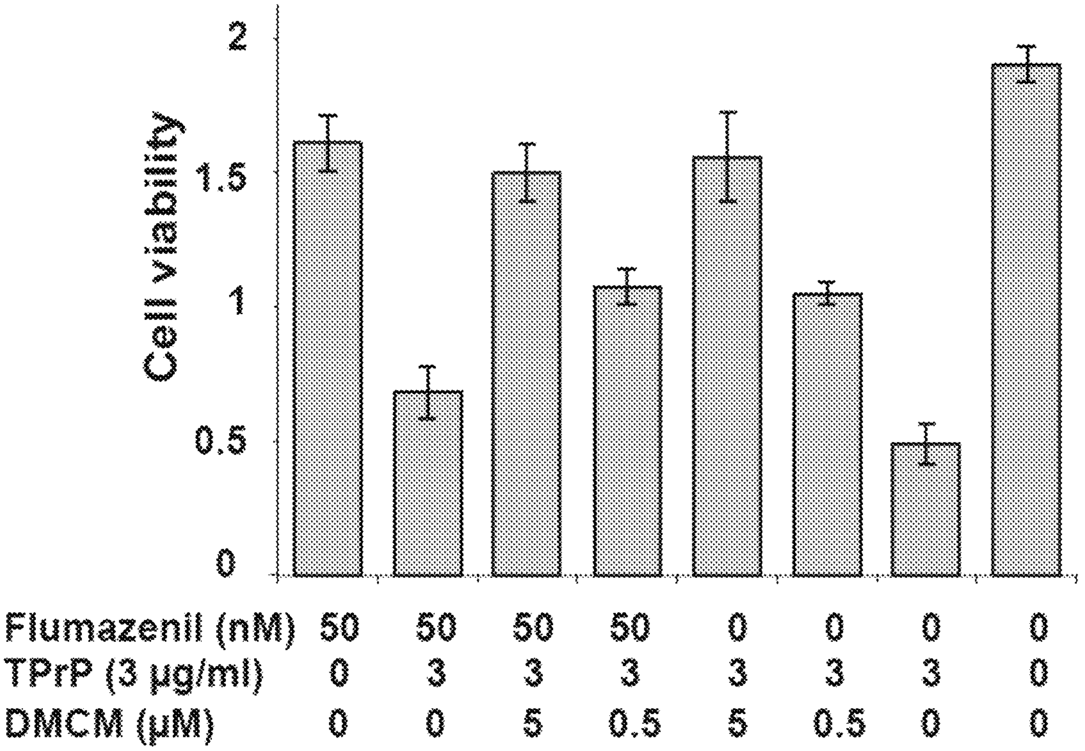

FIG. 3 shows the absence of neuroprotection by a $GABA_A$ R inhibitor structurally unrelated to DMCM. PK1 cells (1500 cells/well, 96-well plates) were treated with flumazenil (50 nM) for 24 h prior to exposure to TPrP (3 μg/ml) with or without DMCM (0.5 or 5 μM) for 4 days. TPrP was prepared as described in Zhou, et. al., *Proc Natl Acad Sci USA* 109, 3113-3118 (2012)[1]. Cell viability was measured using CellTiter-Glo® (Promega). The absence of protection of flumazenil against TPrP toxicity was repeated in a 10-point dose response experiment (0.3-164 nM, not shown). Flumazenil was used in this experiment at 100 times its $IC_{50}$ for $GABA_A$ R inhibition.

Figure 4:
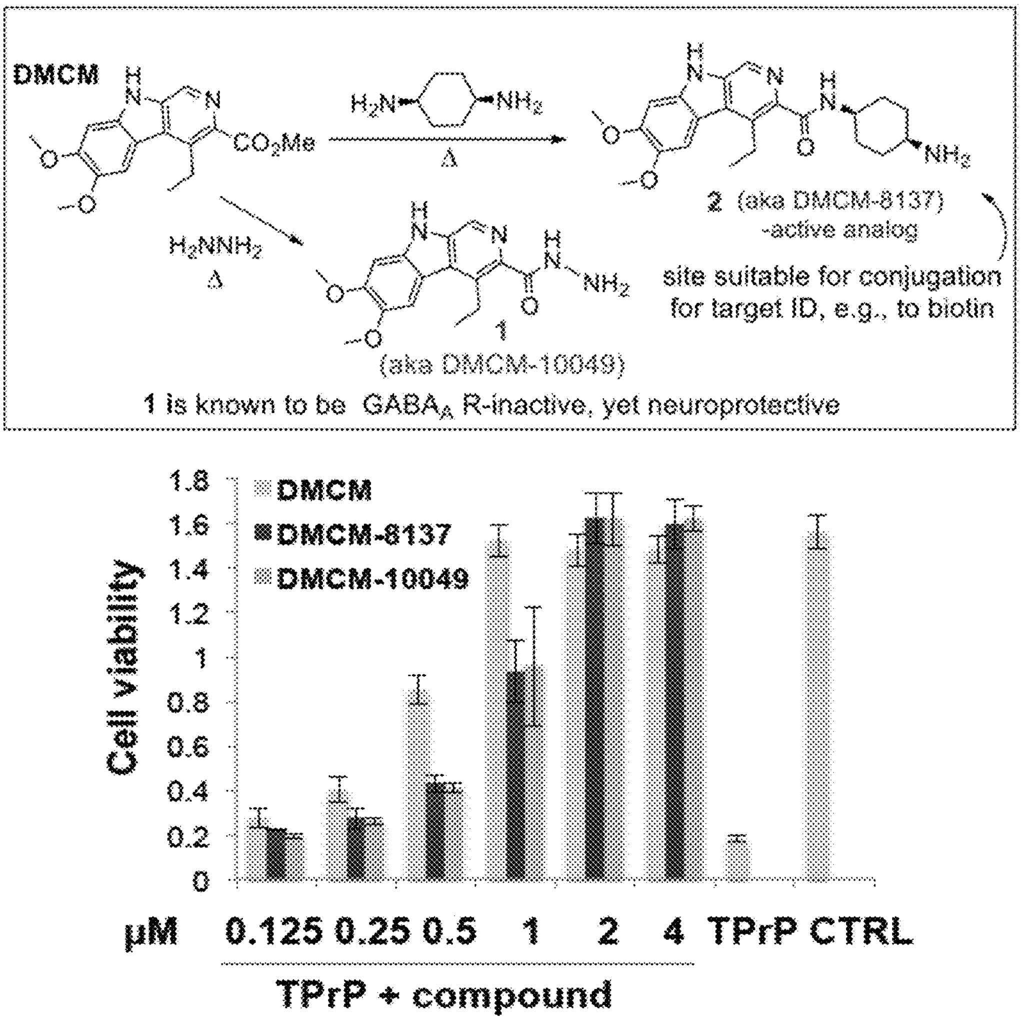

FIG. 4 shows that a $GABA_A$ R-inactive DMCM analog (DMCM-10049) and the aminoamide DMCM-8137 are neuroprotective. DMCM-8137 and DMCM-10049 show nearly identical dose-response profiles in the TPrP neuroprotection assay. Cells (1500 cells/well, 96-well plates) were exposed to TPrP at 5 μg/ml and to compounds at the doses indicated for 4 days. TPrP was prepared as described in Zhou, et. al., *Proc Natl Acad Sci US A* 109, 3113-3118 (2012)[1]. Cell viability was measured using CellTiter-Glo® (Promega).

Figure 5:
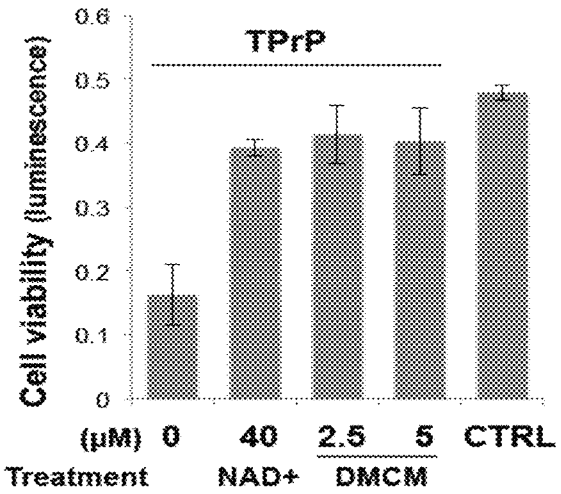

FIG. 5 shows that DMCM rescues TPrP-induced toxicity in primary neurons. Primary mouse cortical neurons (Life Technologies) were exposed to TPrP at 12 μg/ml for 5 days, and treated with DMCM or NAD where indicated. The assay was performed in the 96-well plate format. TPrP was prepared as described in Zhou, et. al., *Proc Natl Acad Sci USA* 109, 3113-3118 (2012)[1]. Shown is triplicate data±SDs. Cell viability was measured using CellTiter-Glo® (Promega). DMCM and NAD treatments also suppressed neuritic breakdown and neuronal vacuolation induced by TPrP exposure (not shown).

Figure 6:
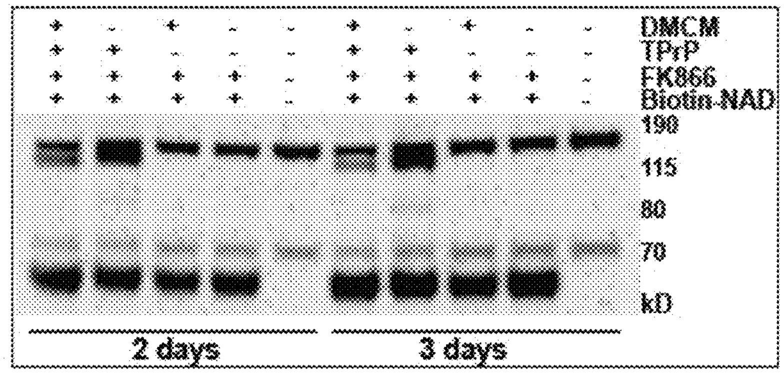

FIG. 6 shows that DMCM mitigates excessive protein ADP ribosylation induced by a misfolded protein. PK1 cells were treated with 5 μg/ml TPrP in the presence of 9 nM FK866 (to inhibit NAD synthesis from nicotinamide present in the medium) and 40 μM biotin-NAD (Trevigen). Cells were harvested after 2 or 3 days of treatment. Cell lysates were analyzed by SDS-PAGE, and ADP-ribosylated, biotinylated proteins were revealed using streptavidin-HRP. Bands corresponding to TPrP-specific ADP-ribosylation at ~80 and 130 kD are reduced in the presence of DMCM (compare lanes 1&2 of each time point). DMCM has no effect in the absence of TPrP (lanes 3&4 of each time point). 10 μg of protein was loaded per lane.

Figure 7:
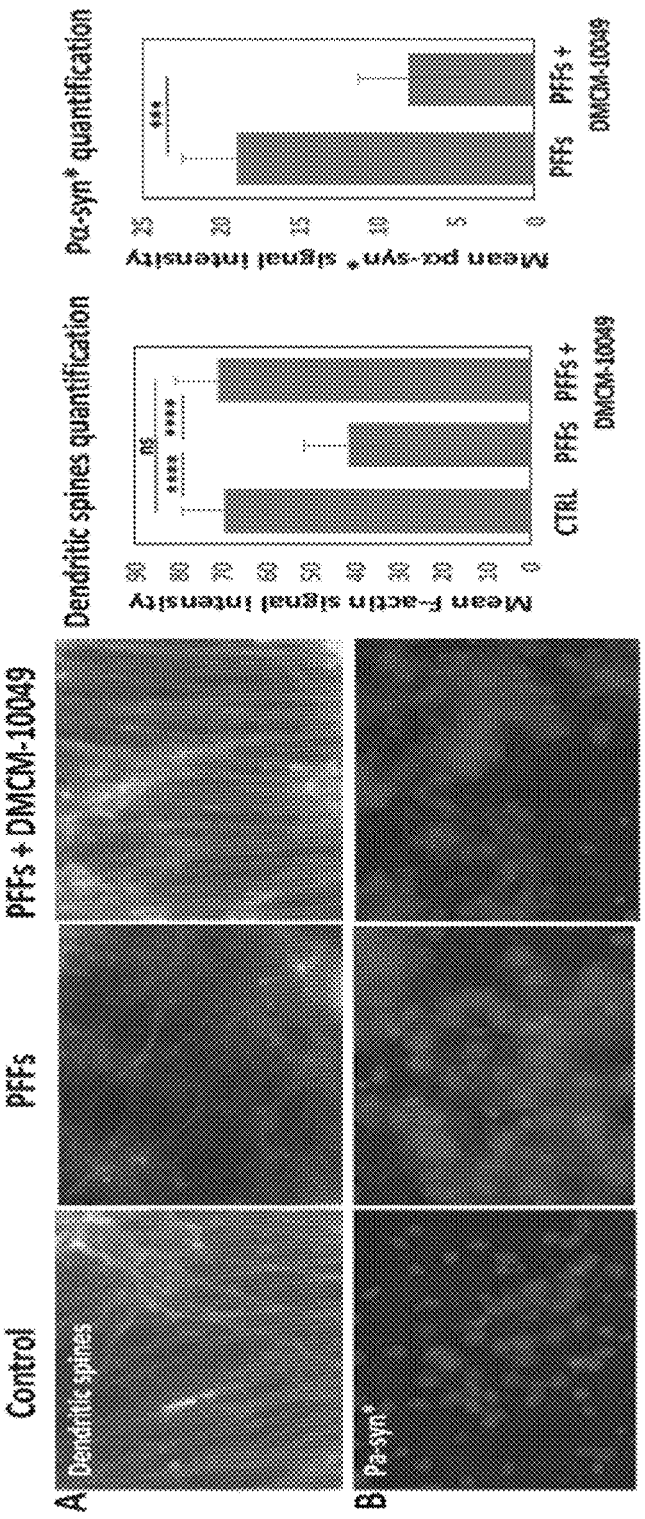

FIG. 7 shows that DMCM-10049 preserves dendritic spines and reduces pα-syn* levels in a cellular PD model. Human stem cell-derived neurons (30 days post-differentiation) were seeded with 50 μg/ml preformed α-synuclein fibrils (PFFs), treated with DMCM-10049 at 2 μM or vehicle, and fixed 17 days later for analysis. Control cells were not PFFs-seeded. A: Dendritic spines were labeled with the marker F-actin using Phalloidin-iFluor 488 (Abcam). B: pα-syn* (red, antibody GTX50222, GeneTex)+DAPI (blue) staining. Quantification was done using ImageJ (NIH), statistical analysis with one way ANOVA (Prism7). Mean values and SDs of 8 images (A) or 6 images (B) per each condition are shown. **$P<0.0001$; *$P<0.001$; ns=non significant.

Figure 8:
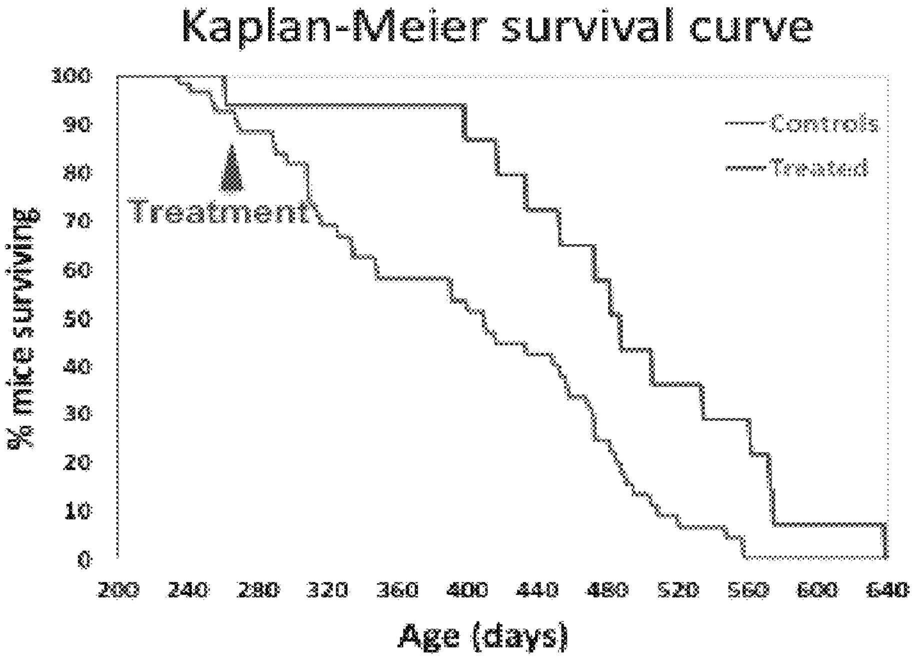

FIG. 8 shows therapeutic effects of DMCM-10049 in a murine model of Parkinson's disease. Tg(SNCA*A53T) mice were treated from 9 months of age with 50 mg/kg/day DMCM-10049 in drinking water. Sugar-free strawberry flavored gelatin (Royal®) was used for taste-masking and 4% DMSO for compound solubilization. Vehicle controls received the same mixture without compound. Median survival was 411 days in the control group (n=48), 488 days in the treatment group (n=16). Prolongation of survival was significant (p=0.01 in the Log-rank test, Prism 7).

Figure 9:
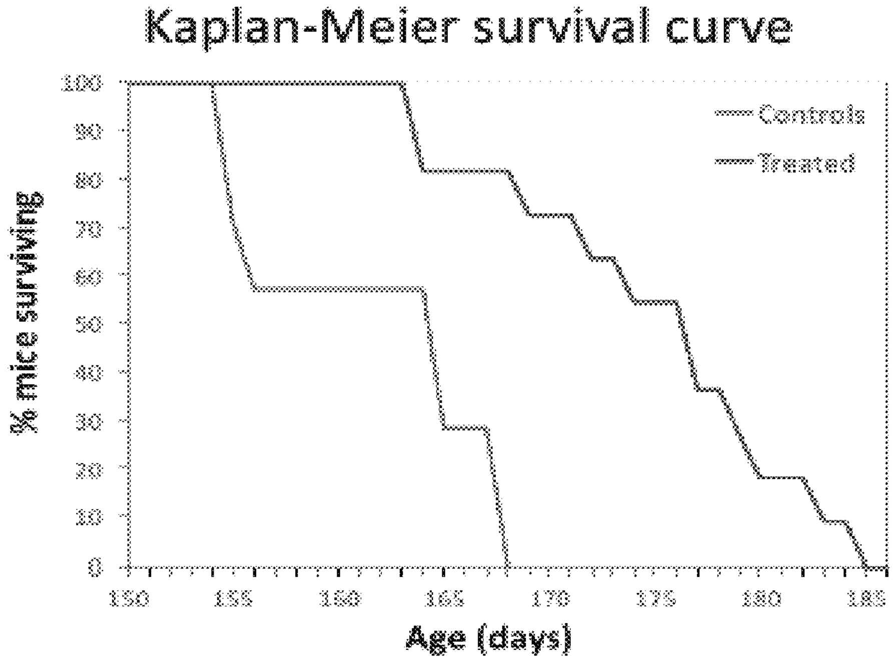

FIG. 9 shows therapeutic effects of DMCM-10049 in a murine model of ALS.

Tg(SOD1*G93A) mice were treated from 70 days of age with 50 mg/kg/day DMCM-10049 in drinking water. Sugar-free strawberry flavored gelatin (Royal®) was used for taste-masking and 4% DMSO for compound solubilization. Vehicle controls received the same mixture without compound. Median survival was 165 days in the control group (n=7), 177 days in the treatment group (n=11). Prolongation of survival was significant (p=0.0007 in the Log-rank test, Prism 7).

FIG. 10 shows that oral vatalanib (SR5-1457) treatment delays impairment of motor function in a mouse model of ALS. Mice (all female) received 50 mg/kg vatalanib daily in their drinking water from day 47 of age. Sugar-free strawberry flavored gelatin (Royal®) is used for taste-masking and 4% DMSO for compound solubilization. Vehicle controls received the same mixture without compound. Rotarod and hanging-wire tests were performed as described[2,3]. Average±SEM are shown. Statistical analysis was performed with 2-way Anova, n=12; *$p<0.05$; $p<0.01$; *$p<0.001$.

FIG. 11 that the SAR for neuroprotective/NAD restoring effects does not correlate with the SAR for VEGFR inhibition in vatalanib analogs. VEGFR active and inactive compounds related to vatalanib (SR5-1457), including the methyl ketone SR1-134005, were prepared and tested in our assays. Dose-response curves are shown for neuroprotection (red) and NAD levels (black), as well as the counterscreen, which is aimed at detecting compounds increasing luminescence/cell viability nonspecifically in the absence of TPrP (green). The assays were performed in the 1536-well plate format as described in the legend of FIG. 2.

Figure 12:
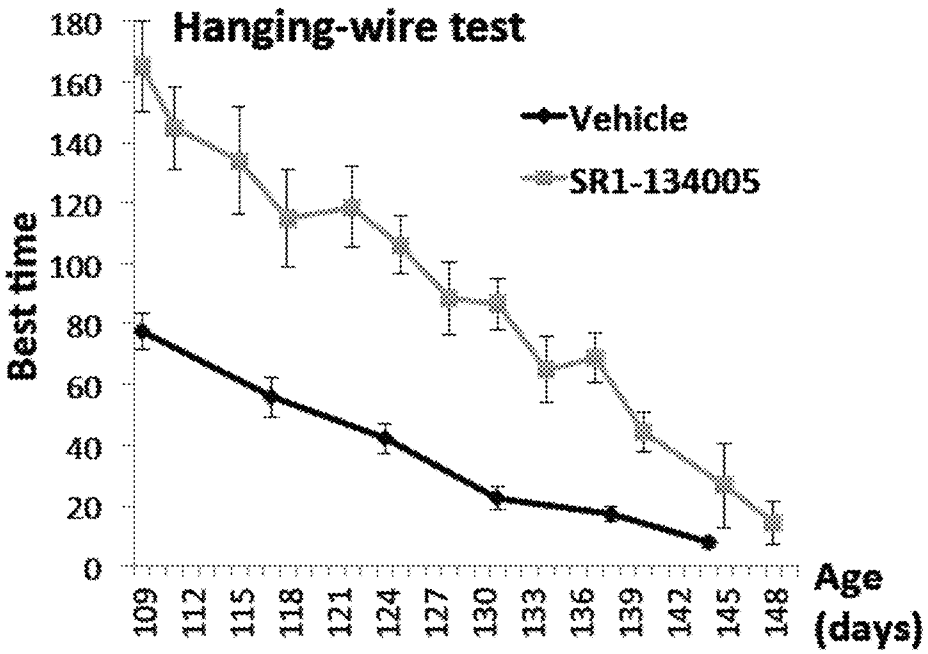

FIG. 12 shows that therapeutic effects of the much less GABAAR-active 3-methyl ketone analog of vatalanib (SR1-134005) in a murine model of ALS. Tg(SOD1*G93A) mice were treated from 100 days of age with 6 mg/kg/day of SR1-134005 in drinking water. Sugar-free strawberry flavored gelatin (Royal®) was used for taste-masking and 4% DMSO for compound solubilization. Vehicle controls received the same mixture without compound. Hanging wire test was performed to measure muscle strength. Average±SEM are shown. The difference between the treated (n=14) and the control group (n=19) was significant ($p<0.001$ for all but the 145 day time point, multiple unpaired t-test, Prism 7).

Figure 13:
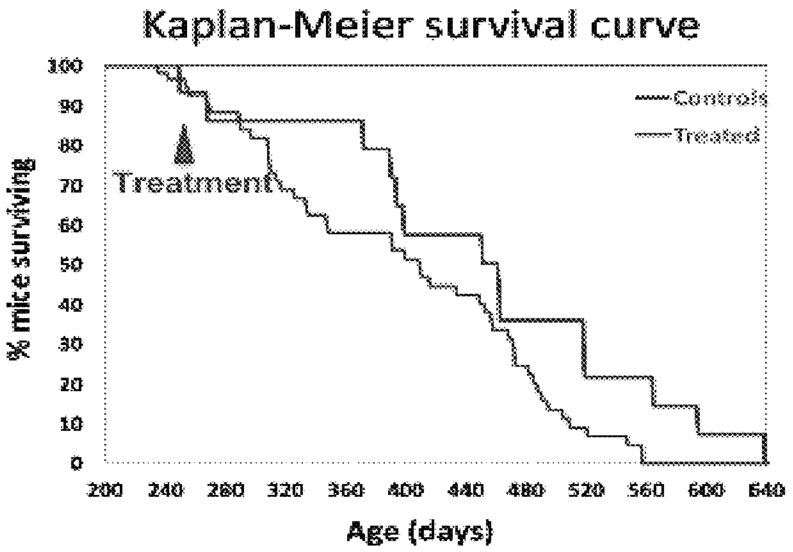

FIG. 13 shows therapeutic effects of the much less GABAAR-active 3-methyl ketone analog of vatalanib (SR1-134005) in a murine model of Parkinson's disease. Tg(SNCA*A53T) mice were treated from 8 months of age with 25 mg/kg/day of SR1-134005 in drinking water. Sugar-free strawberry flavored gelatin (Royal®) was used for taste-masking and 4% DMSO for compound solubilization. Vehicle controls received the same mixture without compound. Median survival was 411 days in the control group (n=58), 462 days in the treatment group (n=16). Prolongation of survival was significant ($p=0.03$ in the Log-rank test, Prism 7).

Figure 14:
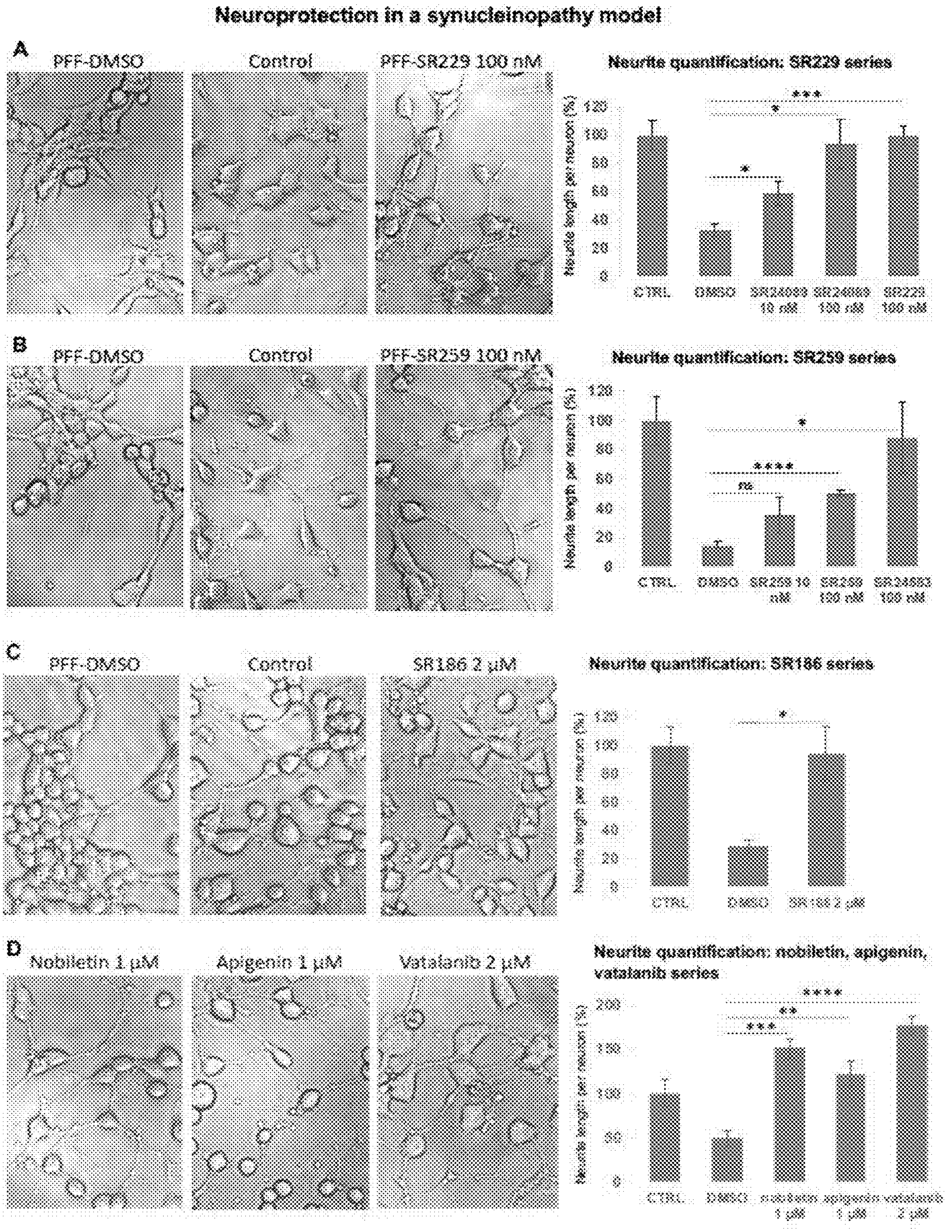

FIG. 14 shows neuroprotection in a cellular PD/synucleinopathy model. Murine stem-cell derived neurons (8 days post-differentiation) were seeded with PFFs (A, B: 4 μg/ml; C, D: 3 μg/ml) and treated with the test compounds at the dose indicated, or with the vehicle DMSO, during the last 2 days of differentiation. Control cells were not PFFs-seeded. Cells were photographed by phase contrast microscopy. Neurite length was quantified using the NeuronJ plugin of ImageJ (NIH), statistical analysis was done in pairs by comparing compound-treated cells with the DMSO control (student's t-test, Prism8). Mean values and SEMs of 4 fields per each condition are shown. Each field contained approximately 50 to 100 neurons. Images shown correspond to a representative area of one field. **$P<0.0001$; *$P<0.001$; **$P<0.01$; *$P<0.05$; ns=not significant.

Figure 15:
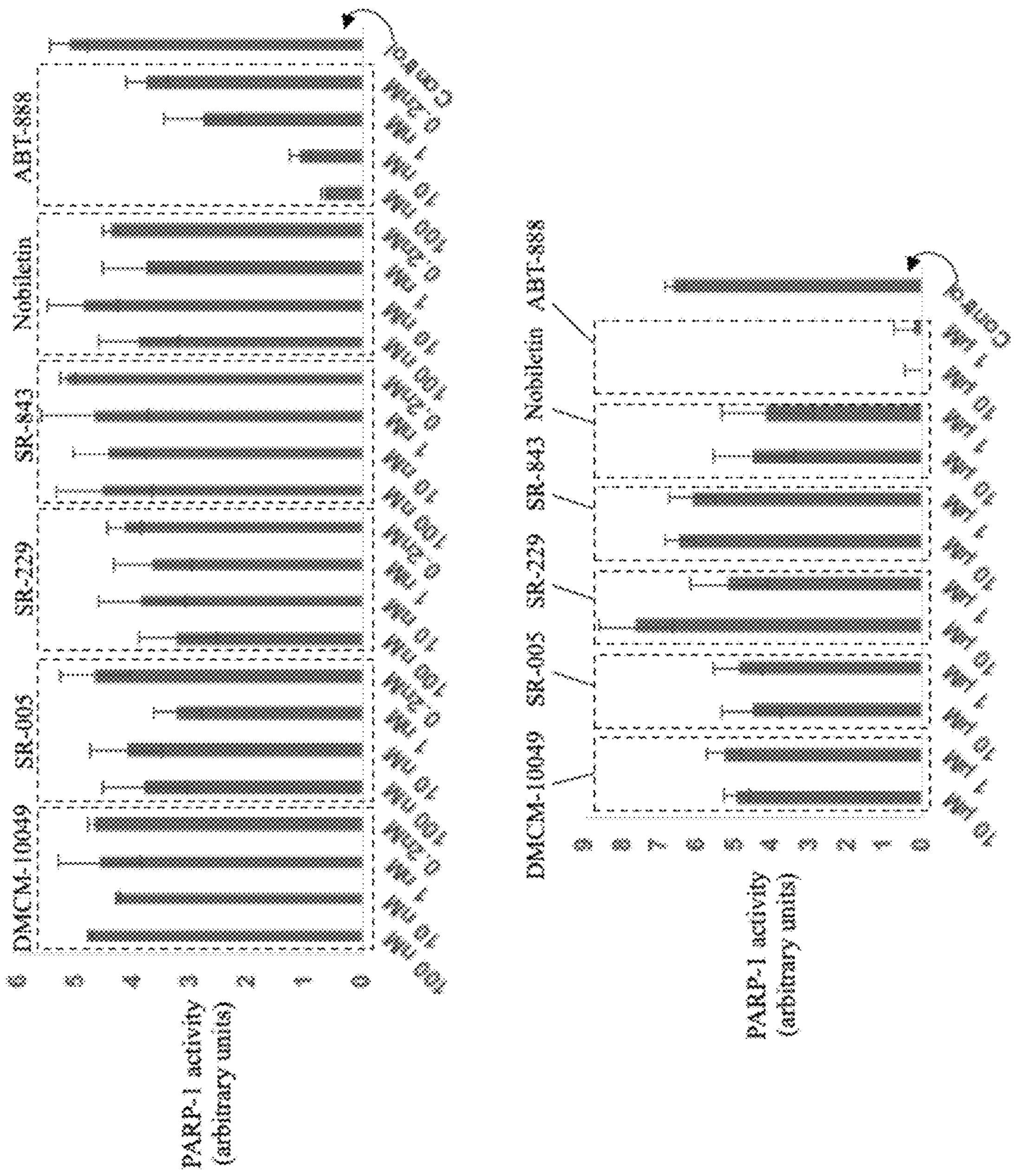

FIG. 15 shows absence of PARP-1 inhibition by a carbazole (DMCM-10049), an aminophthalazine (SR1-134005, aka SR-005), a pyrazolopyrimidine (SR1-293229, aka SR-229), a triazolophthalazine (SR5-22843, aka SR-843), and a flavonoid (nobiletin). ABT-888 is a known PARP1 inhibitor serving as pharmacological control for the assay. "Control" indicates that the assay was performed in the absence of compound. The assay was performed using the BPS Bioscience PARP1 chemiluminescent assay kit according to the manufacturer's instructions.

FIG. 16 shows that the aminophthalazines vatalanib and SR1-134005 (aka SR-005) are NAMPT activators. Compounds were tested in a colorimetric NAMPT activity assay (Abcam, ab221819). Each data point represents a duplicate sample. A, B: Activation of NAMPT by SR-005, but not by DMCM, SR-229, SR-259, SR-186 or nobiletin. Compounds were tested at 5 μM (A) or 20 μM (B). C, D: Dose-dependent activation of NAMPT by SR-005 (C, 0.5 and 2.5 μM; D, 5 and 20 μM). E: Dose-dependent activation of NAMPT by vatalanib. Pazopanib, a potent inhibitor of VEGFR-1, -2 and -3, does not activate NAMPT at 10 μM. This data adds to the previous demonstration that the NAD-restoring effect of vatalanib and SR-005 is not linked to its VEGFR activity.

DETAILED DESCRIPTION

The misfolded toxic prion protein TPrP induces a profound depletion of neuronal NAD that is responsible for cell death, since NAD replenishment leads to full recovery of cells exposed to TPrP injury in vitro and in vivo, despite continued exposure to TPrP[2]. Intranasal NAD treatment improved motor function and activity in murine prion disease. Further it was discovered that NAD depletion in neurons exposed to TPrP was due, at least in part, to overconsumption of cellular NAD during metabolic reactions called mono-ADP ribosylations[2]. Inhibitors of poly-ADP-ribosylations, called PARP inhibitors, have previously been developed as anticancer agents. Available selective PARP inhibitors did not alleviate NAD depletion and neuronal death caused by TPrP, demonstrating the need to identify new compounds capable of interfering with the mechanisms at play in misfolded protein-induced toxicity. Such mechanisms could also be operating in the case of other disorders associated with an imbalance in NAD metabolism, as described herein.

Figure 1:
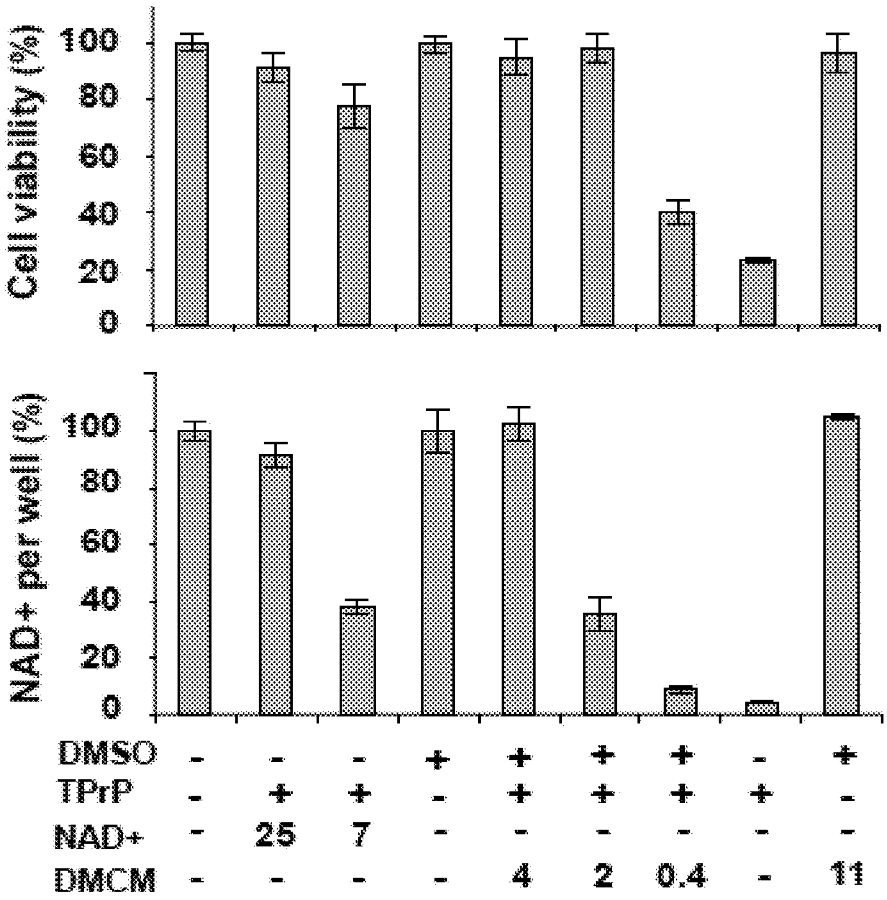
FIG. 1 shows the primary neuroprotection assay and confirmatory NAD quantification assay in the 384 well plate format. PK1 neuroblastoma cells (2000 cells/well) were treated with 2.5 μg/ml TPrP for 3 days as indicated in the presence or absence of either NAD or the screening hit DMCM at the doses indicated (doses in μM). TPrP was prepared as described in Zhou, et. al., *Proc Natl Acad Sci USA* 109, 3113-3118 (2012)[1]. DMSO was 0.3%. Quintuplicates and SDs are shown. Upper panel: luminescent cell viability assay using CellTiter-Glo® (Promega). Lower panel: NAD quantification assay using NAD+/NADH-Glo™ (Promega).

Using TPrP as a prototypic amyloidogenic misfolded protein exhibiting high neurotoxicity, a high-throughput screening (HTS) assay has been developed to identify compounds effective at a) preventing neuronal death; and b) preventing NAD depletion induced by TPrP (FIG. 1).

The HTS campaign was performed at Scripps Florida using a subset of the Scripps Drug Discovery Library (SDDL). Several potent, novel and chemically tractable small molecules are identified that can provide complete neuroprotection and preservation of NAD levels when used at doses ranging from low nanomolar to low micromolar levels. Among the highly active compounds were DMCM, an allosteric $GABA_A$ receptor ($GABA_A$ R) modulator, and vatalanib, a VEGF receptor (VEGFR) tyrosine kinase inhibitor that has been studied in clinical trials for the treatment of cancer. Six other classes of neuroprotective molecules were also identified in this effort.

Exemplary active compounds are provided below:

1) carbazoles (example: SR1-75869, aka DMCM)

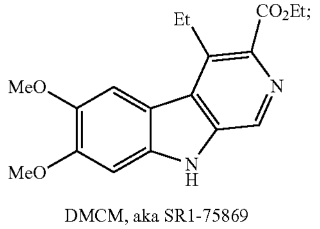

DMCM, aka SR1-75869

-continued 2) pyrazolopyrimidines (example: SR1-293229)

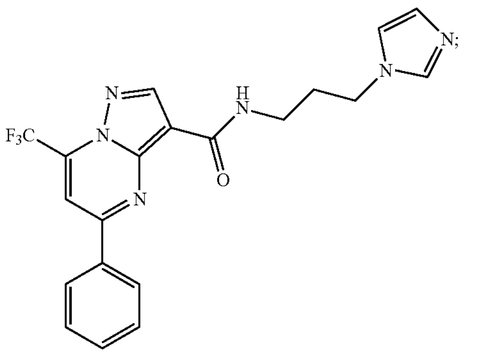

SR1-293229

3) aminothiazoles (example: SR1-477186)

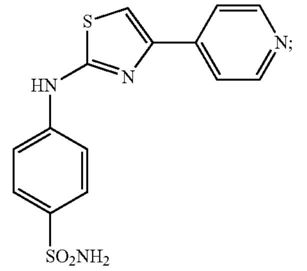

SR1-477186

4) triazolophthalazines (example: SR1-115259)

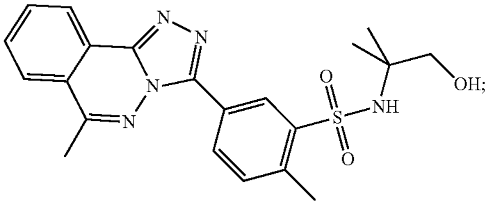

SR1-115259

5) aminophthalazines (examples: SR5-1457, aka vatalanib, aka CGP79787, and also SR1-134005, a much less $GABA_A$R-active analog of vatalanib);

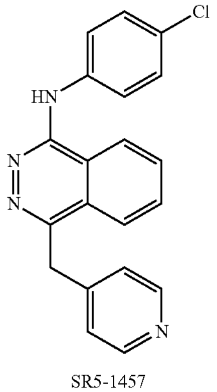

SR5-1457
aka vatalanib
aka CGP79787

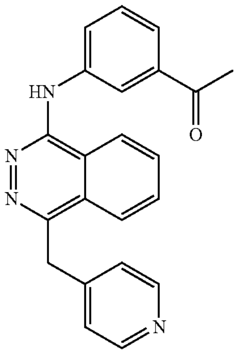

SR1-134005

-continued 6) flavonoids (example: nobiletin, aka SR1-712262)

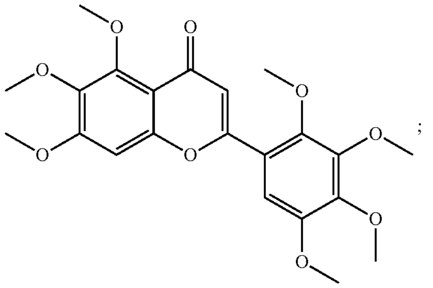

nobiletin, aka SR1-712262

7) alkaloids, including isoquinoline, aporphine, and ergot alkaloids (example shown is an isoquinoline alkaloid, named palmatine chloride, aka SR1-841226);

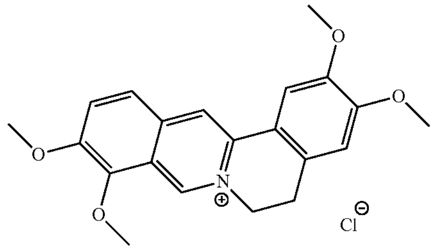

palmatine chloride
aka SR1-841226

8) 3-heteroarylquinolines (example: DMPQ, aka SR1-597975).

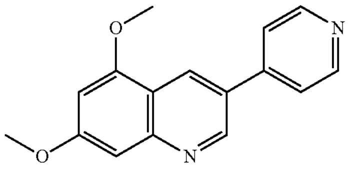

DMPQ
SR1-597975

Activities of the above compound series are characterized in detail in FIGS. 2A-2H. Members of each series are highly potent in neuroprotection assays designed to reflect the potential for the successful treatment of several neurodegenerative diseases as described herein. Further, many have favorable properties for lead development (e.g., they are PAINS-free[4] and compliant with Lipinski and Veber rules for drug-likeness[5,6]).

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl ("Me"), ethyl ("Et"), n-propyl ("Pr"), isopropyl ("iPr"), n-butyl ("Bu"), t-butyl ("t-Bu"), isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

An "arylene" and a "heteroarylene," alone or as part of another substituent, mean a divalent radical derived from an aryl and heteroaryl, respectively. A heteroaryl group substituent may be —O— bonded to a ring heteroatom nitrogen.

The symbol "〰" denotes the point of attachment of a chemical moiety to the remainder of a molecule or chemical formula.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The term "$EC_{50}$" or "half maximal effective concentration" as used herein refers to the concentration of a molecule (e.g., small molecule, drug, antibody, chimeric antigen receptor or bispecific antibody) capable of inducing a response which is halfway between the baseline response and the maximum response after a specified exposure time. In embodiments, the $EC_{50}$ is the concentration of a molecule (e.g., small molecule, drug, antibody, chimeric antigen receptor or bispecific antibody) that produces 50% of the maximal possible effect of that molecule.

As used herein, the term "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Chronic Traumatic Encephalopathy, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, Kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

Compounds

In an aspect, provided herein are compounds that may provide complete neuroprotection and protection of cell types other than neurons, and preservation of NAD levels. The compounds may be highly potent in a) preventing neuronal and/or cellular death; and b) preventing NAD depletion induced by TPrP, for example, as identified by neuroprotection assays when used at doses ranging from low nanomolar to low micromolar levels.

In an aspect, a compound has a Formula (I), (I)

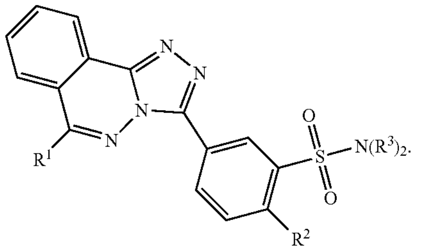

In Formula (I),

Each $R^1$ and $R^2$ are independently hydrogen, $(C_1-C_4)$alkyl, or $(C_1-C_4)$alkoxy; and Each $R^3$ is independently selected hydrogen, $(C_1-C_4)$alkyl optionally substituted with OH, $(C_1-C_4)$alkoxy, or heteroaryl, and provided that both $R^3$ are not H; or both $R^3$ together with the nitrogen atom to which they are bonded form a 5- to 7-membered heterocyclyl ring comprising at least on additional heteroatom selected from O, S, S═O, S(═O)═O, or NR, wherein R is $(C_1-C_4)$alkyl optionally substituted with —OH or $(C_1-C_4)$alkoxyl.

The compound of Formula (I) includes all pharmaceutically acceptable salt forms.

In embodiments, $R^1$ is methyl.

In embodiments, $R^2$ is methyl.

In embodiments, one of $R^3$ is hydrogen and the other $R^3$ is

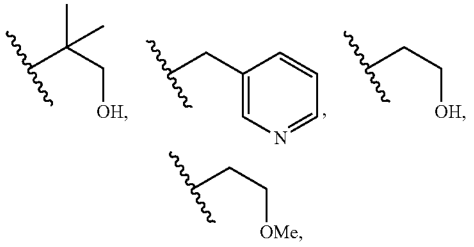

methyl,

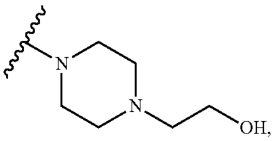
,
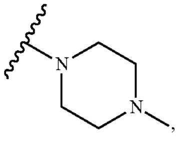
, or
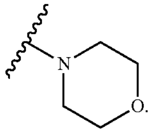
.

In some compounds of Formula (I), when $R^1$ and $R^2$ are methyl, one of $R^3$ is hydrogen, then the other $R^3$ is not or methyl.

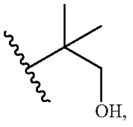
,
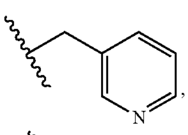
,
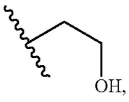
,
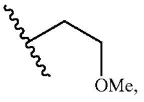
,

In some compounds of Formula (I), when $R^1$ and $R^2$ are methyl, two $R^3$ attached to the nitrogen atom does not form

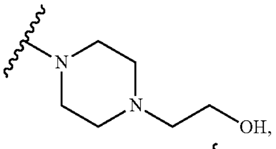
,
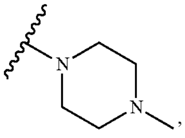
, or
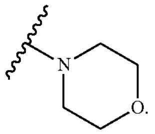
.

In an aspect, a compound has a Formula (II), (II)

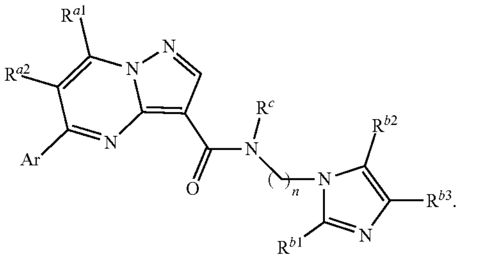
.

In Formula (II):

Each $R^{a1}$ and $R^{a2}$ is independently hydrogen, $(C_1-C_4)$ alkyl, $(C_1-C_4)$haloalkyl, $(C_1-C_4)$alkoxyl, $(C_1-C_4)$haloalkoxyl, 2 to 4 membered heteroalkyl, cycloalkyl, heterocycloalkyl, aryl, or heteroaryl;

Each $R^{b1}$, $R^{b2}$, and $R^{b3}$ is independently hydrogen, halo, $(C_1-C_4)$alkyl, —$S(O)_2R^d$, —$S(O)_2OR^d$, or $(C_1-C_4)$haloalkyl; or $R^{b2}$ and $R^{b3}$ are joined together to form an aryl or heteroaryl;

Each $R^c$ and $R^d$ is independently hydrogen or $(C_1-C_4)$ alkyl;

Ar is mono- or bi-cyclic aryl or heteroaryl, optionally substituted with one or more halo, $(C_1-C_4)$alkyl, $(C_1-C_4)$haloalkyl, $(C_1-C_4)$alkoxyl, $(C_1-C_4)$haloalkoxyl, or heteroaryl; and n=2, 3, 4, or 5.

The compound of Formula (II) includes all pharmaceutically acceptable salt forms.

In embodiments, $R^{b1}$ is hydrogen. In embodiments, $R^{b1}$ is $C_1-C_4$ alkyl. In embodiments, $R^{b1}$ is methyl. In embodiments, $R^{b1}$ is ethyl. In embodiments, $R^{b1}$ is halo. In embodiments, $R^{b1}$ is —F. In embodiments, $R^{b1}$ is $(C_1-C_4)$haloalkyl. In embodiments, $R^{b1}$ is —$CF_3$. In embodiments, $R^{b1}$ is —$S(O)_2R^c$ In embodiments, $R^{b1}$ is —$S(O)_2CH_3$.

In embodiments, $R^{b2}$ is hydrogen. In embodiments, $R^{b2}$ is methyl. In embodiments, $R^{b3}$ is hydrogen. In embodiments, $R^{b3}$ is methyl. In embodiments, $R^c$ is hydrogen. In embodiments, $R^c$ is methyl. In embodiments, $R^d$ is hydrogen. In embodiments, $R^d$ is methyl.

In embodiments, $R^{b2}$ and $R^{b3}$ are joined together to form a phenyl.

In embodiments, $R^{a2}$ is hydrogen. In embodiments, $R^{a2}$ is $(C_1-C_4)$alkyl. In embodiments, $R^{a2}$ is methyl.

In embodiments, the compound has the following formula:

(II-a)

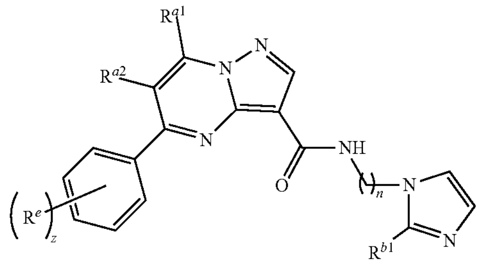

or (II-b)

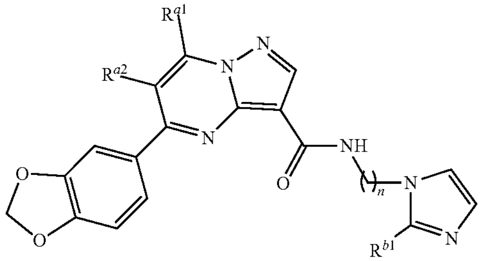

$R^{a1}$ and $R^{b1}$ are as described herein. $R^e$ is independently halo, $(C_1-C_4)$alkyl, $(C_1-C_4)$haloalkyl, $(C_1-C_4)$alkoxyl, $(C_1-C_4)$haloalkoxyl, or heteroaryl, and z is 0, 1, 2, 3, 4, or 5.

In embodiments, z is 0, 1, 2, or 3.

In embodiments, $R^{b1}$ is hydrogen, methyl, ethyl, —F, —$CF_3$, or —$S(O)_2Me$.

In embodiments, $R^{a2}$ is hydrogen or methyl.

In embodiments, n is 2. In embodiments, n is 3. In embodiments, n is 4.

In embodiments, $R^{a1}$ is $(C_1-C_4)$alkyl. In embodiments, $R^{a1}$ is methyl. In embodiments, $R^{a1}$ is ethyl. In embodiments, $R^{a1}$ is isopropyl. In embodiments, $R^{a1}$ is t-butyl. In embodiments, $R^{a1}$ is $(C_1-C_4)$haloalkyl. In embodiments, $R^{a1}$ is —$CF_3$. In embodiments, $R^{a1}$ is heterocycloalkyl. In embodiments, $R^{a1}$ is

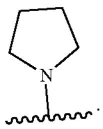

In embodiments, $R^{a1}$ is —$CH_2$—O—$CH_3$. In embodiments, $R^{a1}$ is phenyl.

In embodiments, Ar is phenyl optionally substituted with one or more of halo, $(C_1-C_4)$alkyl, $(C_1-C_4)$haloalkyl, $(C_1-C_4)$alkoxyl, $(C_1-C_4)$haloalkoxyl, or heteroaryl In embodiments, Ar is

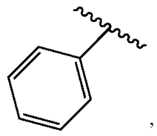
,
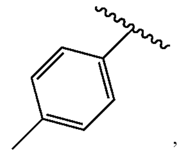
,
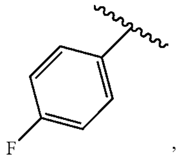
,
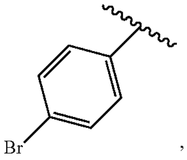
,
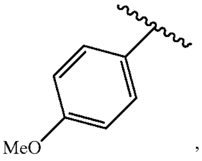
,
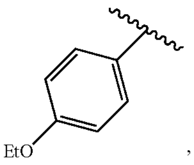
,
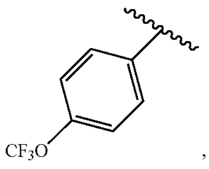
, or
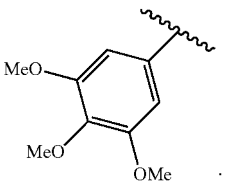
.

In embodiments, Ar is

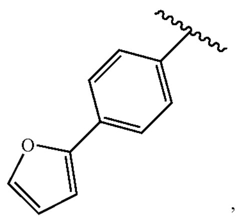
, or
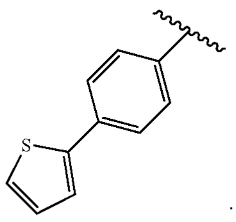
.

In embodiments, Ar is

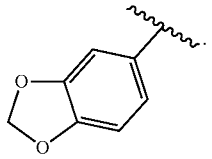 [SMILES: *c1ccc2c(c1)OCO2]

In some compounds of Formula (II), when $R^{a2}$, $R^{b1}$, $R^{b2}$, $R^{b3}$, and $R^c$ are hydrogen, n is 3, Ar is phenyl which is unsubstituted or substituted with —$CH_3$ or —OMe, then $R^{a1}$ is not difluoromethyl or trifluoromethyl.

In some compounds of Formula (II), when $R^{a2}$, $R^{b1}$, $R^{b2}$, $R^{b3}$, and $R^c$ are hydrogen, n is 3, Ar is phenyl substituted with —F, Br,

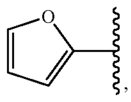
, or
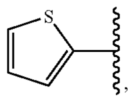
, then $R^{a1}$ is not trifluoromethyl.

In embodiments, the compounds of Formula (II) include:

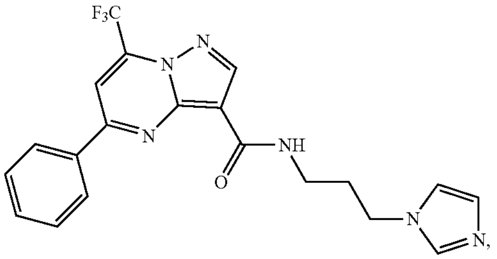

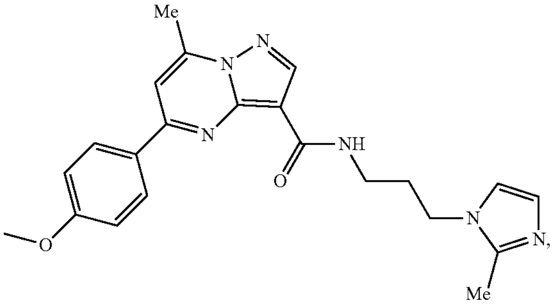

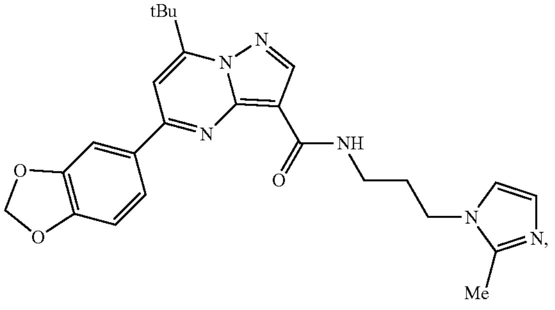

-continued
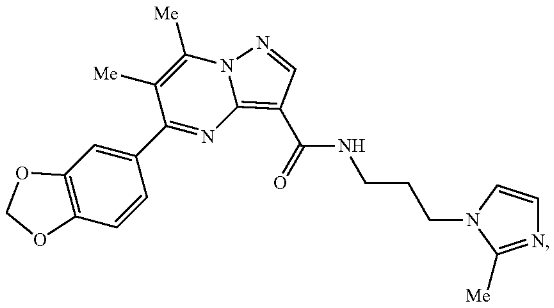
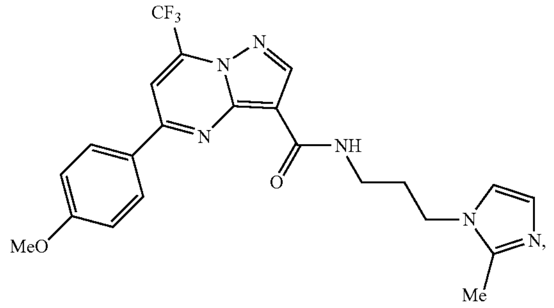
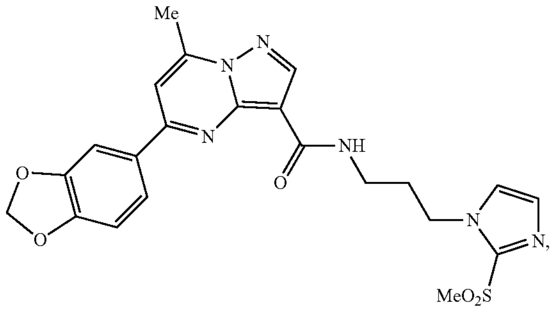
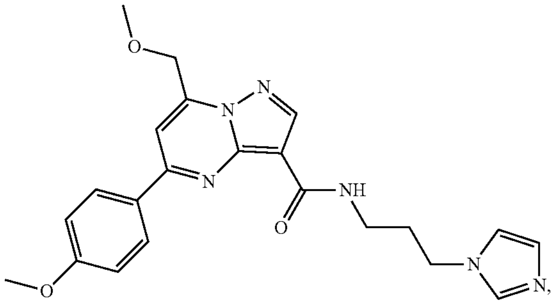
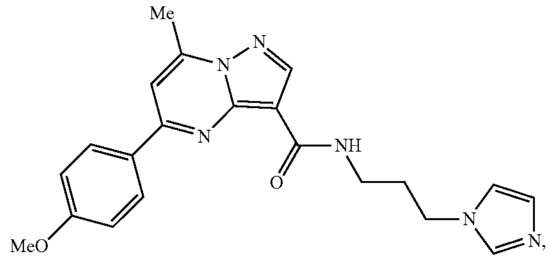
-continued
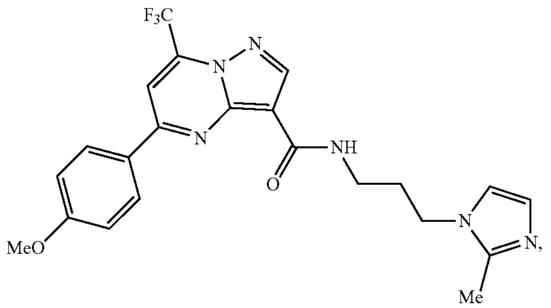
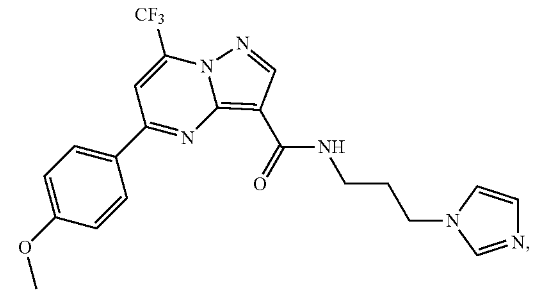
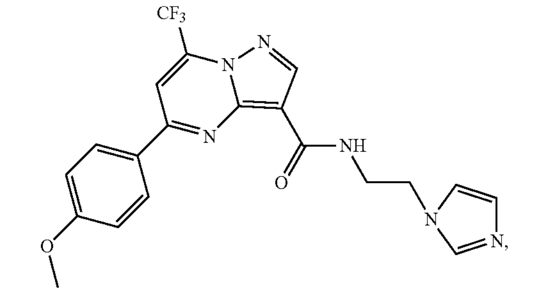
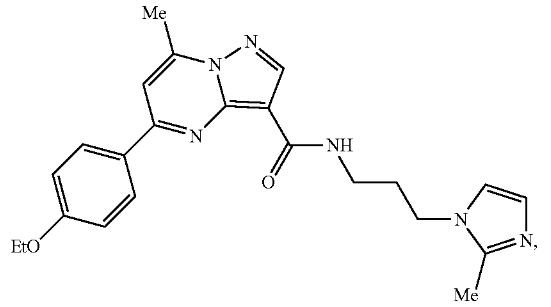
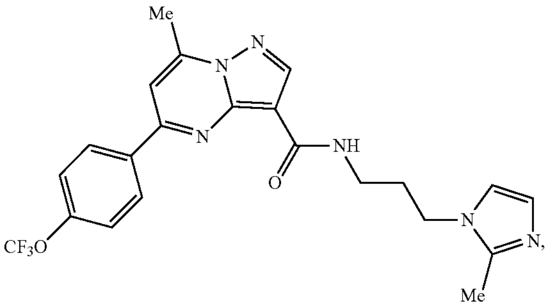

-continued
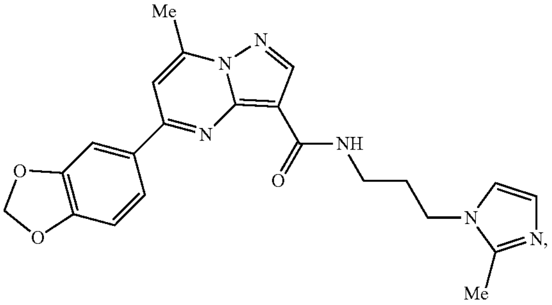
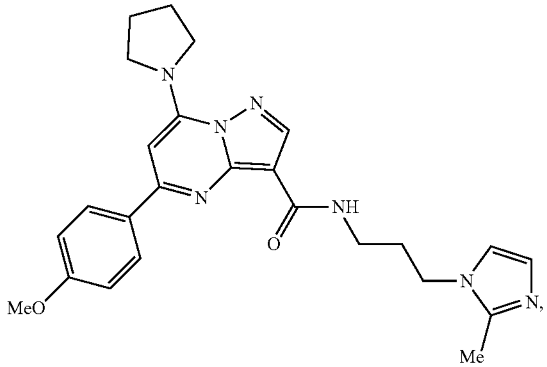
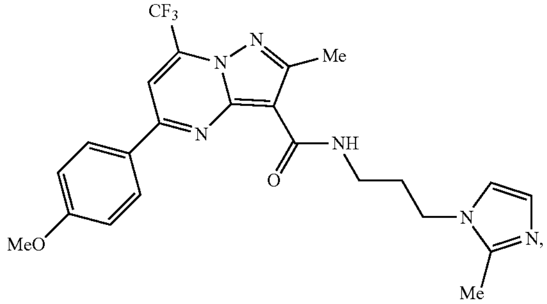
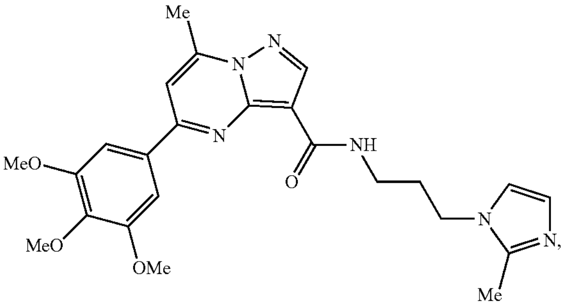
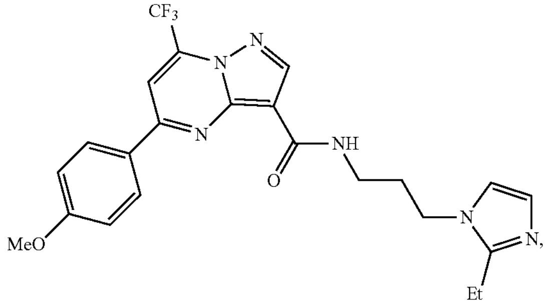
-continued
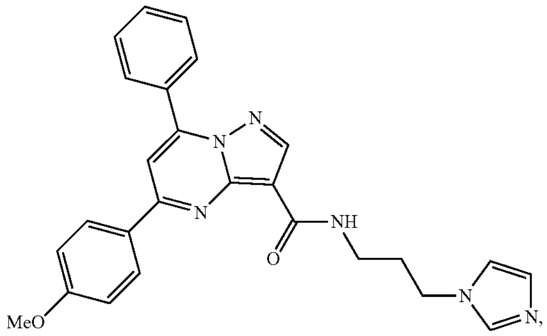
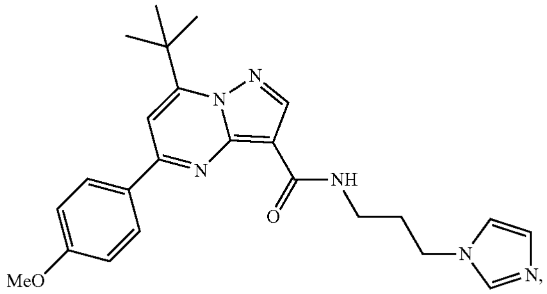
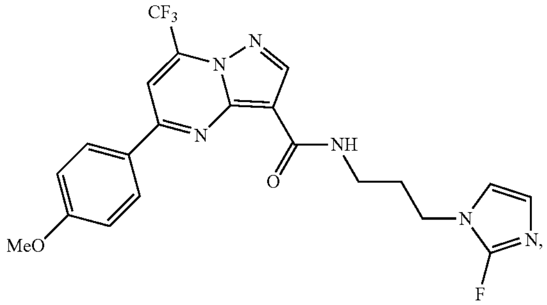
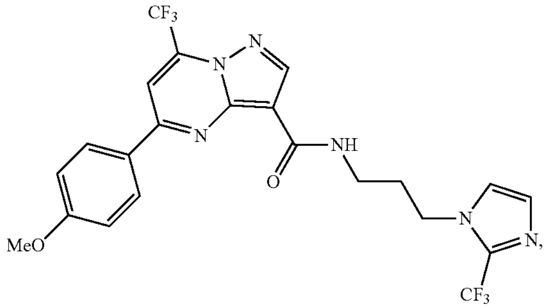
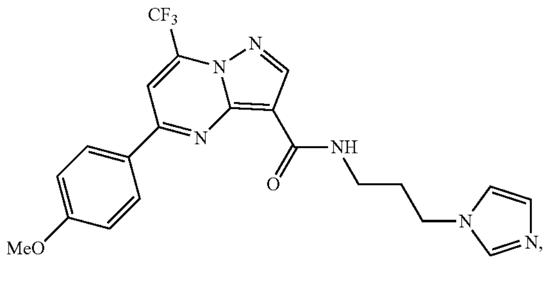

-continued
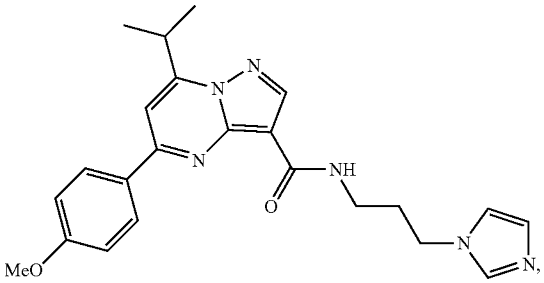
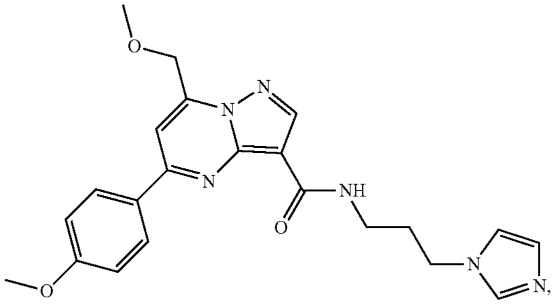
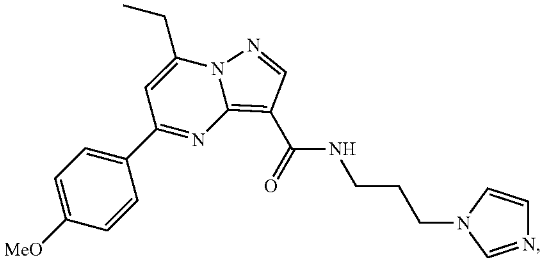
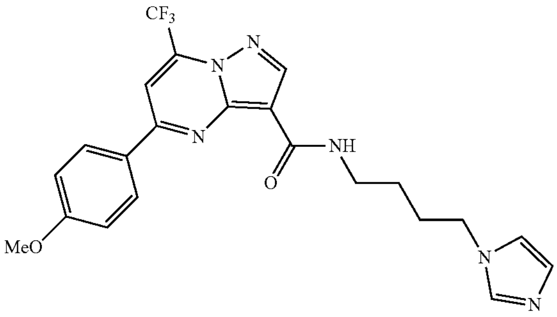
,
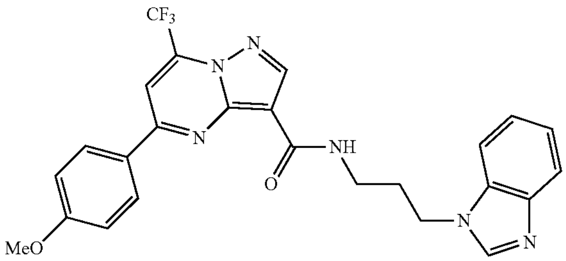
,
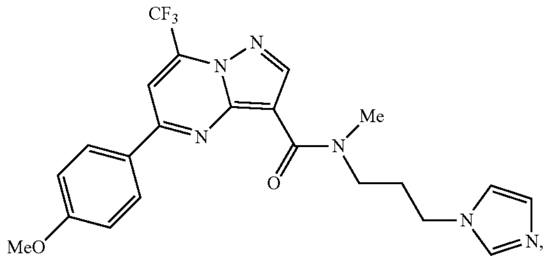
-continued
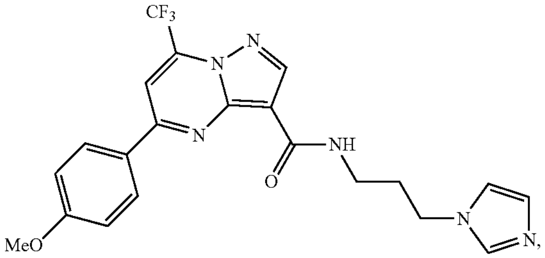
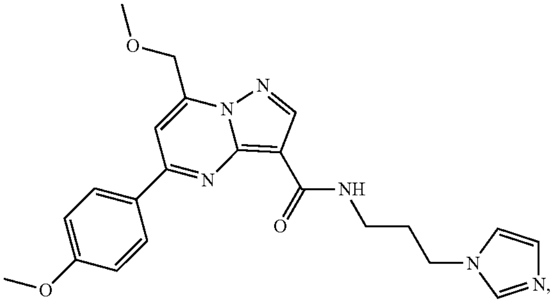
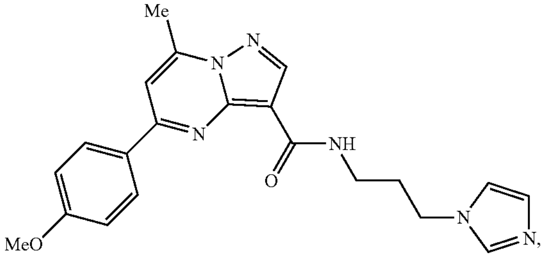
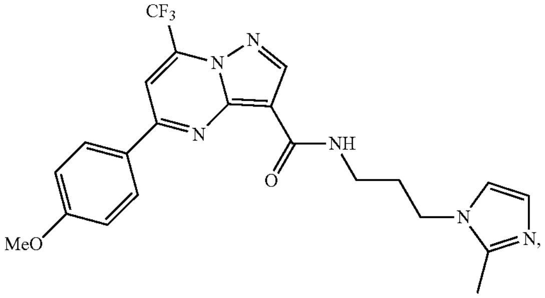
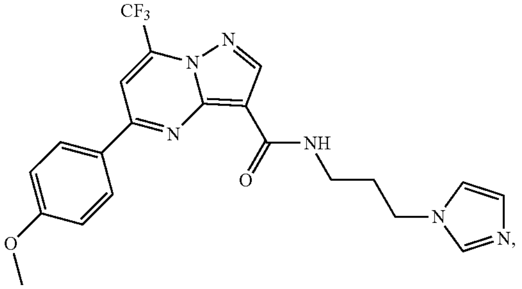
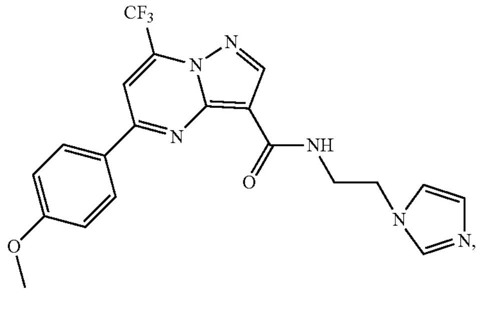
or -continued

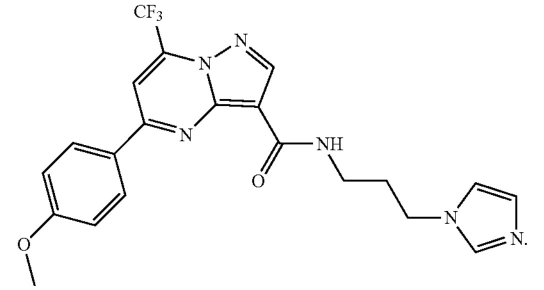 [SMILES: COc1ccc(-c2cc(C(F)(F)F)n3ncc(C(=O)NCCCn4ccnc4)c3n2)cc1]

In an aspect, a compound has a Formula (III),

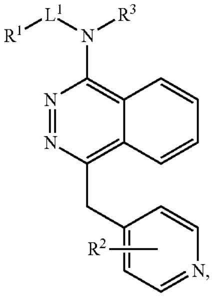

(III)

In Formula (III), $L^1$ is a bond, $C_1$-$C_4$ alkylene, or 2 to 4-membered heteroalkylene;

$R^1$ is mono- or bi-cyclic cycloalkyl, heterocycloalkyl, aryl, alkylaryl, or heteroaryl, wherein the cycloalkyl, heterocycloalkyl, aryl, alkylaryl or heteroaryl is optionally substituted with one or more selected from halo, $(C_1$-$C_4)$alkyl, hydroxy$(C_1$-$C_4)$alkyl, $(C_1$-$C_4)$alkoxyl, $—C(=O)(C_1$-$C_4)$alkyl, $—C(=O)N(R)_2$, or $—C(=NR)(C_1$-$C_4)$alkyl, wherein the $(C_1$-$C_4)$alkyl is unsubstituted or substituted with heterocycloalkyl;

each R is independently hydrogen, —OH, $(C_1$-$C_4)$alkyl, or $(C_1$-$C_4)$alkoxyl, or two R together with the nitrogen atom to which it is bonded form a heterocycloalkyl, optionally further comprising an O atom in the heterocyclyl ring;

$R^2$ occurs 0, 1, or 2 times, and is $(C_1$-$C_4)$alkyl, $(C_1$-$C_4)$ haloalkyl, or $SO_2N(R^4)_2$;

each $R^3$ and $R^4$ is independently H, or $(C_1$-$C_4)$alkyl.

The compound of Formula (III) includes all pharmaceutically acceptable salt forms.

In embodiments, $L^1$ is a bond. In embodiments, $L^1$ is methylene. In embodiments, $L^1$ is $—CH_2CH_2—O—$.

In embodiments, $R^1$ is

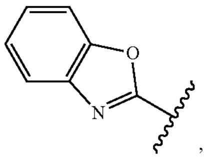 , 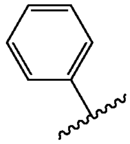 ,

-continued

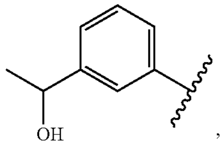 , 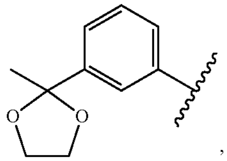 ,

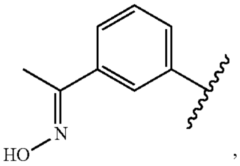 , 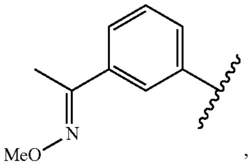 ,

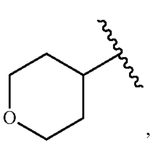 , 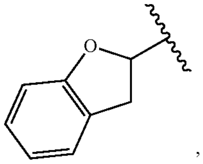 , 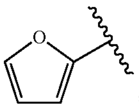 ,

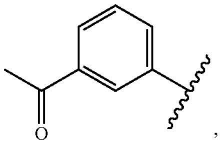 , 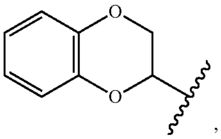 ,

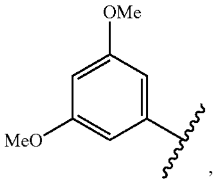 , 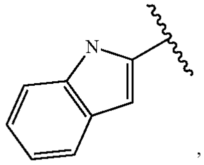 ,

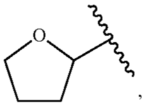 , 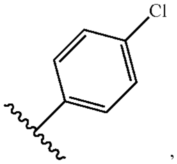 , 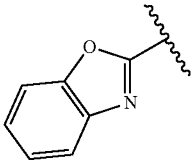 ,

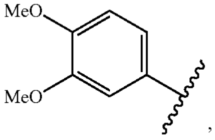 , 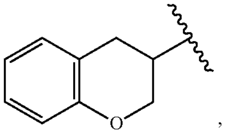 ,

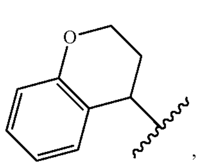 , 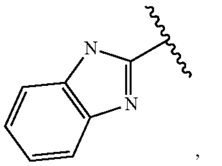 ,

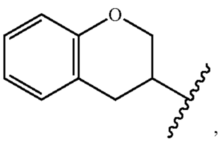 , or 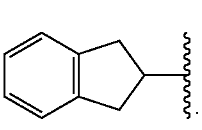 .

In embodiments, $R^2$ does not occur. In embodiment, $R^2$ occurs once.

In embodiments, $R^3$ is hydrogen. In embodiment, $R^3$ is methyl.

In embodiments, the compound has the following formula:

(III-a)
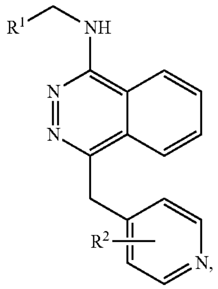
or
(III-b)
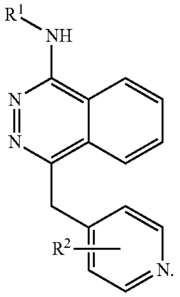
$R^1$ and $R^2$ are described herein.
In some compounds of Formula (III), when $L^1$ is a bond, $R^2$ does not occur, and $R^3$ is hydrogen, then $R^1$ is not
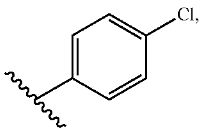
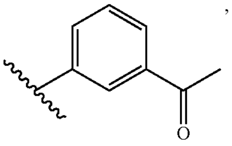
, and
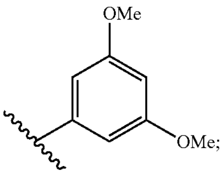
and
In some compounds of Formula (III), when $L^1$ is methylene, $R^2$ does not occur, and $R^3$ is hydrogen, then $R^1$ is not
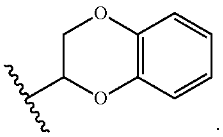 [SMILES: *C1COc2ccccc2O1]
.
In embodiments, the compounds of Formula (III) include:
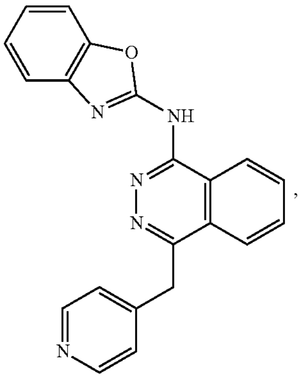
,
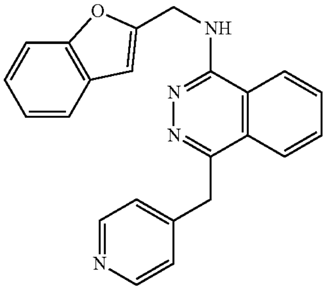
,
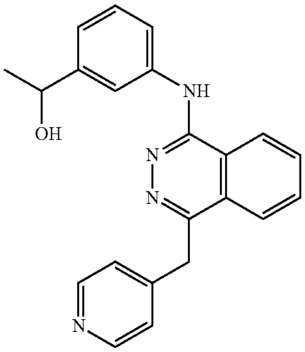
,
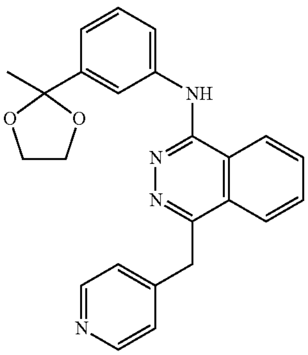
, -continued
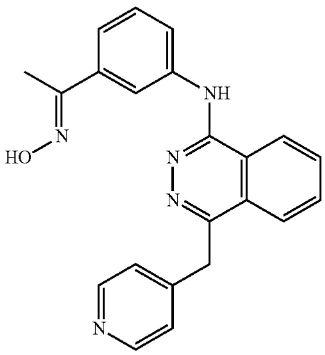
,
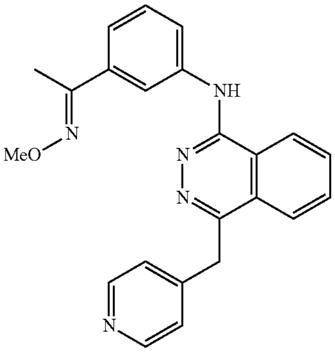
,
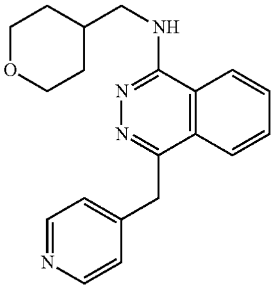
,
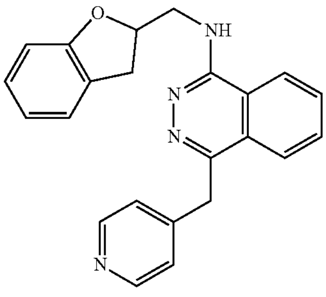
,
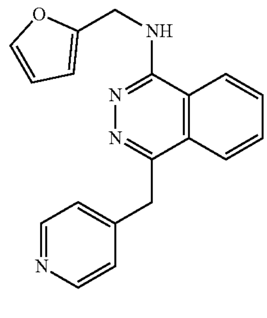
,
-continued
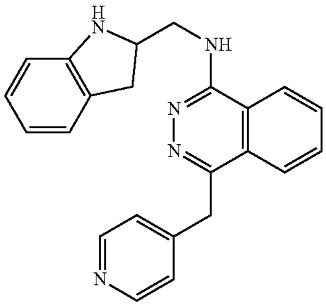
,
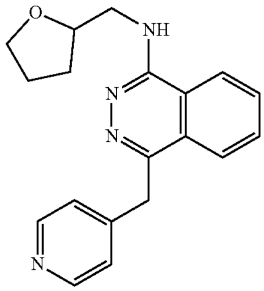
,
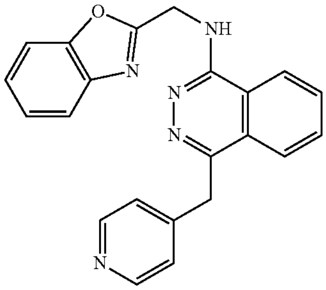
,
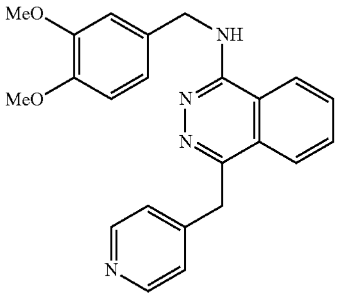
,
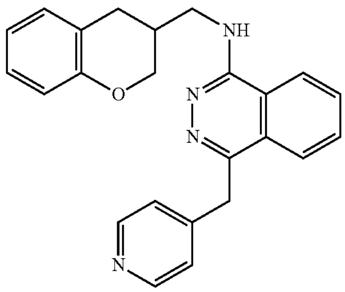
, -continued

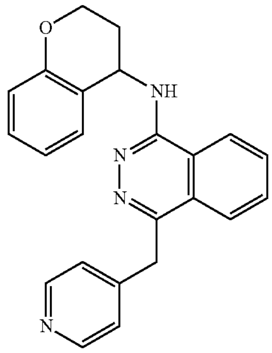

,

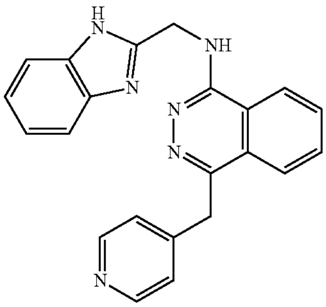

,

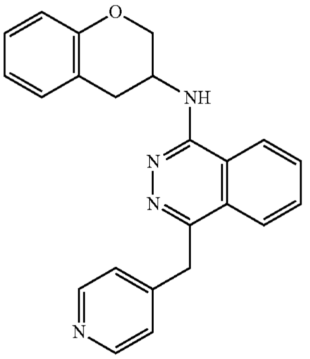

,

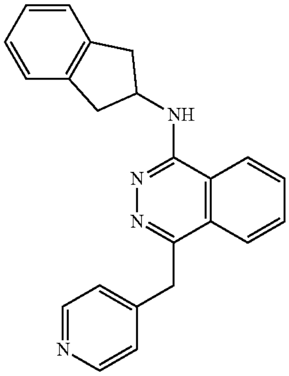

,

-continued

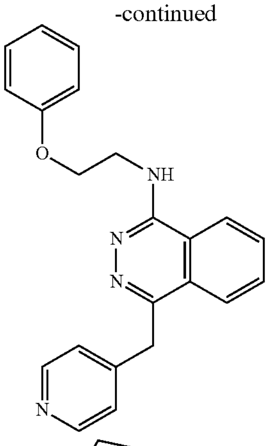

, or

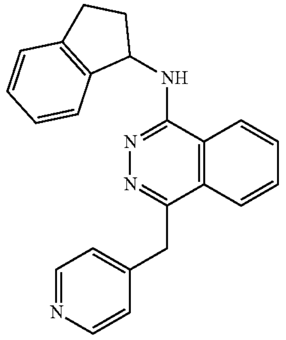

.

In embodiments, a compound has a Formula (IV), (IV)

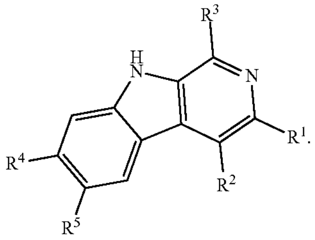

In Formula (IV), $R^1$ is hydrogen, $(C_1\text{-}C_4)$alkyl, —C(O)OH, —C(O)O—$(C_1\text{-}C_4)$alkyl, —C(O)NHNH$R^6$, —C(O)N$R^6$—($(C_1\text{-}C_4)$alkylene)-NH$R^6$, —C(O)N$R^6$$(C_1\text{-}C_4)$alkyl, or —C(O)N$R^6$-cycloalkylene-NH$R^6$;

$R^3$ is hydrogen or $(C_1\text{-}C_4)$alkyl; and each $R^2$, $R^4$, $R^5$ is independently hydrogen, halo, $(C_1\text{-}C_4)$ alkyl, —C(O)O—$(C_1\text{-}C_4)$alkyl, $(C_1\text{-}C_4)$alkoxyl, $(C_1\text{-}C_4)$haloalkyl, or CN; and Each $R^6$ is hydrogen or $(C_1\text{-}C_4)$alkyl.

The compound of Formula (IV) includes all pharmaceutically acceptable salt forms.

In embodiments, each $R^4$ and $R^5$ is independently hydrogen or $(C_1\text{-}C_4)$alkoxyl. In embodiments, each $R^4$ and $R^5$ are —OMe. In embodiments, $R^4$ is hydrogen and $R^5$ is —OMe. In embodiments, $R^5$ is hydrogen and $R^4$ is —OMe.

In embodiments, $R^1$ is hydrogen, $(C_1\text{-}C_4)$alkyl. In embodiments, $R^1$ is methyl. In embodiments, $R^1$ is ethyl. In embodiments, $R^1$ is —C(O)OH, or —C(O)$OCH_3$. In embodiments, $R^1$ is —C(O)NH$(C_1\text{-}C_4)$alkyl. In embodiments, $R^1$ is —C(O)NH$CH_3$.

In embodiments, $R^1$ is —C(O)NH—(($C_1$-$C_4$)alkylene)-$NH_2$ or —C(O)NH-cycloalkylene-$NH_2$. In embodiments, $R^1$ is —C(O)NH—$CH_2CH_2$—$NH_2$, —C(O)$NCH_3$—$CH_2CH_2$—$NHCH_3$,

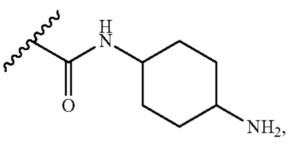 [SMILES: *C(=O)NC1CCC(N)CC1]

or —C(O)$NHNH_2$.

In embodiments, $R^3$ is hydrogen or methyl.

In embodiments, $R^2$ is hydrogen, ($C_1$-$C_4$)alkyl, or —C(O)O—($C_1$-$C_4$)alkyl. In embodiments, $R^2$ is hydrogen. In embodiments, $R^2$ is ethyl. In embodiments, $R^2$ is methyl. In embodiments, $R^2$ is —C(O)$OCH_3$. In embodiments, $R^2$ is —C(O)$OCH_2CH_3$.

In embodiments, $R^6$ is independently hydrogen. In embodiments, $R^6$ is independently methyl.

In some compounds of Formula (IV), when $R^4$ and $R^5$ are —OMe, $R^3$ is hydrogen, and $R^2$ is ethyl, then $R^1$ is not —COOMe.

In some compounds of Formula (IV), when $R^4$ is —OMe, $R^5$ is hydrogen, and $R^1$ and $R^2$ are hydrogen, then $R^3$ is not methyl.

In some compounds of Formula (IV), when $R^2$, $R^3$, $R^4$, and $R^5$ are hydrogen, and then $R^1$ is not —C(O)$NHCH_3$.

In embodiments, the compounds of Formula (IV) include:

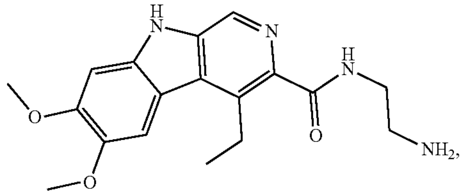

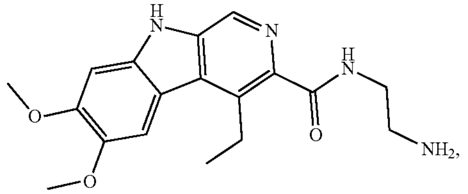

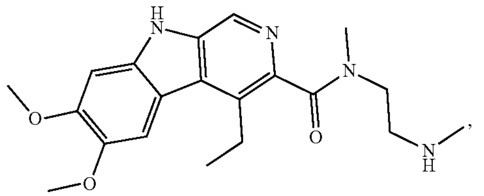

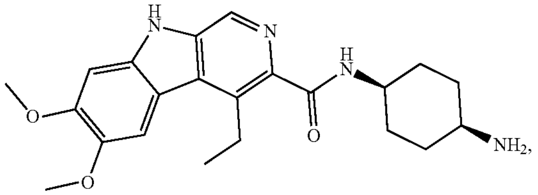

-continued

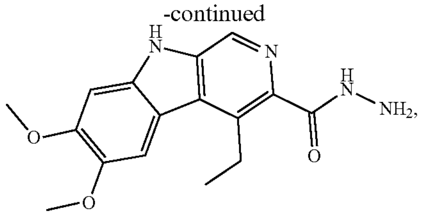

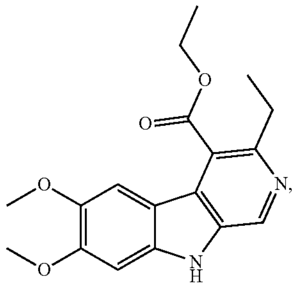

or

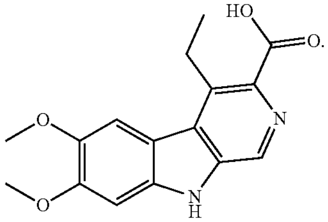

In embodiments, a compound has a Formula (V), (V)

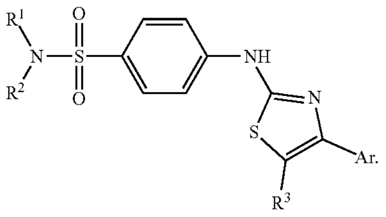

In Formula (V):

Ar is mono- or bi-cyclic aryl or heteroaryl, optionally substituted one or more with halo, ($C_1$-$C_4$)alkyl, ($C_1$-$C_4$)haloalkyl, CN, —S(O)$_2$$NH_2$, oxo, —$NH_2$, ($C_1$-$C_4$) alkoxyl, or —NHC(O)($C_1$-$C_4$)alkyl;

Each $R^1$ and $R^2$ is independently hydrogen, ($C_1$-$C_4$)alkyl, aryl or heteroaryl, wherein the aryl or heteroaryl is optionally substituted with halo or ($C_1$-$C_4$)alkyl, or $R^1$ and $R^2$ attached to nitrogen join together to form a 5 to 6 membered heterocycloalkyl; and $R^3$ is hydrogen, or hydroxy-($C_1$-$C_4$)alkyl.

The compound of Formula (V) includes all pharmaceutically acceptable salt forms.

In embodiments, $R^1$ and $R^2$ are hydrogen. In embodiments, one of $R^1$ and $R^2$ is hydrogen and the other is ($C_1$-$C_4$)alkyl such as methyl, ethyl, propyl, isopropyl, n-butyl or t-butyl. In embodiments, $R^1$ and $R^2$ are independently ($C_1$-$C_4$)alkyl. For example, $R^1$ and $R^2$ are independently selected from methyl, ethyl, propyl, isopropyl, n-butyl or t-butyl. In embodiments, $R^1$ and $R^2$ are methyl.

In embodiments, one of $R^1$ and $R^2$ is hydrogen and the other is phenyl, which may be optionally substituted with F, Cl, Br, or ($C_1$-$C_4$)alkyl. In embodiments, one of $R^1$ and $R^2$ is hydrogen and the other is phenyl,

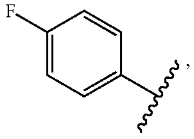, or 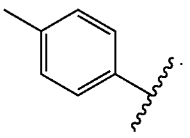.

In embodiments, $R^1$ and $R^2$ attached to nitrogen join together to form a 5 to 6 membered heterocycloalkyl such as

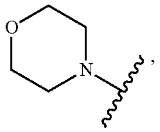, 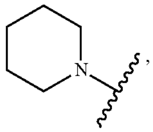, or 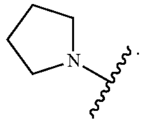.

In embodiments, $R^3$ is hydrogen. In embodiments, $R^3$ is hydroxy-$(C_1$-$C_4)$alkyl. In embodiments, $R^3$ is —$CH_2$—OH.

In embodiments, Ar is pyridyl, phenyl, naphthyl, or thiazolyl, which is optionally substituted with one or more with halo, $(C_1$-$C_4)$alkyl, $(C_1$-$C_4)$haloalkyl, —CN, —$S(O)_2$—$NH_2$, —$NH_2$, $(C_1$-$C_4)$alkoxyl, or —NHC(O)alkyl. In embodiments, Ar is

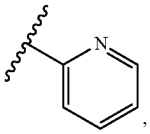, 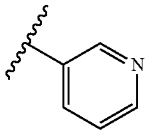, 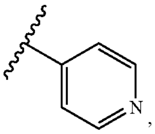,

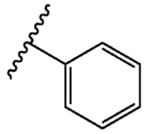, 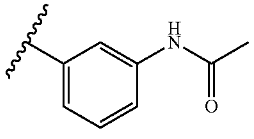,

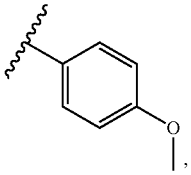, 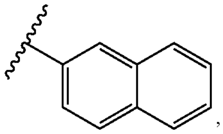,

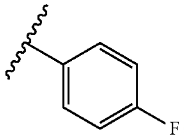, 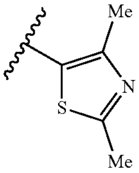, 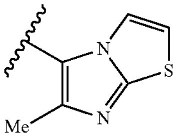,

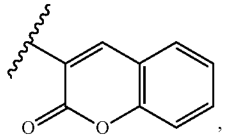, or 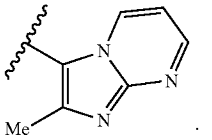.

In embodiments, the compound has the following formula:

(V-a)

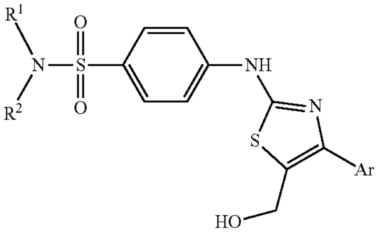 or (V-b)

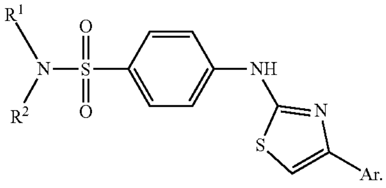

$R^1$, $R^2$ and Ar are as described herein.

In some compounds of Formula (V), when $R^1$, $R^2$ and $R^3$ are hydrogen, then Ar is not

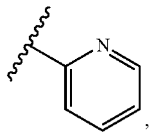, 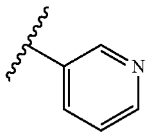, 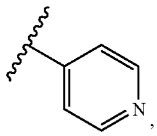,

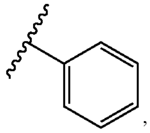, 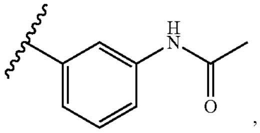,

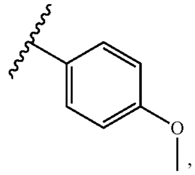, 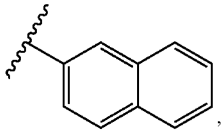,

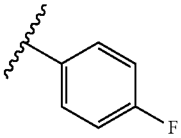, 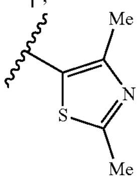, 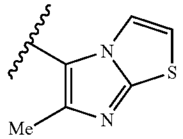,

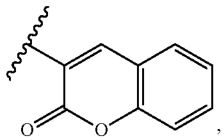, or 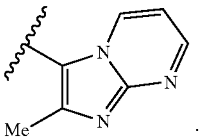.

In embodiments, the compounds of Formula (V) include:

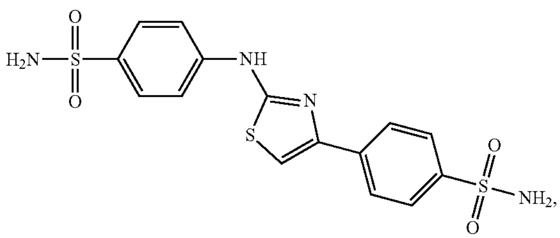,

-continued
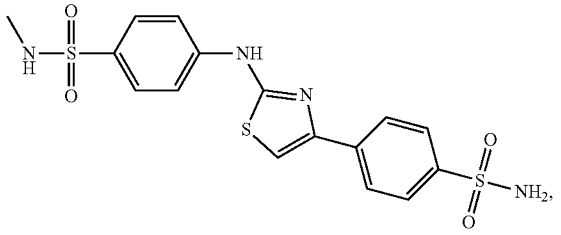
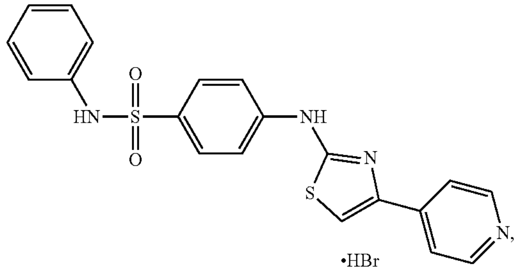
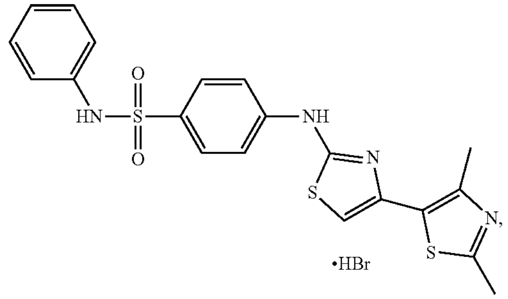
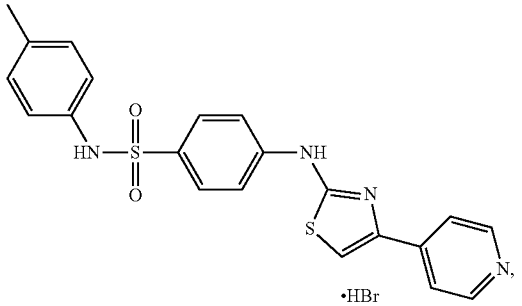
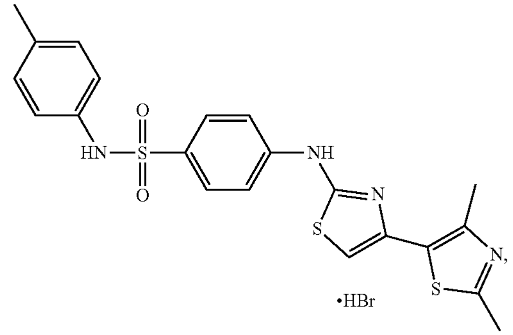
-continued
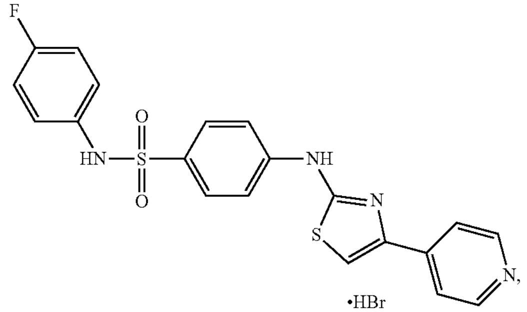
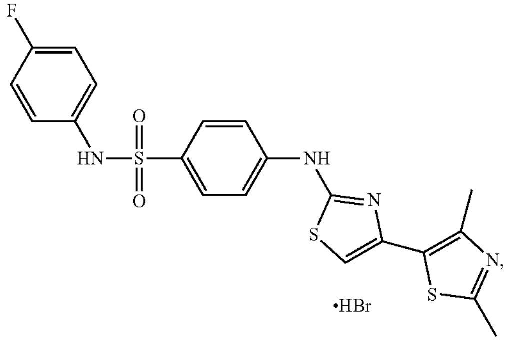
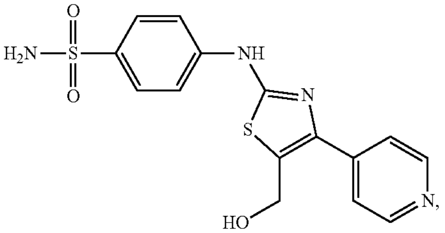
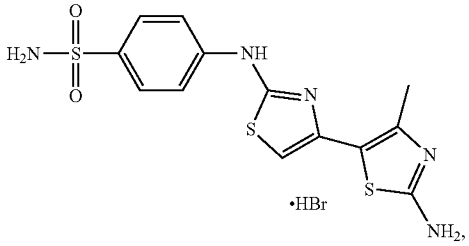
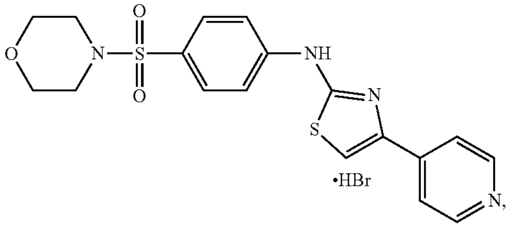
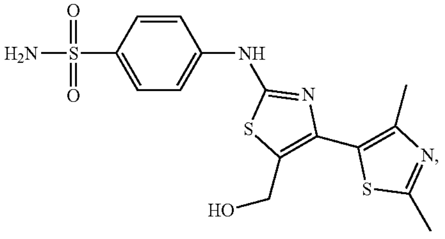

-continued
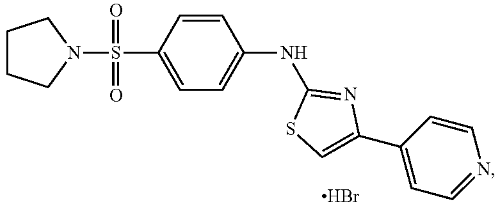
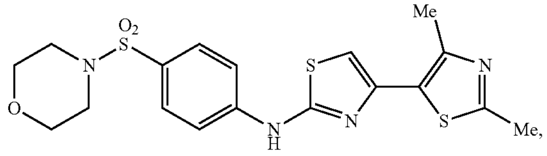
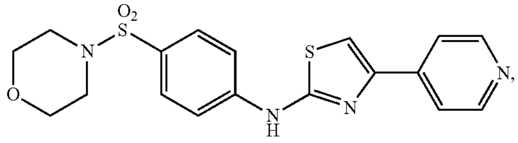
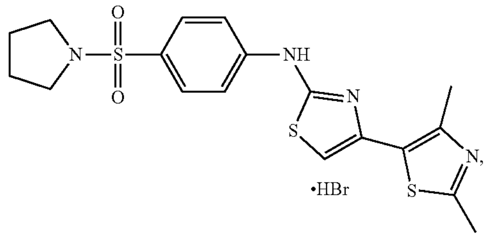
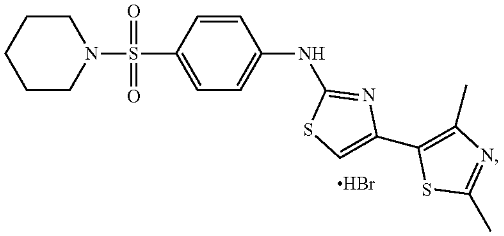
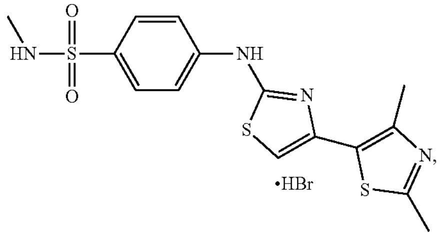
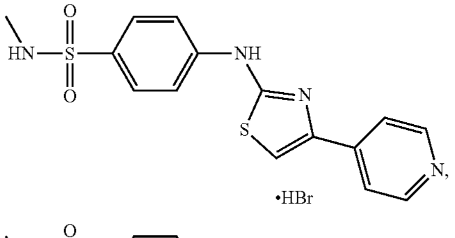
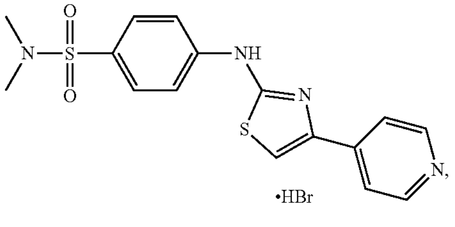
-continued
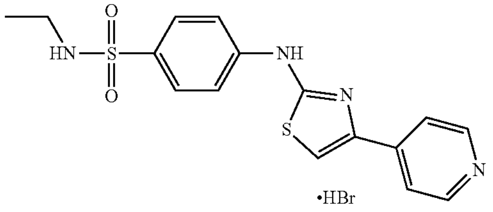
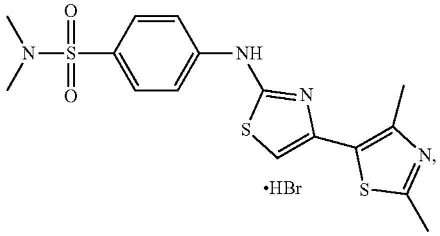
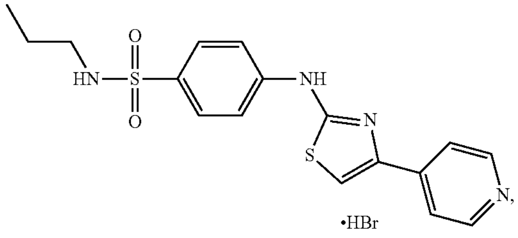
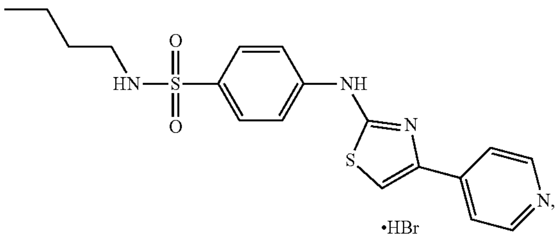
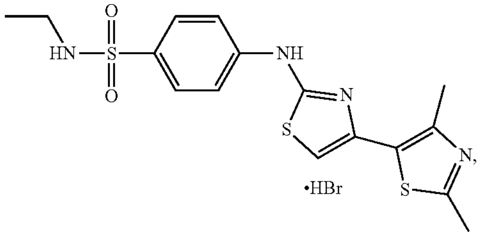
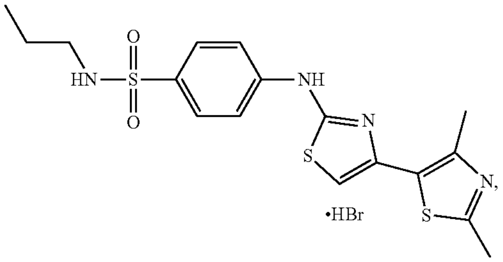
or
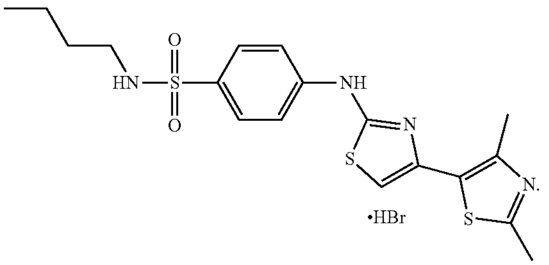

Methods

In an aspect, provided is a method for inhibiting NAD consumption and/or increasing NAD synthesis in a patient, and the method includes administering to the patient an effective dose of the compound described herein.

The compound can inhibit protein ADP-ribosylation reactions. The compound can inhibit NAD cleavage by protein deacetylases or glycohydrolases. The compound can increase NAD synthesis. The patient is afflicted with, or at risk for, a protein misfolding neurodegenerative disease or another protein misfolding disease.

The protein misfolding neurodegenerative disease includes a prion disease, Parkinson's disease or other synucleinopathies, Alzheimer's disease, amyotrophic lateral sclerosis, or a tauopathy and the protein misfolding disease includes diabetes mellitus.

In an aspect, provided is a method for preventing or inhibiting NAD depletion in a patient. In another aspect, provided is a method for improving a condition linked to alterations of NAD metabolism in a patient. The method includes administering to the patient an effective dose of the compound described herein.

The condition includes a metabolic disorder, aging, a degenerative disease, a neurodegenerative disease, neuronal degeneration associated with multiple sclerosis, hearing loss, retinal damage or multiple sclerosis, brain or cardiac ischemia, kidney failure, kidney disease, traumatic brain injury, or an axonopathy.

In an aspect, provided is a method for providing protection from toxicity of misfolded proteins in a patient. The method includes administering to the patient an effective dose of the compound described herein. The patient is afflicted with a prion disease, Parkinson's disease or other synucleinopathy, Alzheimer's disease, amyotrophic lateral sclerosis, a tauopathy or diabetes mellitus.

In an aspect, provided is a method for preventing or treating a protein misfolding neurodegenerative disease in a patient. The method includes administering to the patient an effective dose of the compound described herein. The protein misfolding neurodegenerative disease includes a prion disease, Parkinson's disease or other synucleinopathy, Alzheimer's disease, amyotrophic lateral sclerosis, or a tauopathy.

Neuroprotection and $GABA_A$ R Inhibition are Two Distinct Activities of DMCM.

DMCM, a member of the carbazole series (structure shown earlier, and in Examples), has a known mode of action: it is an inverse agonist of all subtypes of $GABA_A$ R[7], binding to its benzodiazepine (BZ) site. It is therefore a convulsant in vivo. Because convulsive activity is intolerable in a neuroprotectant, it cannot be directly repurposed[8].Another pharmacological modulator binding to the BZ site, flumazenil (Ro 15-1788)[9,10] has been tested. It neither rescued TPrP-induced toxicity nor competed with the effect of DMCM (FIG. 3), suggesting that neuroprotection is likely unrelated to intrinsic activity at $GABA_A$ R.

A pilot SAR study has been conducted to further test the conclusion that DMCM's activities, neuroprotection vs. $GABA_A$ R binding, are distinct. FIG. 4 shows the hydrazine amide 1, a close analog of DMCM (DMCM-10049), which is reported to be devoid of $GABA_A$ R activity (over 100× reduced potency for most $GABA_A$ R subtypes[11]). It showed, however, neuroprotective activity very close to that of DMCM (FIG. 4). Treatment of DMCM with diamines, including 1,4-cis-diaminocyclohexane, gave aminoamides such as compound 2 (DMCM-8137). This compound was also neuroprotective (FIG. 4). Moreover, it is designed to have a handle to permit conjugation for target identification (FIG. 4).

Taken together, these studies show that DMCM acts on a target other than $GABA_A$ R to confer neuroprotection, a finding enabling the optimization of DMCM analogs as neuroprotectants that are devoid of the activity for which the parent compound has been used. DMCM is neuroprotective in primary neurons (See FIG. 5).

DMCM Prevents Excessive Mono ADP Ribosylation Induced by TPrP.

It has been demonstrated that TPrP induces NAD depletion at least in part by excessive protein mono-ADP ribosylation[2], an NAD-consuming reaction. FIG. 6 shows that DMCM prevents this excessive protein ADP-ribosylation.

DMCM is Neuroprotective in a Cellular Model of Parkinson's Disease (PD).

Parkinson's disease, similar to prion diseases, arises from the misfolding and aggregation of a protein, α-synuclein in this case. Therefore, the neuroprotective properties of compounds from HTS were investigated in cellular models of PD-induced neurodegeneration (FIGS. 7 and 14). In these models, neuronal cells exposed to preformed alpha-synuclein fibrils (PFFs) undergo loss of synapses and dendritic spines, as well as a shortening and loss of neurites (FIG. 7, see PFFs-exposed neurons vs control neurons). PFFs-seeded neurons accumulate α-synuclein fibrils and a particular type of α-synuclein aggregates that is toxic to the cells (called pα-syn*[12]). FIG. 7 shows that the hydrazine amide of DMCM, named DMCM-10049, preserves dendritic spines in PFFs-exposed neurons and reduces the amounts of toxic pα-syn*.

Therapeutic Effect of DMCM-10049 in a Murine Model of Parkinson's Disease.

Moreover, DMCM has been used in vivo as a tool compound, with favorable PK properties[5,7-9,13,14]. Therefore, DMCM-10049 was tested in a murine model of PD (the Tg(SNCA*A53T) mice, harboring an α-synuclein mutation responsible for familial PD in humans). Treatment with DMCM-10049 significantly prolonged the survival of these mice (FIG. 8).

Therapeutic Effect of DMCM-10049 in a Murine Model of ALS.

DMCM-10049 was tested in a murine model of ALS (the Tg(SOD1*G93A) mice, harboring an SOD1 mutation[15]). Mutant SOD1 accounts for 15-20% of familial ALS and 1-2% of apparently sporadic ALS cases, and misfolded SOD1 is found in ALS patients not carrying a mutation[16]. Treatment with DMCM-10049 significantly prolonged the survival of these mice (FIG. 9).

Detailed Study of the Vatalanib Series (Aminophthalazine Series).

Vatalanib, aka SR5-1457, has recently been in late-stage clinical development as an orally administered antitumor agent[17-21]. It is a receptor tyrosine kinase inhibitor, specifically a potent VEGFR inhibitor, is highly cell-permeable and has overall excellent PK properties in humans and in rodents[22-24]. This compound was highly neuroprotective with an $EC_{50}$=39.9 nM (TPrP toxicity rescue) and $EC_{50}$=195 nM (NAD assay). Because of its high potency and excellent PK properties (including high brain penetration and high oral bioavailability), we opted to advance this compound rapidly to in vivo neuroprotection studies.

As shown in FIG. 10, vatalanib treatment of ALS mice significantly improved their motor function and muscle strength, assessed using the rotarod and hanging-wire tests.

However, a prolongation in survival times (160±2 d survival in treated animals vs 157±2 d for the control group) was not observed.

While using vatalanib for this early proof-of-concept study, this specific compound is ill-suited for direct repurposing due to its ability to strongly inhibit VEGFR, which confers the antiangiogenic effects that are thought to be responsible for its antitumor properties, which may be reasoned that the neuroprotective mode of action for this compound is unrelated to its known activity vs. VEGFR, because VEGF/VEGFR-2 signaling is known to be neuroprotective (thus blocking VEGFR would be expected to confer mild neurotoxicity rather than neuroprotection)[25]. VEGFR-2 overexpression is known to delay neurodegeneration of spinal motor neurons in Tg(SOD1*G93A) mice and VEGF administration has been shown to delay muscle weakness in ALS models[26-28] and to be neuroprotective in PD models[29,39]. Therefore, the VEGFR inhibitory activity of vatalanib should oppose the objective of neuroprotection and thus vatalanib would be a poor choice for repurposing to treat ALS or, more generally, any neurodegenerative disease that requires chronic treatment. The NAD-preserving activity identified herein likely opposes (and prevails) over the intrinsic VEGFR effects. Analogs lacking VEGFR activity should be better candidates for neuroprotective drug leads.

Analogs of vatalanib that are known to be inactive at VEGFR, or at least to have very low affinity for VEGFR, are shown in FIG. 11. Note: Flt-1 and KDR are subtypes of VEGFR, also known as VEGFR-1 and VEGFR-2, respectively. As shown, the activity of these compounds with respect to their neuroprotective/NAD-restoring effects does not correlate with their activity for VEGFR inhibition[24]. For example, a methyl ketone-containing structural analog of vatalanib, SR1-134005 ($2^{nd}$ structure, FIG. 11), is more than 6-fold more potent than is vatalanib as a neuroprotective agent (6.3 nM vs. 39.9 nM), though this same compound is 13-fold less potent than vatalanib as a VEGFR-1 inhibitor (1 μM vs. 77 nM). Similarly, the analog SR1-151915 ($3^{rd}$ structure) retains about half of vatalanib's neuroprotective activity ($EC_{50}$=71.4 nM) but this same compound is also a poor VEGFR inhibitor ($IC_{50}$>1 μM). Conversely, analog SR1-151911 (4th structure) is far less neuroprotective (only 44% neuroprotection @ 6.4 μM) though it has modest VEGFR activity ($IC_{50}$=793 nM vs. VEGFR-1, only ~20-fold less than vatalanib and more potent at VEGFR than are SR1-134005 and SR1-151915).

Further, other commercially available potent VEGFR inhibitors structurally unrelated to vatalanib (lenvatinib, pazopanib, tivozanib & sorafenib) entirely lacked neuroprotective activity in the TPrP assay at concentrations up to 10 μM (data not shown).

Clearly the two activities (neuroprotection and antitumor effects through VEGFR inhibition) can be differentiated, and this unambiguous result prompted us to test the vatalanib analog SR1-134005, having low VEGF-R activity, in an ALS mouse model.

Therapeutic Effect of SR1-134005 in a Murine Model of ALS.

The methyl ketone analog of vatalanib SR1-134005 (exhibiting ~13-fold reduced VEGFR-1 activity relative to vatalanib, FIG. 11) provides the same overall in vivo benefit as does vatalanib, and moreover it is efficacious at an 8-fold lower dose (FIG. 12). This in vivo result supports our in vitro findings that SR1-134005 is a more potent neuroprotectant than is vatalanib and further that neuroprotection is dissociated from VEGFR inhibition, which is presumed to be responsible for the antitumor effects seen for this class of compounds.

Therapeutic Effect of SR1-134005 in a Murine Model of Parkinson's Disease.

Treatment with the methyl ketone analog of vatalanib SR1-134005 significantly prolonged the survival of Tg(SNCA*A53T) mice (FIG. 13).

Neuroprotective Effect of Pyrazolopyrimidines (SR1-293229), Aminothiazoles (SR1-477186), Triazolophthalazines (SR1-115259), Aminophthalazines (Vatalanib) and Flavonoids (Nobiletin, Apigenin) in a Cellular Model of PD, a Synucleinopathy.

Similar to our observations with the carbazole series, compounds of other leads series protected against neurodegeneration induced by α-synuclein PFFs in cultured neurons. These include the pyrazolopyrimidines (SR1-293229), aminothiazoles (SR1-477186), triazolophthalazines (SR1-115259), aminophthalazines (vatalanib) and flavonoids (nobiletin, apigenin). FIG. 14 illustrates the protective effect and shows that the lead compounds prevent loss of neurites induced by PFFs exposure.

NAD Rescue by the Carbazole, Aminophthalazine, Pyrazolopyrimidine, Triazolophtalazine and Flavonoid Series is Not Due to PARP-1 Inhibition.

FIG. 15 shows that at least five of the lead series described herein are not PARP-1 inhibitors.

Aminophthalazines (Vatalanib and SR1-134005) are NAMPT Activators.

It has been demonstrated that TPrP induces excessive ADP-ribosylation and designed the compound screening strategy to capture compounds able to restore physiological NAD levels. FIG. 6 shows that this can be achieved by preventing excessive ADP-ribosylation. FIG. 16 shows that it can also be achieved by enhancing NAD synthesis since one of our lead series, the aminophthalazines vatalanib and "SR-005" acts by activating NAMPT, the rate-limiting enzyme in NAD synthesis.

For the first time, it has been shown that failure of NAD metabolism is a fundamental mechanism of neurotoxicity induced by a misfolded amyloidogenic protein (TPrP), and that NAD replenishment is neuroprotective[2]. Therefore, NAD-restorative compounds were screened for rescue from proteotoxicity, with the hypothesis that other conditions may be successfully treated using compounds that can restore healthy NAD levels, by any mechanism. Indeed, NAD dysregulation is now also recognized as being involved in AD[31,32], aging[33-36], neuronal degeneration associated with multiple sclerosis[37], hearing loss[38], retinal damage[39], traumatic brain injury[40], and axonopathy[41]. Substantial decreases in NAD levels are found in degenerative renal conditions[42]. NAD augmentation such as NAD administration or increased NAD synthesis by enzyme overexpression has been shown to mitigate brain ischemia[43], cardiac ischemia/reperfusion injury[44,45] and acute kidney injury[42].

NAD metabolism has also been shown to be altered in murine models of type 2 diabetes (T2D)[46,47]. Alterations of NAD metabolism in diabetes can be explained by our findings that misfolded proteins induce NAD dysregulation. Indeed, diabetes has been shown to be a protein misfolding disease, characterized by pancreatic beta-cell dysfunction and death, concomitant with the deposition of aggregated islet amyloid polypeptide (IAPP), a protein co-expressed and secreted with insulin by pancreatic beta-cells[48]. Amyloid IAPP deposition is a common feature of diabetes of different etiologies'. Similarly to proteins involved in other protein misfolding diseases, IAPP forms toxic oligomers[48].

Moreover, proinsulin, the precursor of insulin, is also prone to misfold in beta-cells. Misfolding of proinsulin has been linked to type 2, type 1 and some monogenic forms of diabetes progression[48,50,51]. Finally, pancreatic beta cells harbor some common physiological properties with neurons[52]. The compounds described herein will therefore also be used to mitigate dysfunction and death of pancreatic cells in cellular models of diabetes, and to achieve therapeutic benefits in animal models of diabetes, as a demonstration of their potential for the treatment of diabetes mellitus in humans. To this end, we will use rodent derived insulin-secreting cell lines such as MIN-6 and INS-1 cells[52,53]; we expect alterations of their beta cell function, NAD levels and viability upon exposure to misfolded and/or aggregated forms of IAPP and/or proinsulin. Further, we expect that such alterations will be corrected by treatment with the compounds described herein. Therapeutic benefits of the compounds will be assessed in rodent models such as, for example, high fat fed mice, ob/ob mice and db/db mice (leptin deficient and resistant, respectively) for T2D[54], and streptozotoxin-treated mice, non-obese diabetic (NOD) mice, BioBreeding diabetes-prone (BB) rat for type 1 diabetes[55,56].

NAD, as used here, designates both the oxidized (NAD+) and the reduced (NADH) forms of the cofactor. NAD is critical, inter alia, as a co-enzyme for the regulation of energy metabolism pathways such as glycolysis, TCA cycle and oxidative phosphorylation leading to ATP production. In addition, NAD serves as a substrate for signal transduction and post-translational protein modifications called ADP-ribosylations.

Physiological cellular NAD levels result from the balance of activity of NAD synthesis enzymes and NAD consuming enzymes, which may be reasoned that the NAD imbalance induced by misfolded proteins (and that is assessed in our phenotypic assays) could therefore result from either impaired NAD biosynthesis or from increased NAD consumption.

In mammalian cells, NAD is mainly synthesized via the salvage pathway using the precursor nicotinamide (NAM). The rate-limiting enzyme for NAD synthesis in the salvage pathway is nicotinamide phosphoribosyltransferase (NAMPT). Other NAD synthesis pathways are the de novo pathway utilizing the precursor tryptophan and the Preiss-Handler pathway utilizing the precursor nicotinic acid (NA).

On the other hand, NAD is consumed during the following cellular reactions: 1) the production of calcium-releasing second messengers cyclic ADP-ribose (cADPR) and ADP-ribose (ADPR) from NAD by enzymes called NAD hydrolases or ADP-ribosyl cyclases (CD38 and CD157); 2) sirtuin-mediated protein deacetylations, and 3) protein ADP-ribosylations, in which one or several ADP-ribose moiety of NAD is transferred unto proteins by mono/oligo-ADP-ribose transferases (mARTs) or poly-ADP ribose transferases (called PARPs).

It has been showed that TPrP induced excessive ADP-ribosylation of cellular proteins, and further that toxicity was not alleviated by selective PARP1 inhibitors. Therefore, these studies unveiled a new mechanism of neurotoxicity linked to an imbalance in NAD metabolism due, at least in part, to excessive mono or oligo ADP-ribosylation reactions. As mentioned above, the HTS campaign and follow-up assays that led to the identification of the 8 compound series presented herein rely upon phenotypic readouts, and the study was thus purposefully agnostic of the mechanism underlying preservation of NAD levels and viability in cells exposed to proteotoxicity. This design was intended to identify compounds regulating NAD levels by any mechanism of action such as enhancing NAD synthesis or preventing excessive NAD degradation/consumption, and to include non-PARP1 inhibitors. Our data show that: 1) all the protective compounds presented herein are neuroprotective and preserve cellular NAD levels; 2) at least 5 of these compounds are not PARP-1 inhibitors (FIG. 15); 3) as proof-of-concept, at least one test compound prevents excessive ADP-ribosylation induced by a misfolded protein (FIG. 6), and at least one test compound is a NAMPT activator (FIG. 16).

EXAMPLES

Example 1: Cell Viability Assays and NAD Quantification Assays

The tables below show the structures of specific examples of compounds useful for practice of methods of the invention, associated with corresponding data such as compound identifier, molecular weight, compound properties, and biological results.

The biological activity of test compounds was quantified in two assays: a cell viability assay (CellTiter-Glo®) assessing the ability of compounds to prevent neuronal death induced by the misfolded protein TPrP, and a NAD quantification assay (NAD+/NADH-Glo™) assessing the ability of compounds to prevent NAD depletion induced by the misfolded protein TPrP. Efficacious concentrations ($EC_{50}$ values) are shown. The procedures were as described in FIG. 2 (1536 well-plate format) for those compounds where both viability $EC_{50}$ and NAD $EC_{50}$ are indicated (Tables 1-8), as described in FIG. 4 (96 well-plate format) for those compounds where only viability $EC_{50}$ is indicated (Tables 9-12).

TABLE 1

Triazolophthalazines: SR1-115259 series

| Structure | identifier, properties | Viability $EC_{50}$ | NAD $EC_{50}$ |
|---|---|---|---|
| 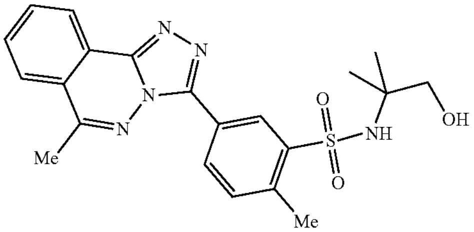 [SMILES: Cc1ccc(-c2nnc3c4ccccc4c(C)nn23)cc1S(=O)(=O)NC(C)(C)CO] | SR1-115259<br>Mol. Wt. = 425<br>HBD = 2<br>HBA = 5<br>tPSA = 107 | 5.1 nM | 167 nM |

TABLE 1-continued

Triazolophthalazines: SR1-115259 series

| Structure | identifier, properties | Viability $EC_{50}$ | NAD $EC_{50}$ |
|---|---|---|---|
| 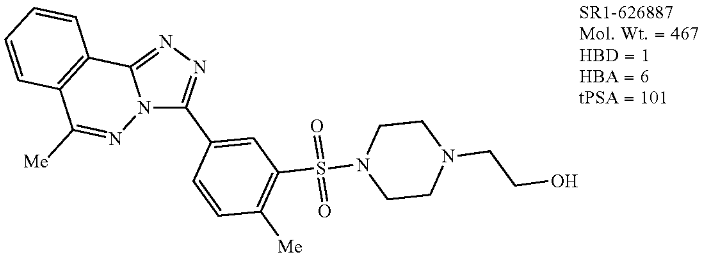 | SR1-626887<br>Mol. Wt. = 467<br>HBD = 1<br>HBA = 6<br>tPSA = 101 | <3 nM | 9.1 nM |
| 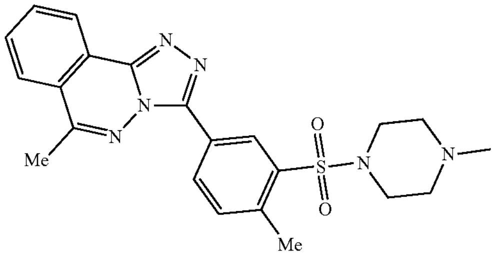 [SMILES: Cc1ccc(-c2nnc3c4ccccc4c(C)nn23)cc1S(=O)(=O)N1CCN(C)CC1] | SR1-115275<br>Mol. Wt. = 437<br>HBD = 0<br>HBA = 6<br>tPSA = 81 | 839 nM | 2.6 μM |
| 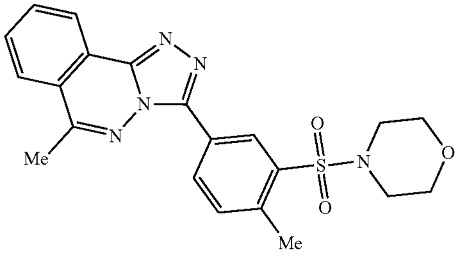 [SMILES: Cc1ccc(-c2nnc3c4ccccc4c(C)nn23)cc1S(=O)(=O)N1CCOCC1] | SR5-22843<br>Mol. Wt. = 423<br>HBD = 0<br>HBA = 6<br>tPSA = 87 | 30 nM | 219 nM |
| 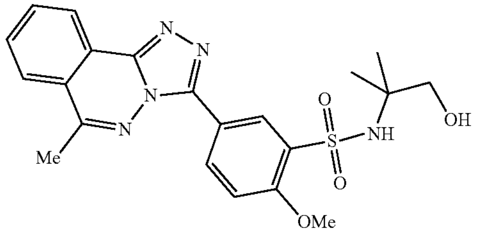 [SMILES: COc1ccc(-c2nnc3c4ccccc4c(C)nn23)cc1S(=O)(=O)NC(C)(C)CO] | SR1-87819<br>Mol. Wt. = 442<br>HBD = 2<br>HBA = 6<br>tPSA = 116 | 98 nM | 682 nM |
| 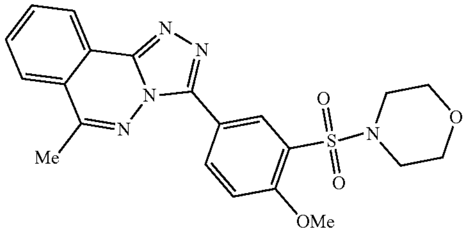 [SMILES: COc1ccc(-c2nnc3c4ccccc4c(C)nn23)cc1S(=O)(=O)N1CCOCC1] | SR5-22837<br>Mol. Wt. = 439<br>HBD = 0<br>HBA = 7<br>tPSA = 96 | 29 nM | 89 nM |
| 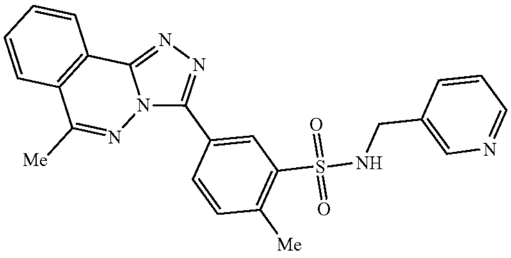 [SMILES: Cc1ccc(-c2nnc3c4ccccc4c(C)nn23)cc1S(=O)(=O)NCc1cccnc1] | SR5-22839<br>Mol. Wt. = 445<br>HBD = 1<br>HBA = 6<br>tPSA = 99 | 28 nM | 92 nM |

TABLE 1-continued

| Triazolophthalazines: SR1-115259 series | | | |
|---|---|---|---|
| Structure | identifier, properties | Viability $EC_{50}$ | NAD $EC_{50}$ |
| 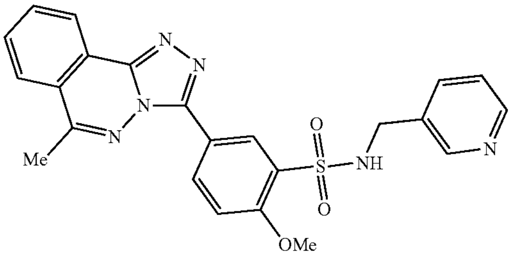 [SMILES: COc1ccc(-c2nnc3c4ccccc4c(C)nn23)cc1S(=O)(=O)NCc1cccnc1] | SR5-22838<br>Mol. Wt. = 461<br>HBD = 1<br>HBA = 7<br>tPSA = 108 | 90 nM | 380 nM |
| 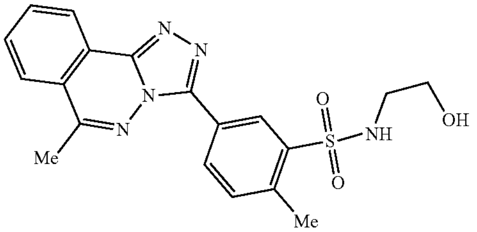 [SMILES: Cc1ccc(-c2nnc3c4ccccc4c(C)nn23)cc1S(=O)(=O)NCCO] | SR1-87813<br>Mol. Wt. = 397<br>HBD = 2<br>HBA = 5<br>tPSA = 107 | 156 nM | 733 nM |
| 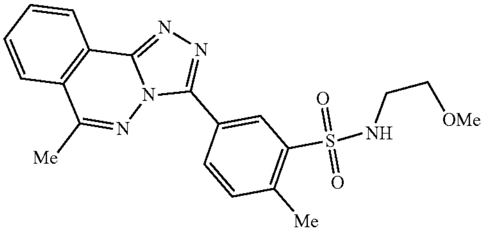 [SMILES: COCCNS(=O)(=O)c1cc(-c2nnc3c4ccccc4c(C)nn23)ccc1C] | SR5-22841<br>Mol. Wt. = 411<br>HBD = 1<br>HBA = 6<br>tPSA = 96 | 130 nM | 688 nM |
| 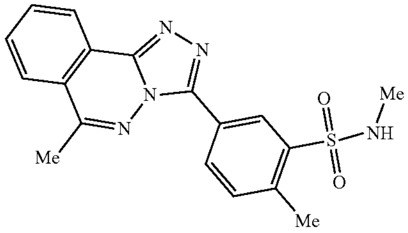 [SMILES: CNS(=O)(=O)c1cc(-c2nnc3c4ccccc4c(C)nn23)ccc1C] | SR1-115255<br>Mol. Wt. = 367<br>HBD = 1<br>HBA = 5<br>tPSA = 86 | 196 nM | 1.2 μM |

TABLE 2

| Pyrazolopyrimidines: SR1-293229 and related compounds | | | |
|---|---|---|---|
| Structure | Data | Viability $EC_{50}$ | NAD $EC_{50}$ |
| 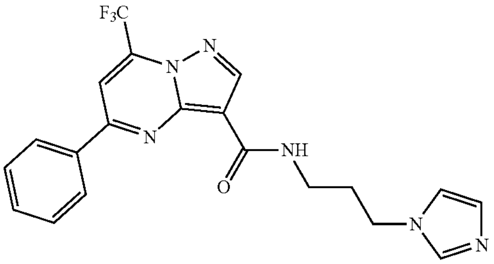 [SMILES: O=C(NCCCn1ccnc1)c1cnn2c(C(F)(F)F)cc(-c3ccccc3)nc12] | SR1-293229<br>Mol. Wt: 414<br>cLog P: 3.0<br>HBD = 1<br>HBA = 4<br>tPSA = 73 | 1.9 nM | 6.8 nM |

TABLE 2-continued

| Pyrazolopyrimidines: SR1-293229 and related compounds | | | |
|---|---|---|---|
| Structure | Data | Viability $EC_{50}$ | NAD $EC_{50}$ |
| 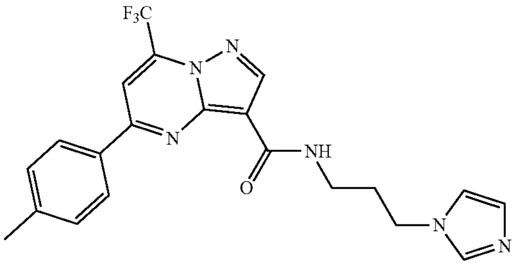 [SMILES: Cc1ccc(-c2cc(C(F)(F)F)n3ncc(C(=O)NCCCn4ccnc4)c3n2)cc1] | SR1-527764<br>Mol. Wt: 428<br>cLog P: 3.5<br>HBD = 1<br>HBA = 4<br>tPSA = 73 | 1.9 nM | 7.1 nM |
| 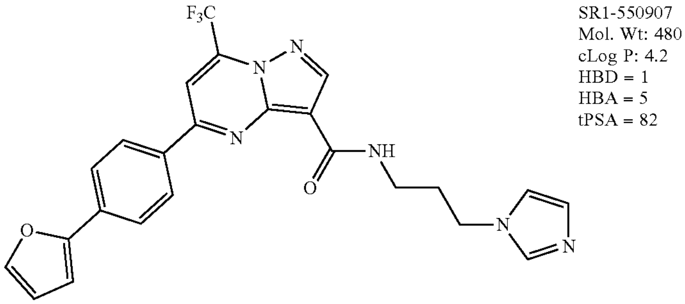 | SR1-550907<br>Mol. Wt: 480<br>cLog P: 4.2<br>HBD = 1<br>HBA = 5<br>tPSA = 82 | 2.9 nM | 9.7 nM |
| 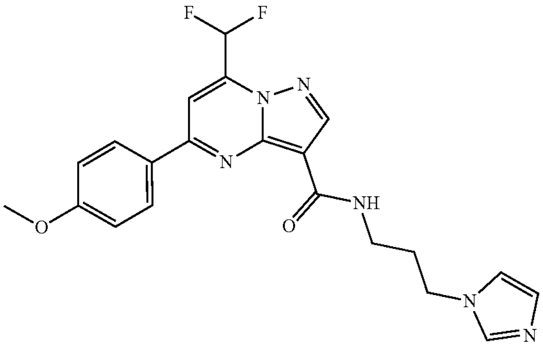 [SMILES: COc1ccc(-c2cc(C(F)F)n3ncc(C(=O)NCCCn4ccnc4)c3n2)cc1] | SR0-24089<br>Mol. Wt: 426<br>cLog P: 2.2<br>HBD = 1<br>HBA = 5<br>tPSA = 82 | fully effective at 1 nM, partially effective at 0.2 nM | nt |
| 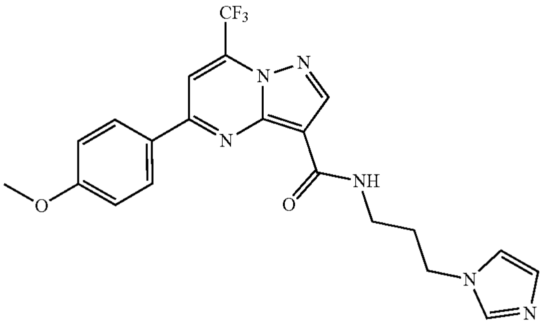 [SMILES: COc1ccc(-c2cc(C(F)(F)F)n3ncc(C(=O)NCCCn4ccnc4)c3n2)cc1] | SR0-24081<br>Mol. Wt: 444<br>cLog P: 3.0<br>HBD = 1<br>HBA = 5<br>tPSA = 82 | fully effective at 1 nM | nt |

TABLE 2-continued

| Pyrazolopyrimidines: SR1-293229 and related compounds | | | |
|---|---|---|---|
| Structure | Data | Viability $EC_{50}$ | NAD $EC_{50}$ |
| 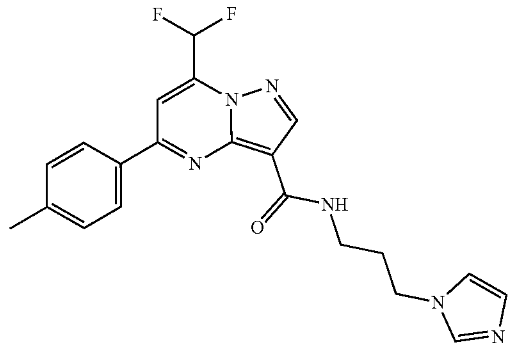 [SMILES: Cc1ccc(-c2cc(C(F)F)n3ncc(C(=O)NCCCn4ccnc4)c3n2)cc1] | SR-024088<br>Mol. Wt: 410<br>cLog P: 2.7<br>HBD = 1<br>HBA = 4<br>tPSA = 73 | >80% effective at 1 nM | nt |
| 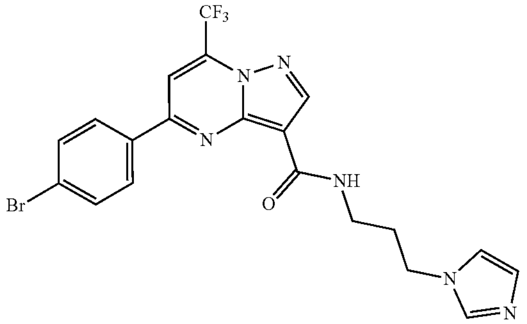 [SMILES: O=C(NCCCn1ccnc1)c1cnn2c(C(F)(F)F)cc(-c3ccc(Br)cc3)nc12] | SR0-24082<br>Mol. Wt: 493<br>cLog P: 3.8<br>HBD = 1<br>HBA = 4<br>tPSA = 73 | ~40% effective at nM, fully effective at 10 nM | nt |
| 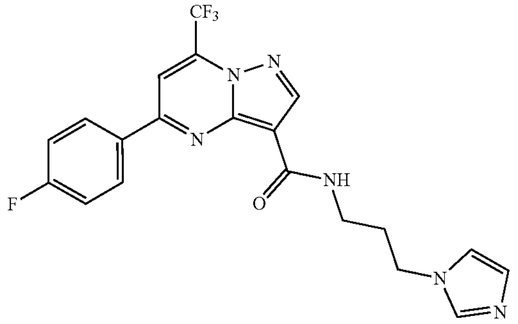 [SMILES: O=C(NCCCn1ccnc1)c1cnn2c(C(F)(F)F)cc(-c3ccc(F)cc3)nc12] | SR0-24083<br>Mol. Wt: 432<br>cLog P: 3.1<br>HBD = 1<br>HBA = 4<br>tPSA = 73 | ~40% effective at 1 nM, fully effective at 10 nM | nt |
| 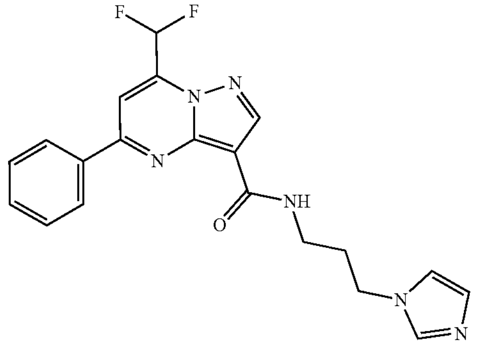 [SMILES: O=C(NCCCn1ccnc1)c1cnn2c(C(F)F)cc(-c3ccccc3)nc12] | SR0-24084<br>Mol. Wt: 396<br>cLog P: 2.2<br>HBD = 1<br>HBA = 4<br>tPSA = 73 | ~40% effective at 1 nM, fully effective at 10 nM | nt |

TABLE 2-continued

| Pyrazolopyrimidines: SR1-293229 and related compounds | | | |
|---|---|---|---|
| Structure | Data | Viability $EC_{50}$ | NAD $EC_{50}$ |
| 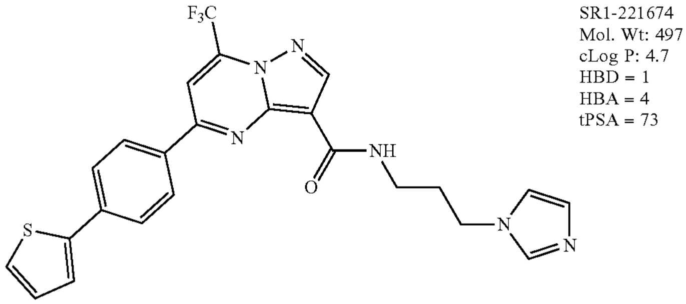 | SR1-221674<br>Mol. Wt: 497<br>cLog P: 4.7<br>HBD = 1<br>HBA = 4<br>tPSA = 73 | fully effective at 10 nM, ineffective at 1 nM | nt |

TABLE 3

| Aminophthalazines: Vatalanib and related compounds | | | |
|---|---|---|---|
| Structure | identifier | Viability $EC_{50}$ | NAD $EC_{50}$ |
| 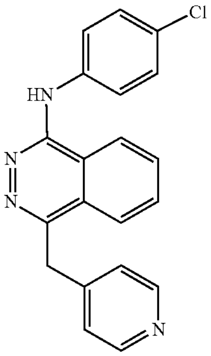 [SMILES: Clc1ccc(Nc2nnc(Cc3ccncc3)c3ccccc23)cc1] | Vatalanib<br>SR5-1457 | 40 nM | 195 nM |
| 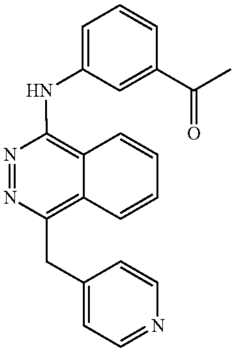 [SMILES: CC(=O)c1cccc(Nc2nnc(Cc3ccncc3)c3ccccc23)c1] | SR1-134005 | 6.3 nM | 105 nM |

TABLE 3-continued

| Aminophthalazines: Vatalanib and related compounds | | | |
|---|---|---|---|
| Structure | identifier | Viability $EC_{50}$ | NAD $EC_{50}$ |
| 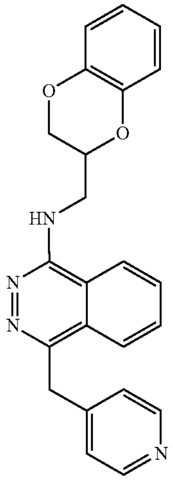 [SMILES: c1ccc2c(c1)OCC(CNc1nnc(Cc3ccncc3)c3ccccc13)O2] | SR1-134003 | 200 nM | 1.2 µM |
| 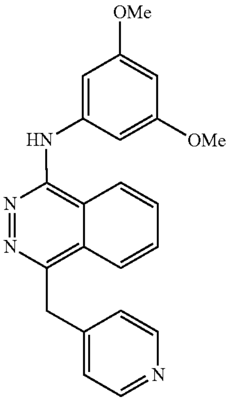 [SMILES: COc1cc(Nc2nnc(Cc3ccncc3)c3ccccc23)cc(OC)c1] | SR1-151915 | 71.4 nM | 280 nM |

TABLE 4
| Carbazoles: DMCM and related compounds | | | |
|---|---|---|---|
| Structure | identifier | Viability $EC_{50}$ | NAD $EC_{50}$ |
| 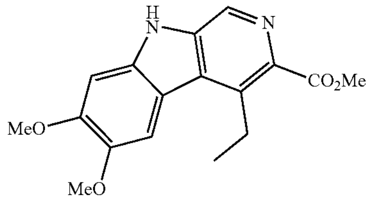 [SMILES: CCc1c(C(=O)OC)ncc2[nH]c3cc(OC)c(OC)cc3c12] | SR1-75869, aka DMCM | 120 nM | 749 nM |
| 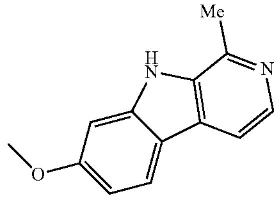 [SMILES: COc1ccc2c(c1)[nH]c1c(C)nccc12] | SR5-1527, aka methoxy harman | 1.8 μM | 14 μM |
| 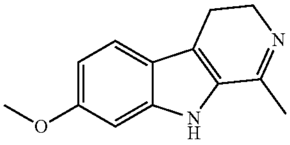 | SR1-721899, aka harmaline | 3.8 μM | 14 μM |
| 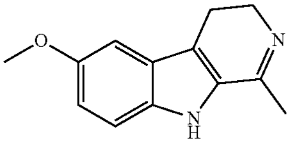 | SR1-841225, aka 6-methoxy harmaline | 3.3 μM | >15 μM |
| 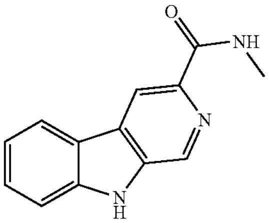 [SMILES: CNC(=O)c1cc2c(cn1)[nH]c1ccccc12] | SR1-75632, aka N-methyl-9H-pyrido[3,4-b]indole-3-carboxamide | 3.2 μM | >15 μM |
| 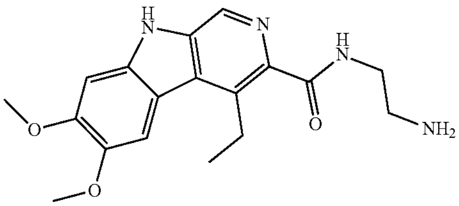 [SMILES: CCc1c(C(=O)NCCN)ncc2[nH]c3cc(OC)c(OC)cc3c12] | DMCM-8124 | ~1.8 μM | nt |
| 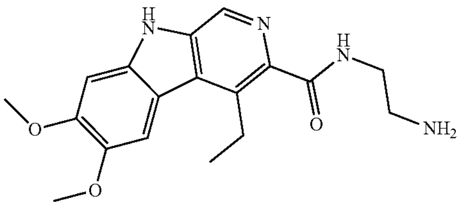 [SMILES: CCc1c(C(=O)NCCN)ncc2[nH]c3cc(OC)c(OC)cc3c12] | DMCM-8130 | ~600 nM | nt |

TABLE 4-continued
| Carbazoles: DMCM and related compounds | | | |
|---|---|---|---|
| Structure | identifier | Viability $EC_{50}$ | NAD $EC_{50}$ |
| 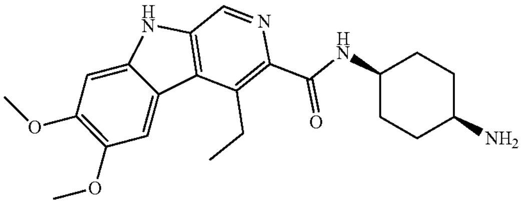 [SMILES: CCc1c(C(=O)N[C@H]2CC[C@@H](N)CC2)ncc2[nH]c3cc(OC)c(OC)cc3c12] | DMCM-8137 | ~500 nM | nt |
| 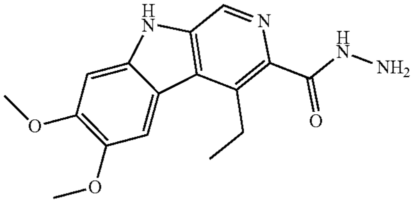 [SMILES: CCc1c(C(=O)NN)ncc2[nH]c3cc(OC)c(OC)cc3c12] | DMCM-10049 | ~500 nM | nt |
TABLE 5
| Aminothiazoles: SR1-477186 and related compounds | | | |
|---|---|---|---|
| Structure | identifier | Viability $EC_{50}$ | NAD $EC_{50}$ |
| 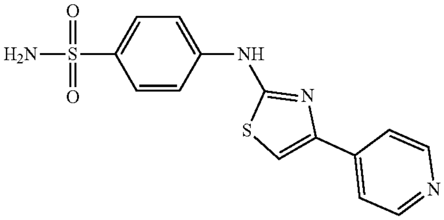 [SMILES: NS(=O)(=O)c1ccc(Nc2nc(-c3ccncc3)cs2)cc1] | SR1-477186 | 26 nM | 365 nM |
| 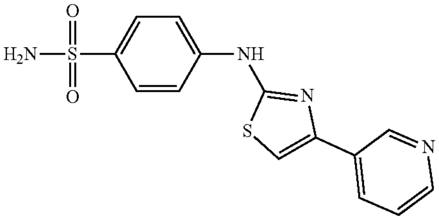 | SR1-809850 | 88 nM | 337 nM |
| 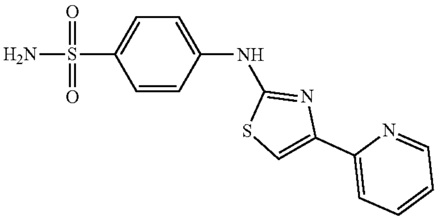 | SR1-477176 | 227 nM | 891 nM |
| 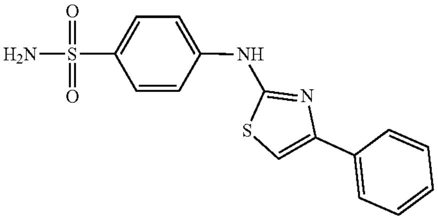 [SMILES: NS(=O)(=O)c1ccc(Nc2nc(-c3cccnc3)cs2)cc1] | SR1-492469 | 311 nM | 859 nM |

TABLE 5-continued
| Aminothiazoles: SR1-477186 and related compounds | | | |
|---|---|---|---|
| Structure | identifier | Viability $EC_{50}$ | NAD $EC_{50}$ |
| 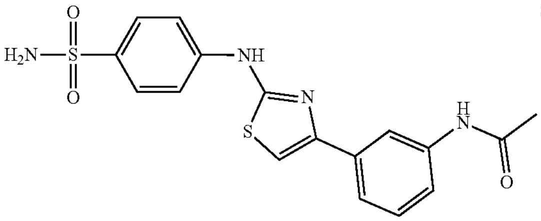 [SMILES: CC(=O)Nc1cccc(-c2csc(Nc3ccc(S(N)(=O)=O)cc3)n2)c1] | SR1-364643 | 53 nM | 263 nM |
| 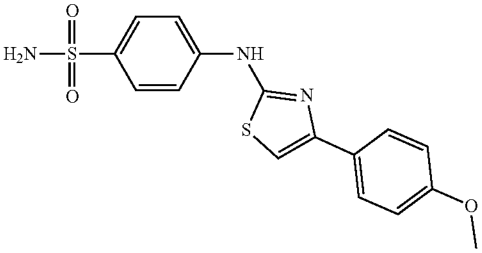 [SMILES: COc1ccc(-c2csc(Nc3ccc(S(N)(=O)=O)cc3)n2)cc1] | SR1-223735 | 87 nM | 360 nM |
| 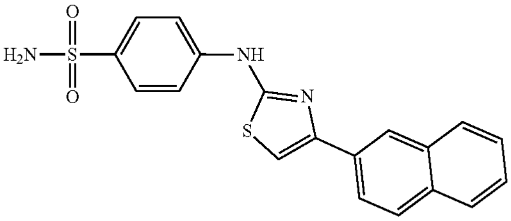 [SMILES: NS(=O)(=O)c1ccc(Nc2nc(-c3ccc4ccccc4c3)cs2)cc1] | SR1-281377 | 192 nM | 1.2 μM |
| 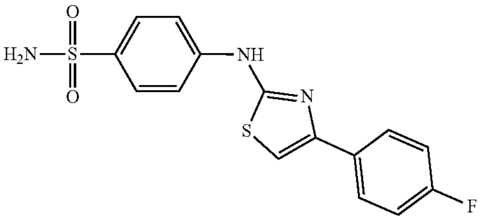 [SMILES: NS(=O)(=O)c1ccc(Nc2nc(-c3ccc(F)cc3)cs2)cc1] | SR1-742242 | 197 nM | 946 nM |
| 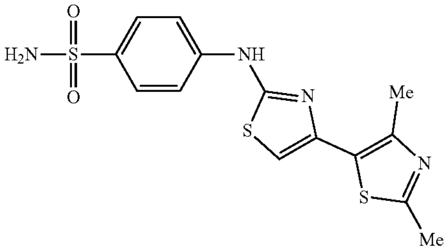 [SMILES: Cc1nc(C)c(-c2csc(Nc3ccc(S(N)(=O)=O)cc3)n2)s1] | SR1-477302 | 14 nM | 103 nM |
| 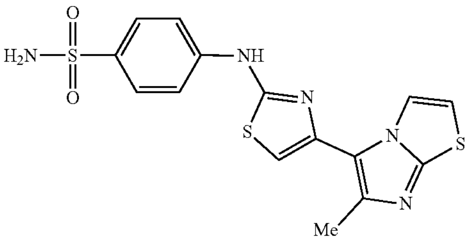 [SMILES: Cc1nc2sccn2c1-c1csc(Nc2ccc(S(N)(=O)=O)cc2)n1] | SR1-477230 | 47 nM | 204 nM |

TABLE 5-continued

| Aminothiazoles: SR1-477186 and related compounds | | | |
|---|---|---|---|
| Structure | identifier | Viability $EC_{50}$ | NAD $EC_{50}$ |
| 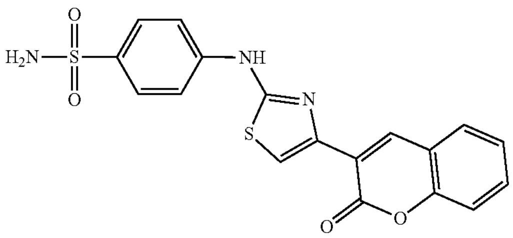 [SMILES: NS(=O)(=O)c1ccc(Nc2nc(-c3cc4ccccc4oc3=O)cs2)cc1] | SR1-22833 | 57 nM | 245 nM |
| 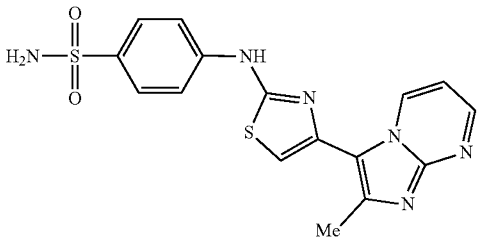 [SMILES: Cc1nc2ncccn2c1-c1csc(Nc2ccc(S(N)(=O)=O)cc2)n1] | SR1-477264 | 155 nM | 597 nM |

TABLE 6

| Flavonoids Nobiletin and related compounds | | | |
|---|---|---|---|
| Structure | Data | Viability $EC_{50}$ | NAD $EC_{50}$ |
| 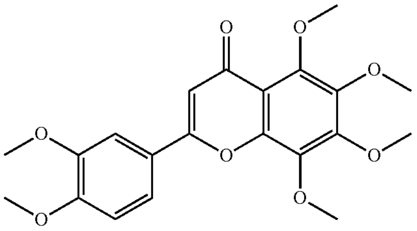 | SR-01000712262, aka nobiletin, aka 2-(3,4-dimethoxy phenyl)-5,6,7,8-tetramethoxy-4H-chromen-4-one | 580 nM | 664 nM |
| 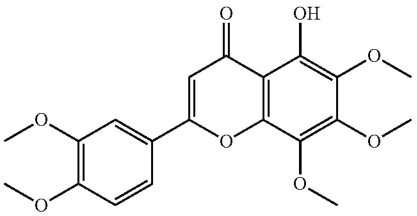 | SR-05000002635, aka 5-demethyl nobiletin, aka 2-(3,4-dimethoxy phenyl)-5-hydroxy-6,7,8-trimethoxy-4H-chromen-4-one | 81 nM | 609 nM |
| 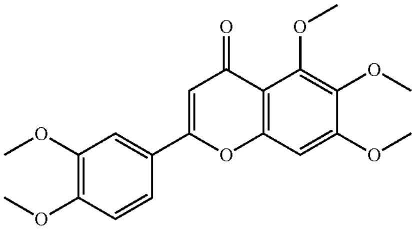 | SR-05000002257, aka sinensetin, aka 2-(3,4-dimethoxy phenyl)-5,6,7-trimethoxy-4H-chromen-4-one | 323 nM | 3.6 μM |

TABLE 6-continued

| Flavonoids Nobiletin and related compounds | | | |
| --- | --- | --- | --- |
| Structure | Data | Viability $EC_{50}$ | NAD $EC_{50}$ |
| 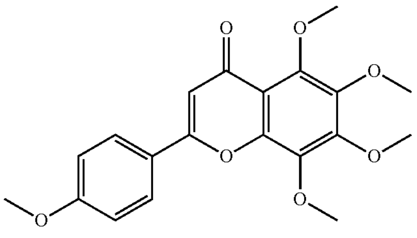 | SR-05000002625, aka tangeretin, aka 5,6,7,8-tetramethoxy-2-(4-methoxyphenyl)-4H-chromen-4-one | 1.9 μM | 6.0 μM |
| 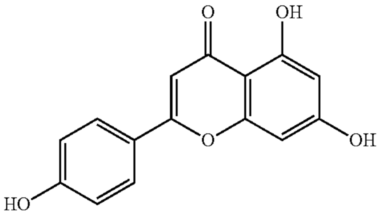 [SMILES: O=c1cc(-c2ccc(O)cc2)oc2cc(O)cc(O)c12] | SR1-75663, aka apigenin, aka 5,7-dihydroxy-2-(4-hydroxyphenyl)-4H-chromen-4-one | 1.7 μM | >10 μM |
| 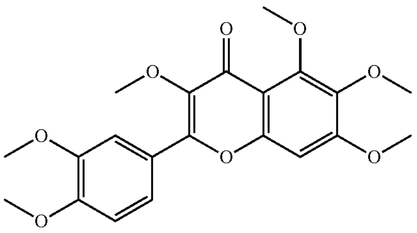 | SR5-2644, aka quercetagetin hexamethyl ether, aka 2-(3,4-dimethoxyphenyl)-3,5,6,7-tetramethoxy-4H-chromen-4-one | 620 nM | 1.2 μM |
| 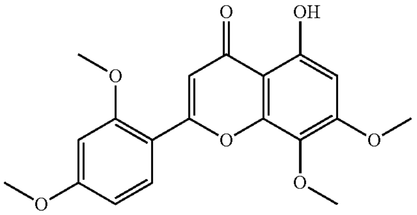 | SR5-2616, aka 2-(2,4-dimethoxy phenyl)-5-hydroxy-7,8-dimethoxy-4H-chromen-4-one | 1.6 μM | 2.1 μM |
| 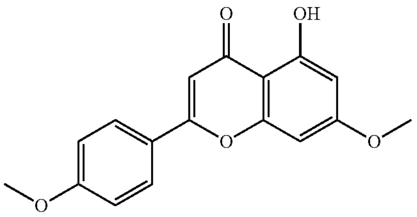 | SR5-2549, aka 7,4'-di-O-methylapigenin, aka 5-hydroxy-7-methoxy-2-(4-methoxyphenyl)-4H-chromen-4-one | 2.0 μM | 7.3 μM |
| 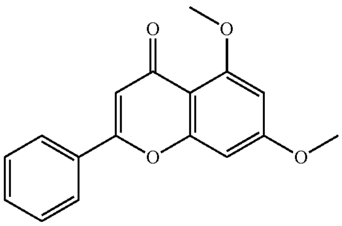 [SMILES: COc1cc(OC)c2c(=O)cc(-c3ccccc3)oc2c1] | SR1-758978, aka chrysin dimethyl ether, aka 5,7-dimethoxy-2-phenyl-4H-chromen-4-one | 1.7 μM | >10 μM |

TABLE 6-continued
| Flavonoids Nobiletin and related compounds | | | |
|---|---|---|---|
| Structure | Data | Viability $EC_{50}$ | NAD $EC_{50}$ |
| 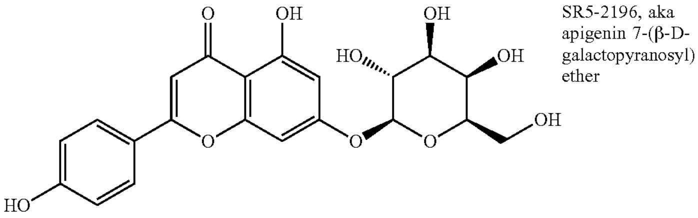 | SR5-2196, aka apigenin 7-(β-D-galactopyranosyl) ether | 4.6 μM | >10 μM |
| 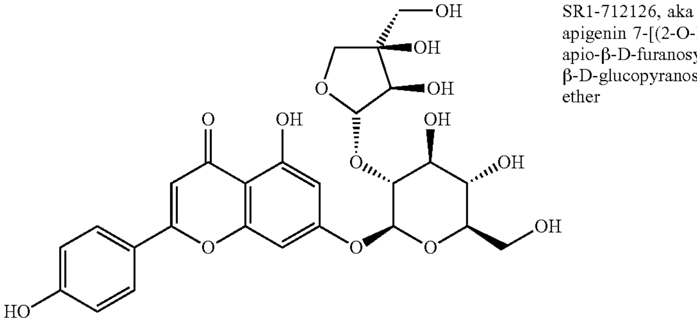 | SR1-712126, aka apigenin 7-[(2-O-D-apio-β-D-furanosyl-β-D-glucopyranosyl ether | 4.6 μM | 10.7 μM |
| 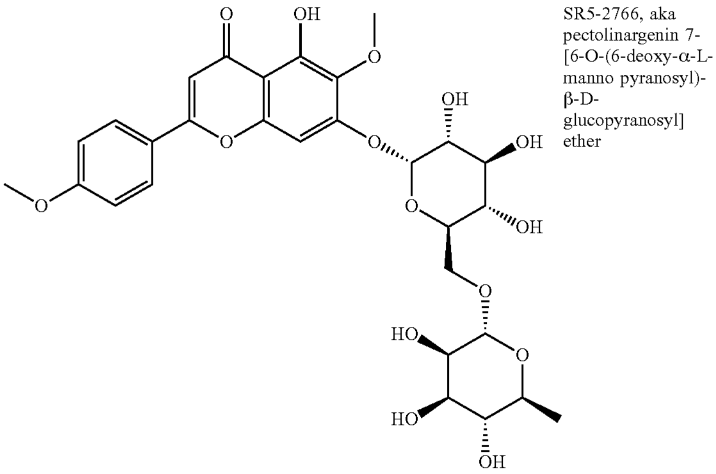 | SR5-2766, aka pectolinargenin 7-[6-O-(6-deoxy-α-L-manno pyranosyl)-β-D-glucopyranosyl] ether | 2.1 μM | 4.0 μM |
| 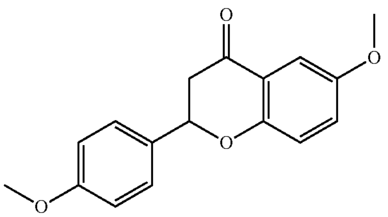 | SR5-2542, aka 6-methoxy-2-(4-methoxyphenyl) chroman-4-one | 2.1 μM | >10 μM |

TABLE 7

| Alkaloids, including selected members of isoquinoline, aporphine, and ergotalkaloid families: | | | |
|---|---|---|---|
| Structure | Data | Viability $EC_{50}$ | NAD $EC_{50}$ |
| 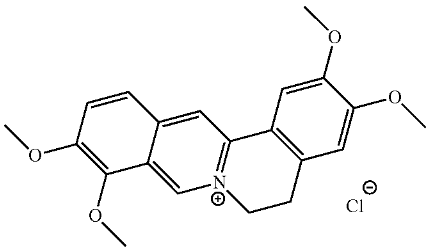 | SR1-841226 aka palmatine chloride, an isoquinoline alkaloid | 1.1 μM | 2.0 μM |
| 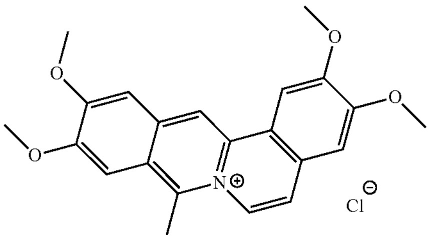 | SR5-2641, aka coralyne chloride, an isoquinoline alkaloid | 507 nM | 671 nM |
| 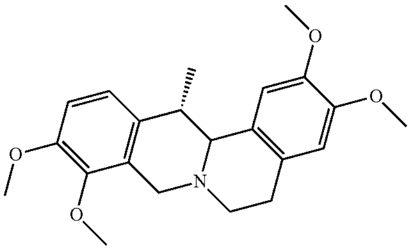 | SR5-2225, aka corydaline, an isoquinoline alkaloid | 1.3 μM | 2.0 μM |
| 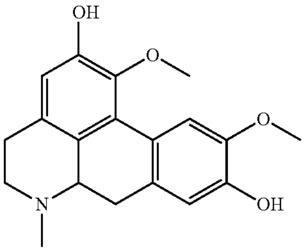 [SMILES: COc1cc2c(cc1O)CC1c3c(cc(O)c(OC)c3-2)CCN1C] | SR1-758928, aka boldine, an isoquinoline alkaloid | 2.0 μM | 7.6 μM |
| 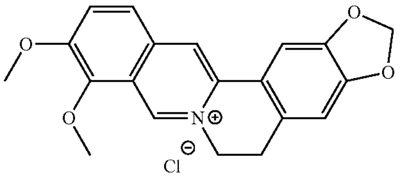 [SMILES: COc1ccc2cc3[n+](cc2c1OC)CCc1cc2c(cc1-3)OCO2 ; [Cl-]] | SR1-711827, aka berberine chloride | 3.1 μM | 13.2 μM |
| 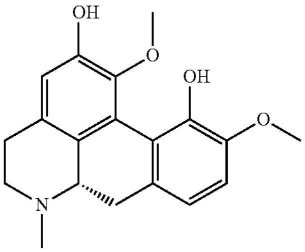 [SMILES: COc1ccc2c(c1O)-c1c(OC)c(O)cc3c1[C@H](C2)N(C)CC3] | SR1-841246, aka N-Methyl lindcarpine, an aporphine alkaloid | 4.4 μM | >15 μM |

TABLE 7-continued

| Alkaloids, including selected members of isoquinoline, aporphine, and ergotalkaloid families: | | | |
|---|---|---|---|
| Structure | Data | Viability $EC_{50}$ | NAD $EC_{50}$ |
| 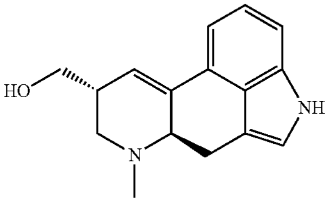 | SR1-758923, aka lysergol, an ergot alkaloid | 1.9 μM | >15 μM |
| 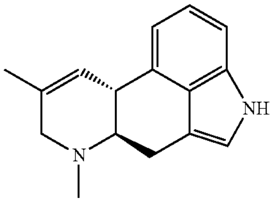 [SMILES: CC1=C[C@@H]2c3cccc4[nH]cc(c34)C[C@H]2N(C)C1] | SR1-75354, aka agroclavine, an ergot alkaloid | 1.6 μM | 2.0 μM |
| 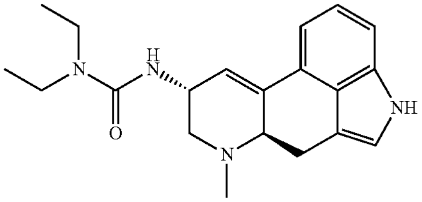 [SMILES: CCN(CC)C(=O)N[C@@H]1C=C2c3cccc4[nH]cc(c34)C[C@H]2N(C)C1] | SR1-75971, aka lisuride, an ergot alkaloid | 4.1 μM | >15 μM |

TABLE 8

| 3-heteroarylquinolines (DMPQ) | | | |
|---|---|---|---|
| Structure | Data | Viability $EC_{50}$ | NAD $EC_{50}$ |
| 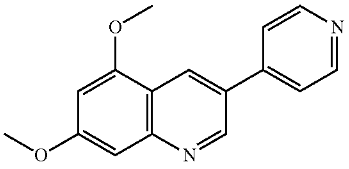 [SMILES: COc1cc(OC)c2cc(-c3ccncc3)cnc2c1] | DMPQ SR-01000597975 | 505 nM | 5.5 μM |

TABLE 9

| Compounds of Formula (II) | | |
|---|---|---|
| Structure | identifier | Viability $EC_{50}$ |
| 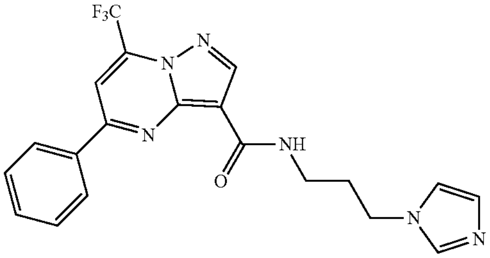 [SMILES: O=C(NCCCn1ccnc1)c1cnn2c(C(F)(F)F)cc(-c3ccccc3)nc12] | SR1-293229 | 1.5 nM, 2 nM |

TABLE 9-continued
| Compounds of Formula (II) | | |
|---|---|---|
| Structure | identifier | Viability $EC_{50}$ |
| 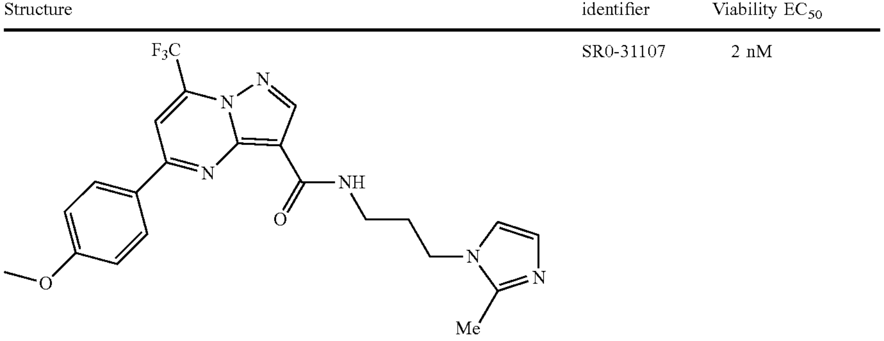 | SR0-31107 | 2 nM |
| 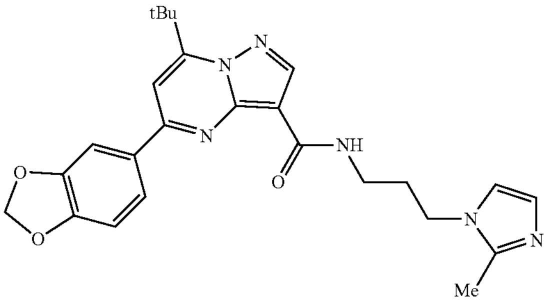 [SMILES: Cc1nccn1CCCNC(=O)c1cnn2c(C(C)(C)C)cc(-c3ccc4c(c3)OCO4)nc12] | SR0-31104 | 10 nM |
| 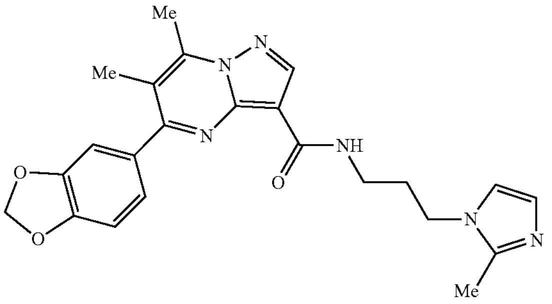 [SMILES: Cc1c(-c2ccc3c(c2)OCO3)nc2c(C(=O)NCCCn3ccnc3C)cnn2c1C] | SR0-31106 | 30 nM |
| 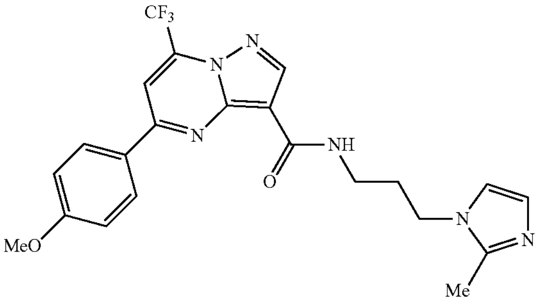 [SMILES: COc1ccc(-c2cc(C(F)(F)F)n3ncc(C(=O)NCCCn4ccnc4C)c3n2)cc1] | SR0-31108 | >50 nM |
| 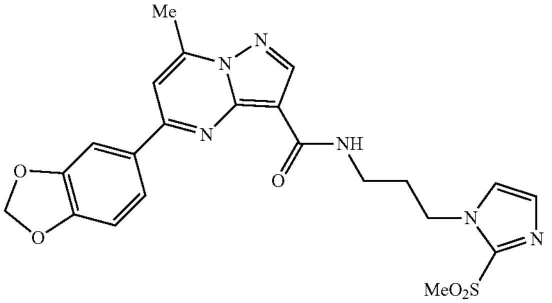 [SMILES: Cc1cc(-c2ccc3c(c2)OCO3)nc2c(C(=O)NCCCn3ccnc3S(C)(=O)=O)cnn12] | SR0-31110 | >50 nM |

TABLE 9-continued
| Compounds of Formula (II) | | |
|---|---|---|
| Structure | identifier | Viability $EC_{50}$ |
| 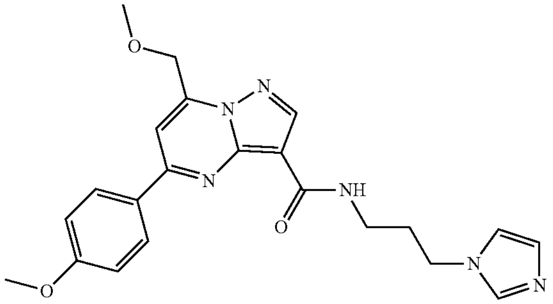 [SMILES: COCc1cc(-c2ccc(OC)cc2)nc2c(C(=O)NCCCn3ccnc3)cnn12] | SR3-5250 | 0.5 nM |
| 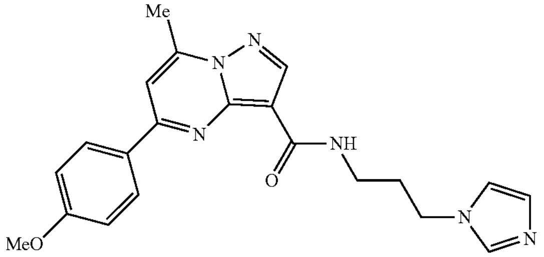 [SMILES: COc1ccc(-c2cc(C)n3ncc(C(=O)NCCCn4ccnc4)c3n2)cc1] | SR3-5170 | 1 nM |
| 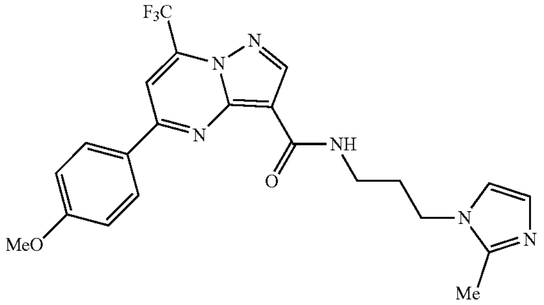 [SMILES: COc1ccc(-c2cc(C(F)(F)F)n3ncc(C(=O)NCCCn4ccnc4C)c3n2)cc1] | SR3-5210 | 2.7 nM |
| 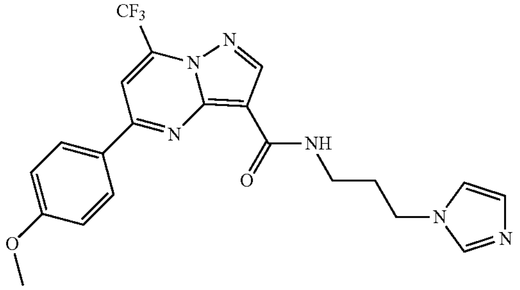 [SMILES: COc1ccc(-c2cc(C(F)(F)F)n3ncc(C(=O)NCCCn4ccnc4)c3n2)cc1] | SR3-5230 | >32 nM |
| 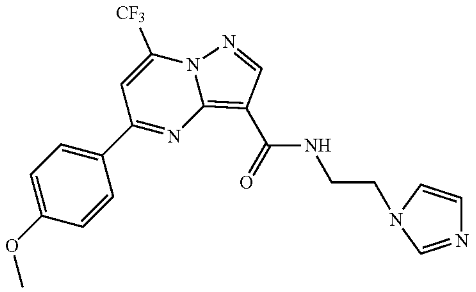 [SMILES: COc1ccc(-c2cc(C(F)(F)F)n3ncc(C(=O)NCCn4ccnc4)c3n2)cc1] | SR3-5290 | >32 nM |

TABLE 9-continued
| Compounds of Formula (II) | | |
|---|---|---|
| Structure | identifier | Viability $EC_{50}$ |
| 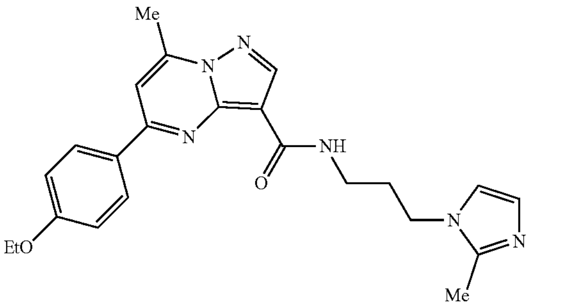 [SMILES: CCOc1ccc(-c2cc(C)n3ncc(C(=O)NCCCn4ccnc4C)c3n2)cc1] | SR0-29245 | 1.2 nM |
| 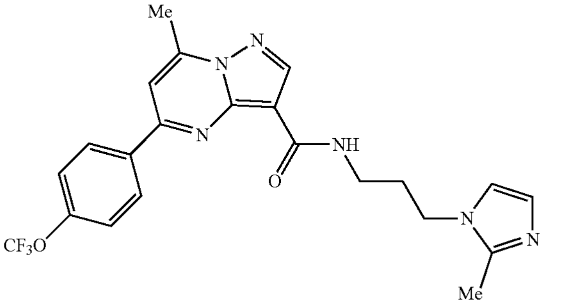 | SR0-29246 | 2 nM |
| 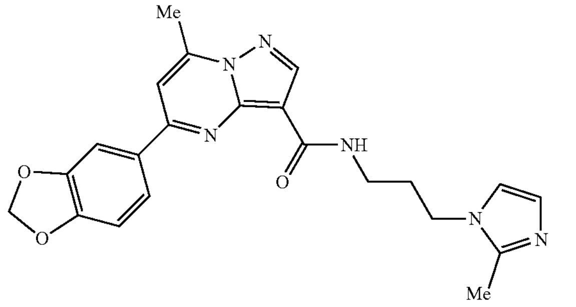 [SMILES: Cc1nccn1CCCNC(=O)c1cnn2c(C)cc(-c3ccc4c(c3)OCO4)nc12] | SR0-29247 | 2.2 nM |
| 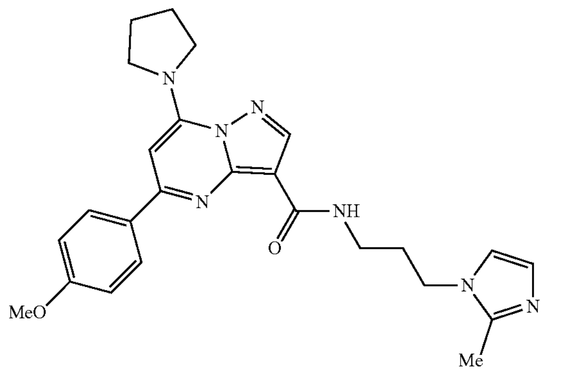 [SMILES: COc1ccc(-c2cc(N3CCCC3)n3ncc(C(=O)NCCCn4ccnc4C)c3n2)cc1] | SR0-29249 | 2.2 nM |

TABLE 9-continued
| Compounds of Formula (II) | | |
|---|---|---|
| Structure | identifier | Viability $EC_{50}$ |
| 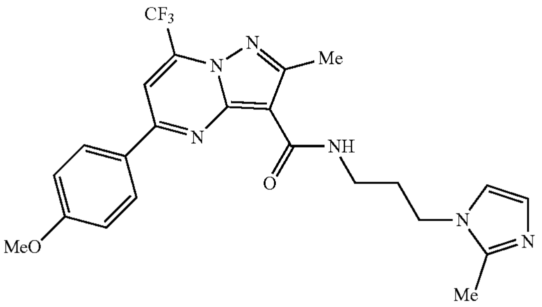 [SMILES: COc1ccc(-c2cc(C(F)(F)F)n3nc(C)c(C(=O)NCCCn4ccnc4C)c3n2)cc1] | SR0-29250 | 3.6 nM |
| 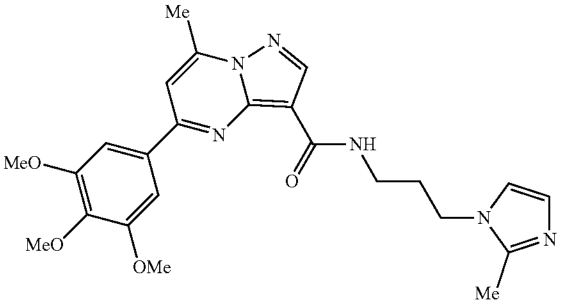 [SMILES: COc1cc(-c2cc(C)n3ncc(C(=O)NCCCn4ccnc4C)c3n2)cc(OC)c1OC] | SR0-29248 | 4 nM |
| 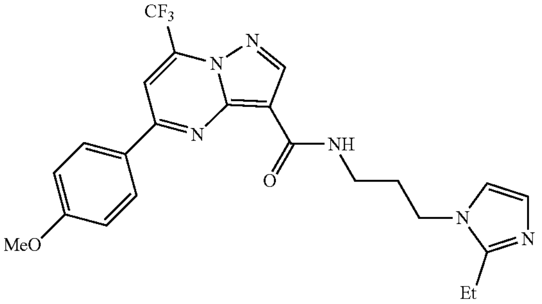 | SR0-29244 | 25 nM |
| 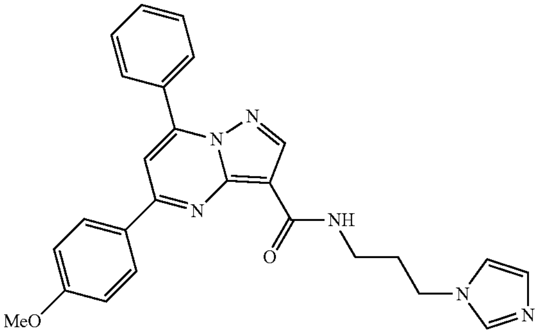 [SMILES: COc1ccc(-c2cc(-c3ccccc3)n3ncc(C(=O)NCCCn4ccnc4)c3n2)cc1] | SR0-28465 | 1 nM |
| 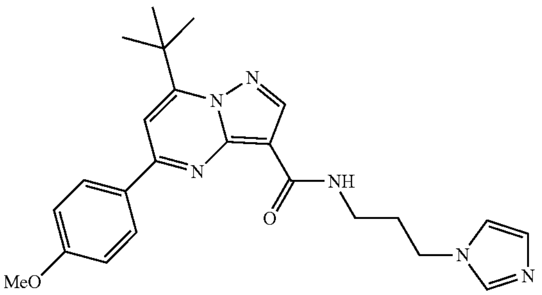 [SMILES: COc1ccc(-c2cc(C(C)(C)C)n3ncc(C(=O)NCCCn4ccnc4)c3n2)cc1] | SR0-28464 | 1.2 nM |

TABLE 9-continued
| Compounds of Formula (II) | | |
|---|---|---|
| Structure | identifier | Viability $EC_{50}$ |
| 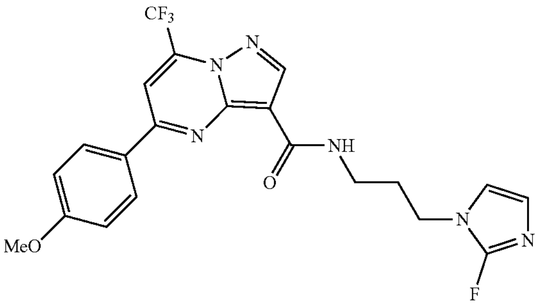 [SMILES: COc1ccc(-c2cc(C(F)(F)F)n3ncc(C(=O)NCCCn4ccnc4F)c3n2)cc1] | SR0-28467 | 16 nM |
| 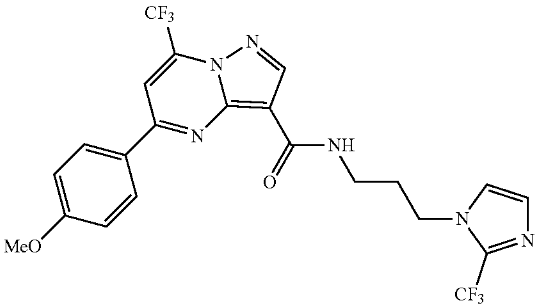 [SMILES: COc1ccc(-c2cc(C(F)(F)F)n3ncc(C(=O)NCCCn4ccnc4C(F)(F)F)c3n2)cc1] | SR0-28466 | 20 nM |
| 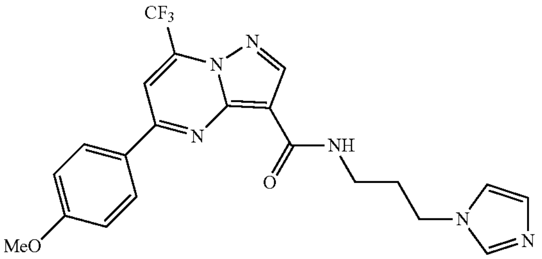 [SMILES: COc1ccc(-c2cc(C(F)(F)F)n3ncc(C(=O)NCCCn4ccnc4)c3n2)cc1] | SR0-28468 | >50 nM |
| 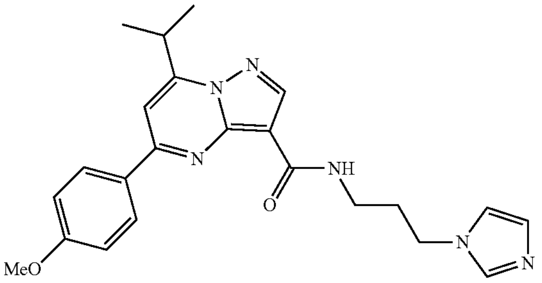 [SMILES: COc1ccc(-c2cc(C(C)C)n3ncc(C(=O)NCCCn4ccnc4)c3n2)cc1] | SR3-5311 | 0.4 nM |
| 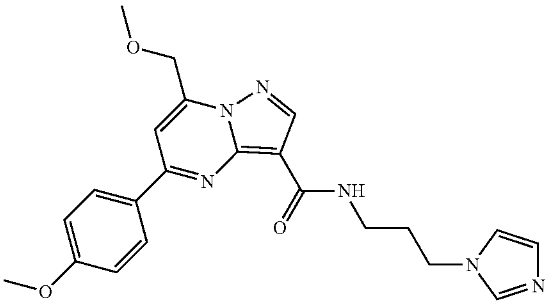 [SMILES: COCc1cc(-c2ccc(OC)cc2)nc2c(C(=O)NCCCn3ccnc3)cnn12] | SR3-5250 | 0.5 nM |

TABLE 9-continued
| Compounds of Formula (II) | | |
|---|---|---|
| Structure | identifier | Viability $EC_{50}$ |
| 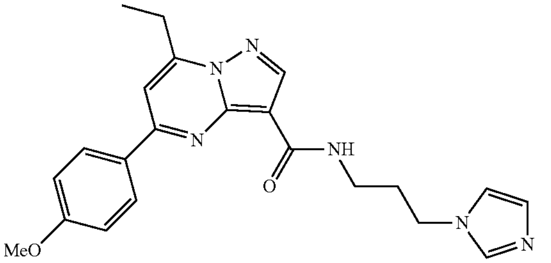 [SMILES: CCc1cc(-c2ccc(OC)cc2)nc2c(C(=O)NCCCn3ccnc3)cnn12] | SR3-5310 | 0.6 nM |
| 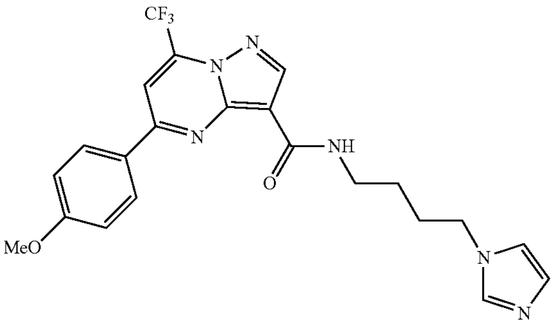 [SMILES: COc1ccc(-c2cc(C(F)(F)F)n3ncc(C(=O)NCCCCn4ccnc4)c3n2)cc1] | SR3-5312 | 6 nM |
| 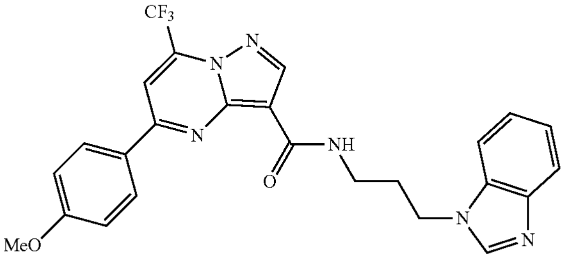 [SMILES: COc1ccc(-c2cc(C(F)(F)F)n3ncc(C(=O)NCCCn4cnc5ccccc54)c3n2)cc1] | SR3-5313 | >16 nM |
| 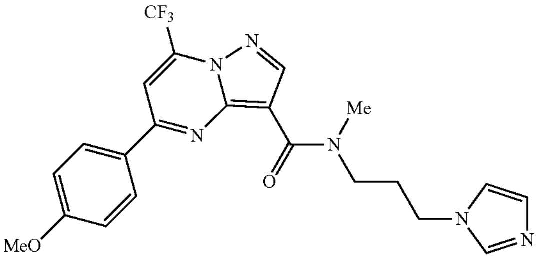 [SMILES: COc1ccc(-c2cc(C(F)(F)F)n3ncc(C(=O)N(C)CCCn4ccnc4)c3n2)cc1] | SR3-5314 | >16 nM |
| 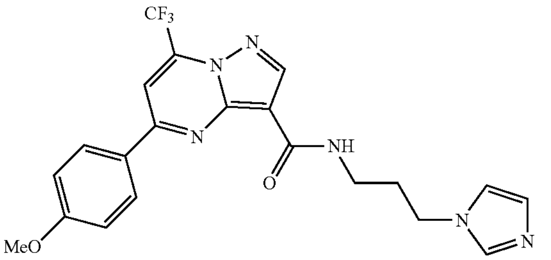 | SR3-5315 | >16 nM |

TABLE 9-continued
| Compounds of Formula (II) | | |
|---|---|---|
| Structure | identifier | Viability $EC_{50}$ |
| 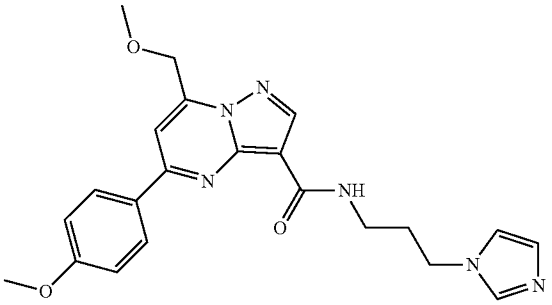 [SMILES: COCc1cc(-c2ccc(OC)cc2)nc2c(C(=O)NCCCn3ccnc3)cnn12] | SR3-5250 | 0.5 nM |
| 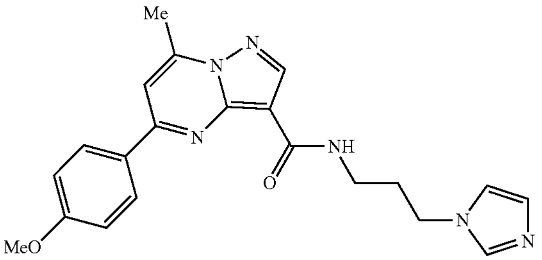 [SMILES: COc1ccc(-c2cc(C)n3ncc(C(=O)NCCCn4ccnc4)c3n2)cc1] | SR3-5170 | 1 nM |
| 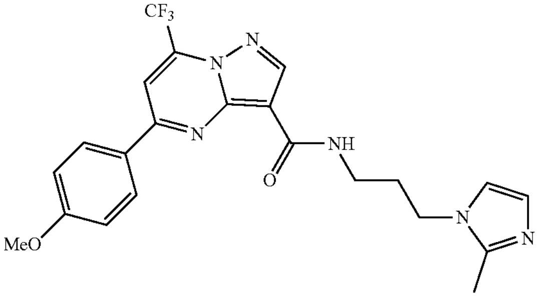 [SMILES: COc1ccc(-c2cc(C(F)(F)F)n3ncc(C(=O)NCCCn4ccnc4C)c3n2)cc1] | SR3-5210 | 2.7 nM |
| 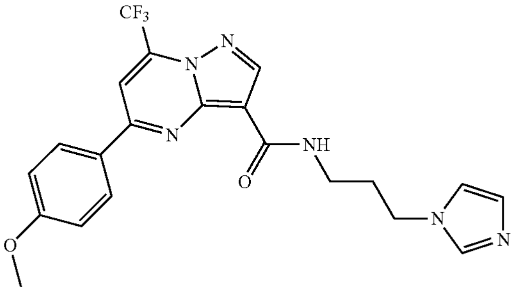 [SMILES: COc1ccc(-c2cc(C(F)(F)F)n3ncc(C(=O)NCCCn4ccnc4)c3n2)cc1] | SR3-5230 | >32 nM |
| 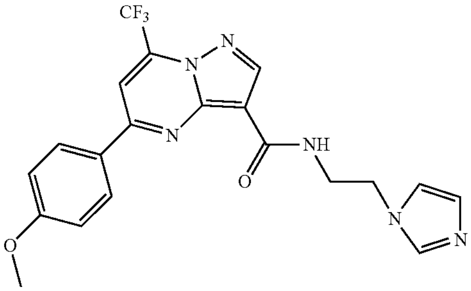 [SMILES: COc1ccc(-c2cc(C(F)(F)F)n3ncc(C(=O)NCCn4ccnc4)c3n2)cc1] | SR3-5290 | >32 nM |

TABLE 9-continued
| Compounds of Formula (II) | | |
|---|---|---|
| Structure | identifier | Viability $EC_{50}$ |
| 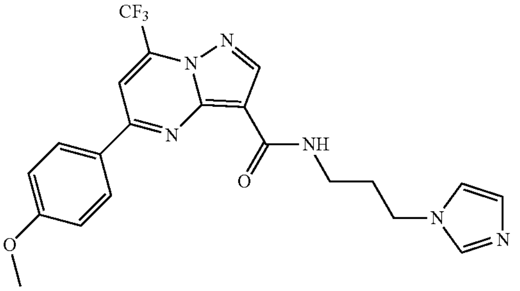 [SMILES: COc1ccc(-c2cc(C(F)(F)F)n3ncc(C(=O)NCCCn4ccnc4)c3n2)cc1] | SR0-24081 | 0.5 nM |
TABLE 10
| Compounds of Formula (III) | | |
|---|---|---|
| Structure | identifier | Viability $EC_{50}$ |
| 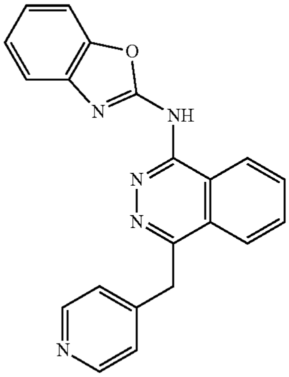 [SMILES: c1ccc2oc(Nc3nnc(Cc4ccncc4)c4ccccc34)nc2c1] | SR-30010 | 2 nM |
| 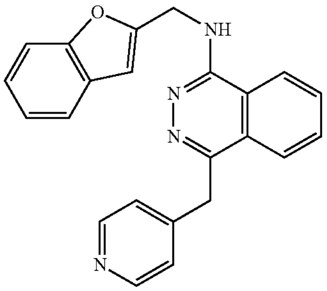 [SMILES: c1ccc2oc(CNc3nnc(Cc4ccncc4)c4ccccc34)cc2c1] | SR-30011 | 2 nM |
| 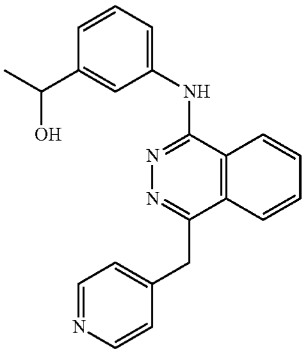 [SMILES: CC(O)c1cccc(Nc2nnc(Cc3ccncc3)c3ccccc23)c1] | SR-29684 | 2 nM |
TABLE 10-continued
| Compounds of Formula (III) | | |
|---|---|---|
| Structure | identifier | Viability $EC_{50}$ |
| 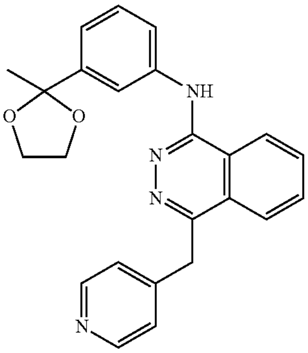 [SMILES: CC1(c2cccc(Nc3nnc(Cc4ccncc4)c4ccccc34)c2)OCCO1] | SR-30012 | 2 nM |
| 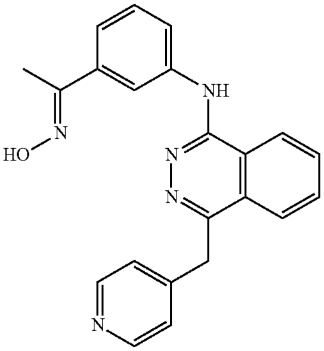 [SMILES: C/C(=N\O)c1cccc(Nc2nnc(Cc3ccncc3)c3ccccc23)c1] | SR-30013 | 2 nM |
| 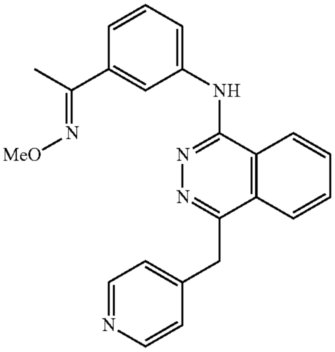 [SMILES: CO/N=C(\C)c1cccc(Nc2nnc(Cc3ccncc3)c3ccccc23)c1] | SR-30014 | 2 nM (lower $EC_{100}$) |

TABLE 10-continued
| Compounds of Formula (III) | | |
|---|---|---|
| Structure | identifier | Viability $EC_{50}$ |
| 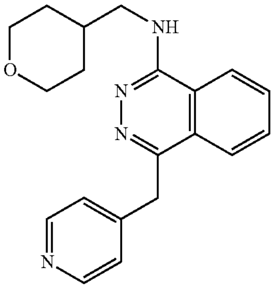 [SMILES: c1ccc2c(NCC3CCOCC3)nnc(Cc3ccncc3)c2c1] | SR-30008 | 8 nM |
| 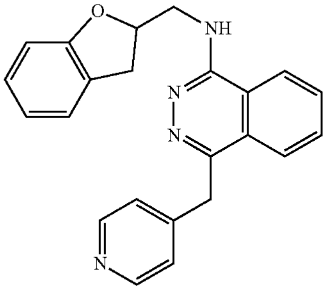 [SMILES: c1ccc2c(c1)CC(CNc1nnc(Cc3ccncc3)c3ccccc13)O2] | SR-30024 | 8 nM |
| 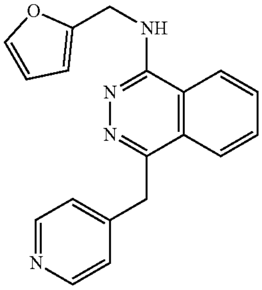 [SMILES: c1coc(CNc2nnc(Cc3ccncc3)c3ccccc23)c1] | SR-30005 | 15 nM |
| 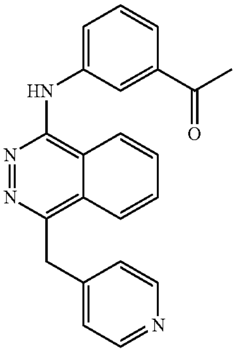 [SMILES: CC(=O)c1cccc(Nc2nnc(Cc3ccncc3)c3ccccc23)c1] | SR1-134005 | 20 nM |
| 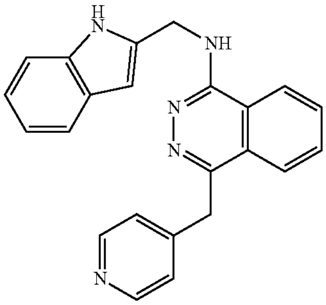 [SMILES: c1ccc2[nH]c(CNc3nnc(Cc4ccncc4)c4ccccc34)cc2c1] | SR-30006 | 30 nM |
TABLE 10-continued
| Compounds of Formula (III) | | |
|---|---|---|
| Structure | identifier | Viability $EC_{50}$ |
| 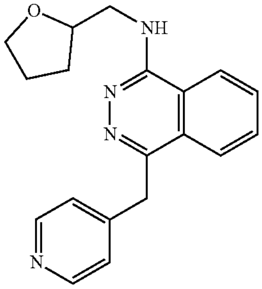 [SMILES: c1ccc2c(NCC3CCCO3)nnc(Cc3ccncc3)c2c1] | SR-30004 | 45 nM |
| 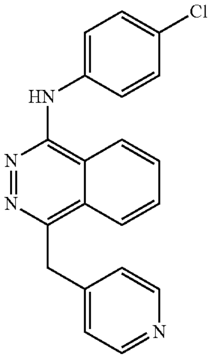 [SMILES: Clc1ccc(Nc2nnc(Cc3ccncc3)c3ccccc23)cc1] | vatalanib | 45 nM |
| 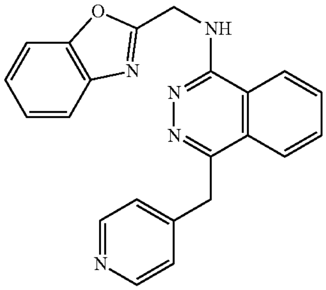 [SMILES: c1ccc2oc(CNc3nnc(Cc4ccncc4)c4ccccc34)nc2c1] | SR-27888 | 45 nM |
| 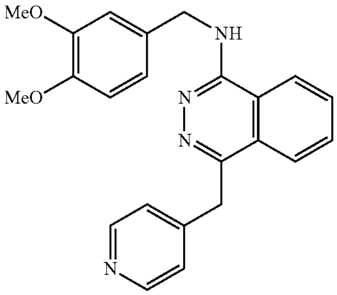 [SMILES: COc1ccc(CNc2nnc(Cc3ccncc3)c3ccccc23)cc1OC] | SR-27886 | 140 nM |
| 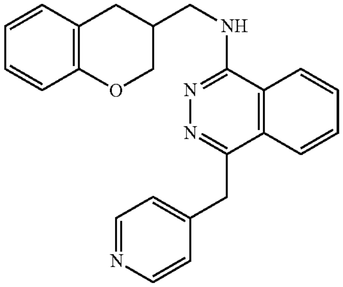 [SMILES: c1ccc2c(c1)CC(CNc1nnc(Cc3ccncc3)c3ccccc13)CO2] | SR-27890 | 140 nM (toxic at >400 nM) |

TABLE 10-continued
Compounds of Formula (III)
| Structure | identifier | Viability $EC_{50}$ |
| --- | --- | --- |
| 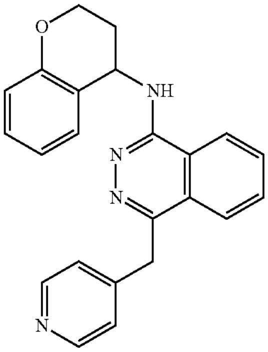 [SMILES: c1ccc2c(c1)OCCC2Nc1nnc(Cc2ccncc2)c2ccccc12] | SR-27891 | 200 nM |
| 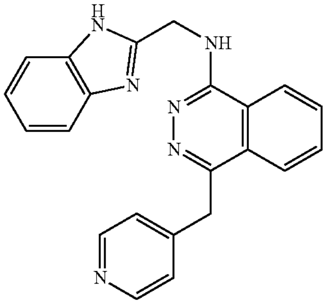 [SMILES: c1ccc2[nH]c(CNc3nnc(Cc4ccncc4)c4ccccc34)nc2c1] | SR-27887 | 200 nM |
| 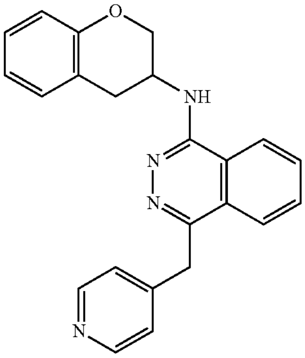 [SMILES: c1ccc2c(c1)CC(Nc1nnc(Cc3ccncc3)c3ccccc13)CO2] | SR-27889 | 200 nM |
| 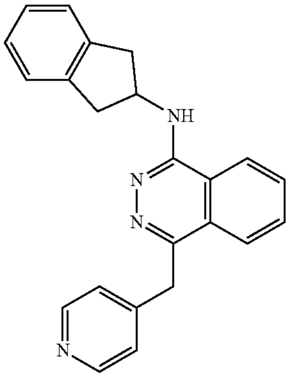 [SMILES: c1ccc2c(c1)CC(Nc1nnc(Cc3ccncc3)c3ccccc13)C2] | SR-27885 | 200 nM |
TABLE 10-continued
Compounds of Formula (III)
| Structure | identifier | Viability $EC_{50}$ |
| --- | --- | --- |
| 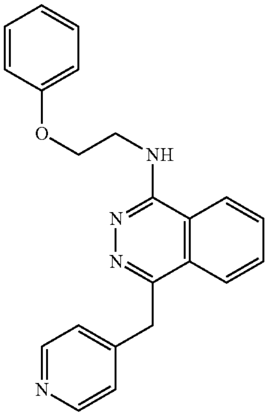 [SMILES: c1ccc(OCCNc2nnc(Cc3ccncc3)c3ccccc23)cc1] | SR-27892 | 500 nM |
| 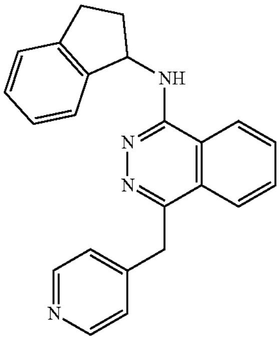 [SMILES: c1ccc2c(c1)CCC2Nc1nnc(Cc2ccncc2)c2ccccc12] | SR-27884 | 500 nM |
TABLE 11
Compounds of Formula (IV)
| Structure | identifier | Viability $EC_{50}$ |
| --- | --- | --- |
| 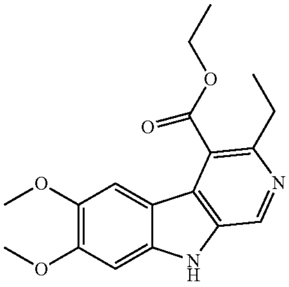 [SMILES: CCOC(=O)c1c(CC)ncc2[nH]c3cc(OC)c(OC)cc3c12] | SR26084 | ~10 µM (30% protection at 4 µM) |
| 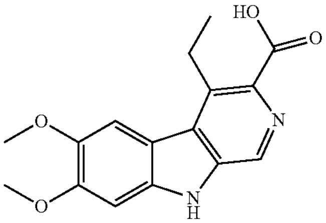 [SMILES: CCc1c(C(=O)O)ncc2[nH]c3cc(OC)c(OC)cc3c12] | SR26266 | >4 µM |

TABLE 12
| Compounds of Formula (V) | | |
|---|---|---|
| Structure | identifier | Viability $EC_{50}$ |
| 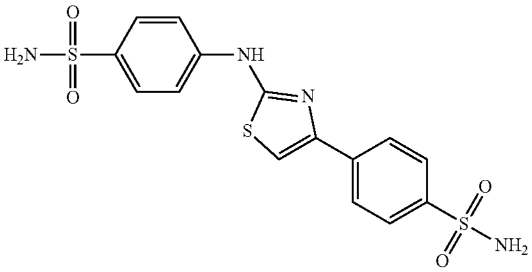 [SMILES: NS(=O)(=O)c1ccc(Nc2nc(-c3ccc(S(N)(=O)=O)cc3)cs2)cc1] | SR-29450 | 15 nM |
| 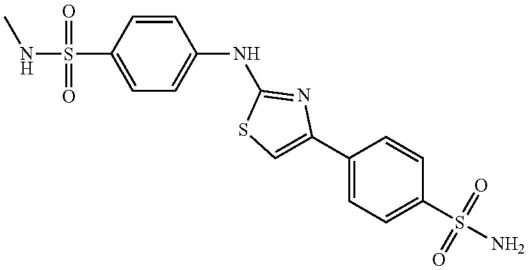 [SMILES: CNS(=O)(=O)c1ccc(Nc2nc(-c3ccc(S(N)(=O)=O)cc3)cs2)cc1] | SR-29451 | 20 nM |
| 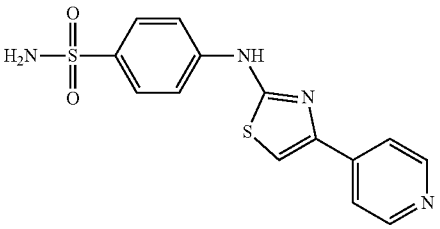 [SMILES: NS(=O)(=O)c1ccc(Nc2nc(-c3ccncc3)cs2)cc1] | SR1-477186 | 40 nM<br>50 nM |
| 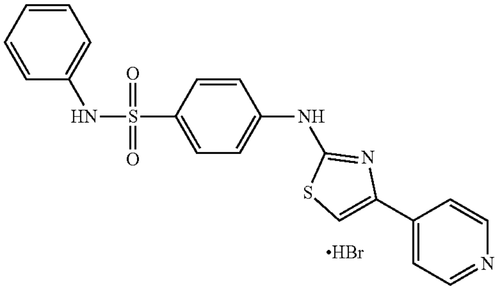 [SMILES: O=S(=O)(Nc1ccccc1)c1ccc(Nc2nc(-c3ccncc3)cs2)cc1 ; Br] | SR-29444 | >500 nM |
| 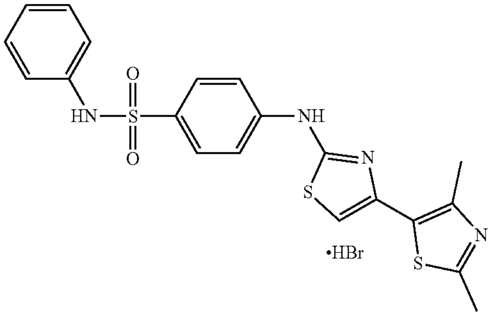 [SMILES: Cc1nc(C)c(-c2csc(Nc3ccc(S(=O)(=O)Nc4ccccc4)cc3)n2)s1 ; Br] | SR-29445 | >500 nM |

TABLE 12-continued
| Compounds of Formula (V) | | |
|---|---|---|
| Structure | identifier | Viability $EC_{50}$ |
| 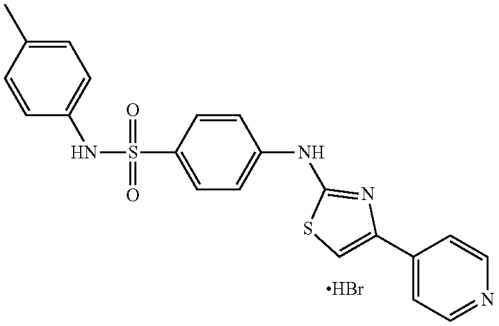 [SMILES: Cc1ccc(NS(=O)(=O)c2ccc(Nc3nc(-c4ccncc4)cs3)cc2)cc1 ; Br] | SR-29446 | >500 nM |
| 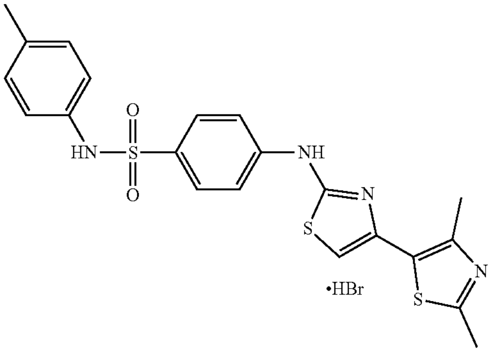 [SMILES: Cc1ccc(NS(=O)(=O)c2ccc(Nc3nc(-c4sc(C)nc4C)cs3)cc2)cc1 ; Br] | SR-29447 | >500 nM |
| 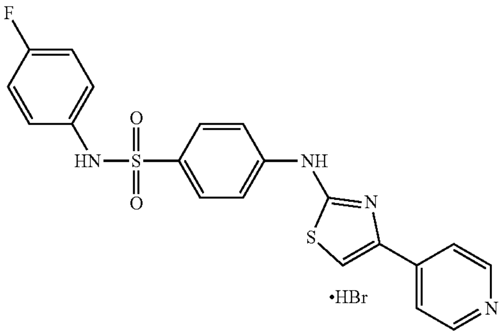 [SMILES: O=S(=O)(Nc1ccc(F)cc1)c1ccc(Nc2nc(-c3ccncc3)cs2)cc1 ; Br] | SR-29448 | >500 nM |
| 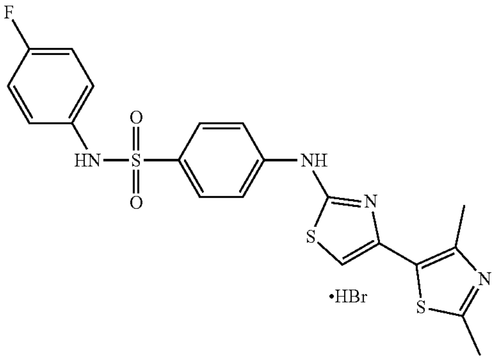 [SMILES: Cc1nc(C)c(-c2csc(Nc3ccc(S(=O)(=O)Nc4ccc(F)cc4)cc3)n2)s1 ; Br] | SR-29449 | >500 nM |

TABLE 12-continued
| Compounds of Formula (V) | | |
| --- | --- | --- |
| Structure | identifier | Viability $EC_{50}$ |
| 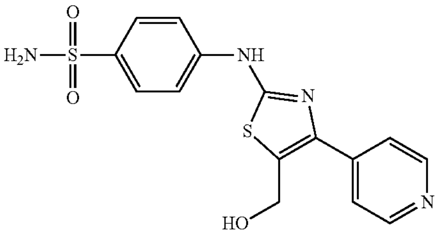 SR0-28550-1 | SR-28550 | 60 nM |
| 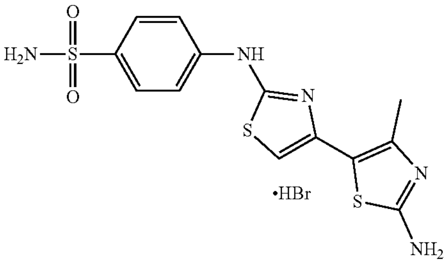 SR0-28552-1 | SR-28552 | 160 nM |
| 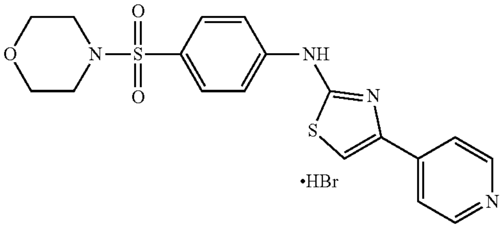 SR0-28548-1 | SR-28548 | 170 nM |
| 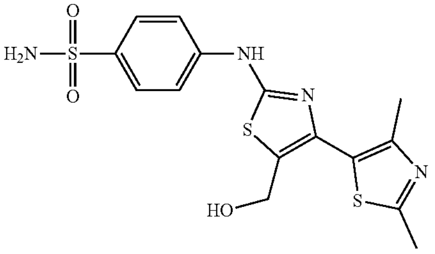 SR0-28551-1 | SR-28551 | 300 nM |
| 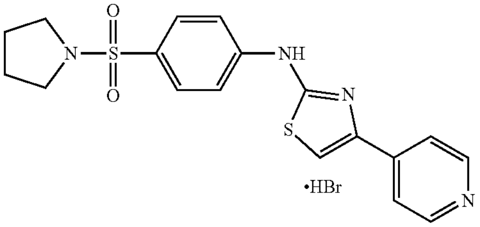 SR0-28544-1 | SR-28544 | 350 nM |

TABLE 12-continued
| Compounds of Formula (V) | | |
|---|---|---|
| Structure | identifier | Viability $EC_{50}$ |
| 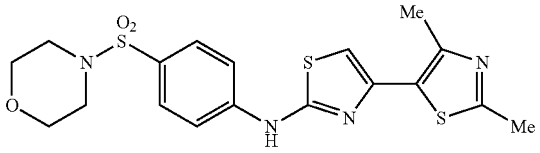 [SMILES: Cc1nc(C)c(-c2csc(Nc3ccc(S(=O)(=O)N4CCOCC4)cc3)n2)s1] | SR-28549 | 400 nM |
| 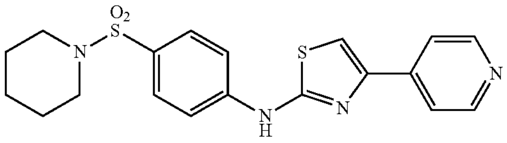 [SMILES: O=S(=O)(c1ccc(Nc2nc(-c3ccncc3)cs2)cc1)N1CCCCC1] | SR-28546 | 400 nM |
| 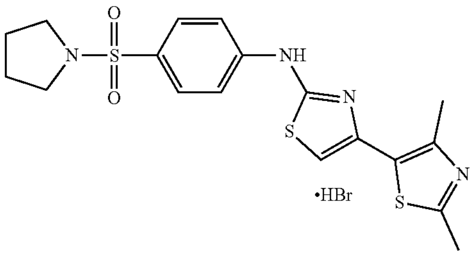 SR0-28545-1 | SR-28545 | >500 nM |
| 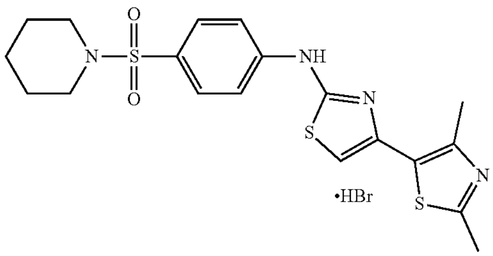 SR0-28547-1 | SR-28547 | >500 nM |
| 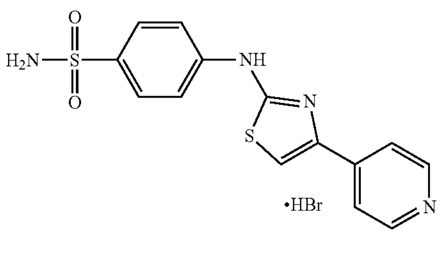 [SMILES: NS(=O)(=O)c1ccc(Nc2nc(-c3ccncc3)cs2)cc1 ; Br] | SR477186 | 20, 30, 35 nM |
| 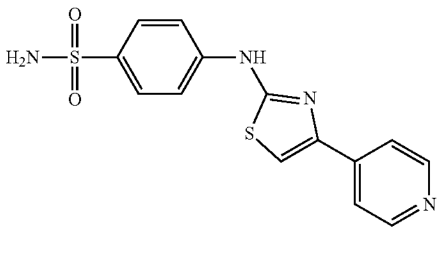 [SMILES: NS(=O)(=O)c1ccc(Nc2nc(-c3ccncc3)cs2)cc1] | | |

TABLE 12-continued
Compounds of Formula (V)
| Structure | identifier | Viability $EC_{50}$ |
| --- | --- | --- |
| 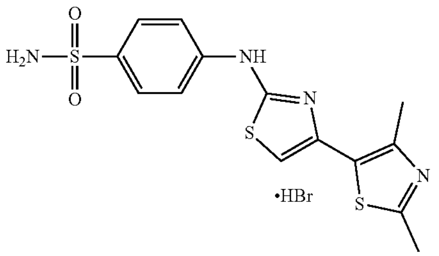 [SMILES: Cc1nc(C)c(-c2csc(Nc3ccc(S(N)(=O)=O)cc3)n2)s1 ; Br] | SR477302 | 18, 30 nM |
| 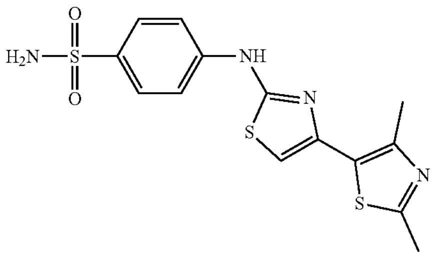 [SMILES: Cc1nc(C)c(-c2csc(Nc3ccc(S(N)(=O)=O)cc3)n2)s1] | | |
| | SR-27807 | 50 nM |
| 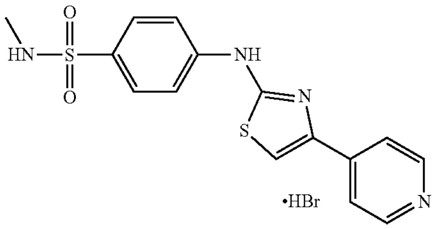 [SMILES: CNS(=O)(=O)c1ccc(Nc2nc(-c3ccncc3)cs2)cc1 ; Br] | SR-27806 | 60 nM |
| 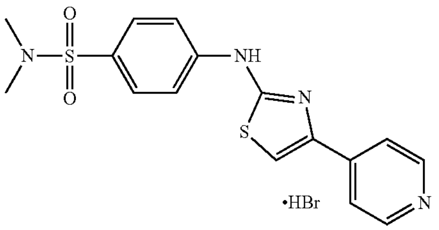 [SMILES: CN(C)S(=O)(=O)c1ccc(Nc2nc(-c3ccncc3)cs2)cc1 ; Br] | SR-27744 | 60 nM |
| 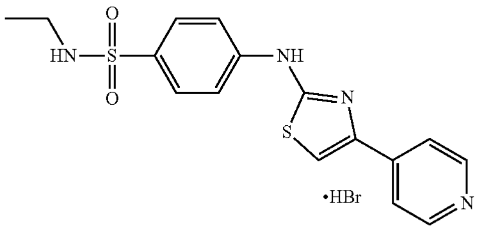 [SMILES: CCNS(=O)(=O)c1ccc(Nc2nc(-c3ccncc3)cs2)cc1 ; Br] | SR-27784 | 60 nM |
| 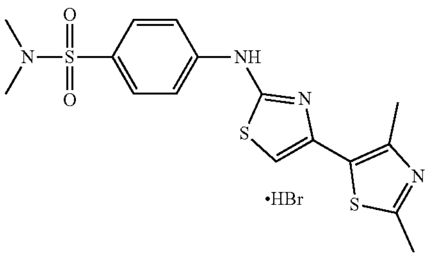 [SMILES: Cc1nc(C)c(-c2csc(Nc3ccc(S(=O)(=O)N(C)C)cc3)n2)s1 ; Br] | SR-27764 | 70 nM |

TABLE 12-continued
| Compounds of Formula (V) | | |
|---|---|---|
| Structure | identifier | Viability $EC_{50}$ |
| 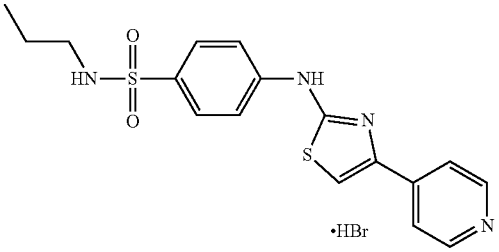 [SMILES: CCCNS(=O)(=O)c1ccc(Nc2nc(-c3ccncc3)cs2)cc1 ; Br] | SR-27804 | 170 nM |
| 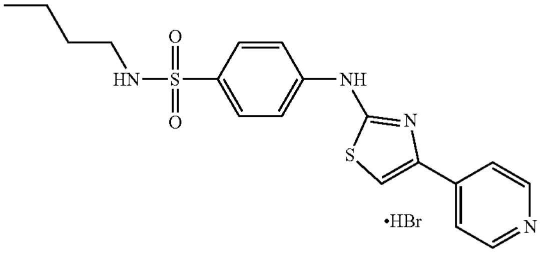 [SMILES: CCCCNS(=O)(=O)c1ccc(Nc2nc(-c3ccncc3)cs2)cc1 ; Br] | SR-27808 | 170 nM |
| 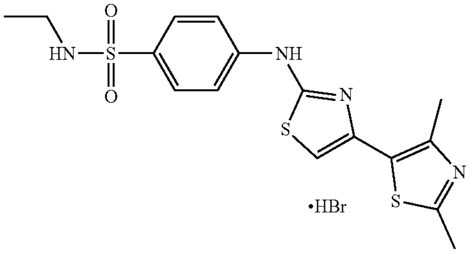 [SMILES: CCNS(=O)(=O)c1ccc(Nc2nc(-c3sc(C)nc3C)cs2)cc1 ; Br] | SR-27785 | 500 nM |
| 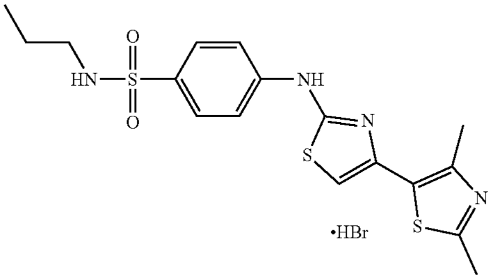 [SMILES: CCCNS(=O)(=O)c1ccc(Nc2nc(-c3sc(C)nc3C)cs2)cc1 ; Br] | SR-27805 | >500 nM |
| 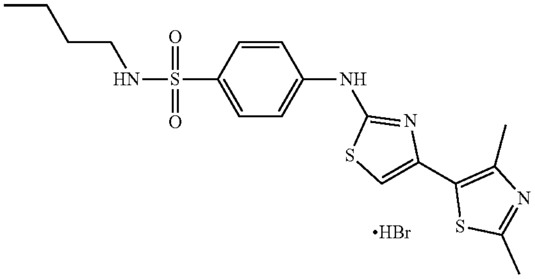 [SMILES: CCCCNS(=O)(=O)c1ccc(Nc2nc(-c3sc(C)nc3C)cs2)cc1 ; Br] | SR-27809 | >500 nM |

REFERENCES

1 Zhou, M., Ottenberg, G., Sferrazza, G. F. & Lasmezas, C. I. Highly neurotoxic monomeric alpha-helical prion protein. *Proc Natl Acad Sci USA* 109, 3113-3118, doi: 10.1073/pnas.1118090109 (2012).

2 Zhou, M. et al. Neuronal death induced by misfolded prion protein is due to NAD+ depletion and can be relieved in vitro and in vivo by NAD+ replenishment. *Brain* 138, 992-1008, doi:10.1093/brain/awv002 (2015).

3 Olivan, S. et al. Comparative study of behavioural tests in the SOD1G93A mouse model of amyotrophic lateral sclerosis. *Exp Anim* 64, 147-153, doi:10.1538/expanim.14-0077 (2015).

4 Dahlin, J. L. et al. PAINS in the assay: chemical mechanisms of assay interference and promiscuous enzymatic inhibition observed during a sulfhydryl-scavenging HTS. *J Med Chem* 58, 2091-2113, doi:10.1021/jm5019093 (2015).

5 Lipinski, C. A., Lombardo, F., Dominy, B. W. & Feeney, P. J. Experimental and computational approaches to estimate solubility and permeability in drug discovery and development settings. *Adv Drug Deliv Rev* 46, 3-26 (2001).

6 Veber, D. F. et al. Molecular properties that influence the oral bioavailability of drug candidates. *J Med Chem* 45, 2615-2623 (2002).

7 Mele, L., Massotti, M. & Gotta, F. Neuropharmacology of several beta-carboline derivatives and their 9-acetylated esters. In vivo versus in vitro studies in the rabbit. *Pharmacol Biochem Behav* 30, 5-11 (1988).

8 Leppa, E. et al. Agonistic effects of the beta-carboline DMCM revealed in GABA(A) receptor gamma 2 subunit F771 point-mutated mice. *Neuropharmacology* 48, 469-478, doi:10.1016/j.neuropharm.2004.11.007 (2005).

9 Atack, J. R., Smith, A. J., Emms, F. & McKernan, R. M. Regional differences in the inhibition of mouse in vivo [3H]Ro 15-1788 binding reflect selectivity for alpha 1 versus alpha 2 and alpha 3 subunit-containing $GABA_A$ receptors. *Neuropsychopharmacology* 20, 255-262, doi: 10.1016/S0893-133X(98)00052-9 (1999).

10 Lista, A., Blier, P. & De Montigny, C. The benzodiazepine receptor inverse agonist DMCM decreases serotonergic transmission in rat hippocampus: an in vivo electrophysiological study. *Synapse* 6, 175-178, doi:10.1002/syn.890060209 (1990).

11 Huang, Q. et al. Pharmacophore/receptor models for GABA(A)/BzR subtypes (alpha1beta3gamma2, alpha5beta3gamma2, and alpha6beta3gamma2) via a comprehensive ligand-mapping approach. *J Med Chem* 43, 71-95 (2000).

12 Grassi, D. et al. Identification of a highly neurotoxic alpha-synuclein species inducing mitochondrial damage and mitophagy in Parkinson's disease. *Proc Natl Acad Sci USA* 115, E2634-E2643, doi:10.1073/pnas.1713849115 (2018).

13 Walters, W. P. Going further than Lipinski's rule in drug design. *Expert Opin Drug Discov* 7, 99-107, doi:10.1517/17460441.2012.648612 (2012).

14 Crestani, F., Assandri, R., Tauber, M., Martin, J. R. & Rudolph, U. Contribution of the alpha1-GABA(A) receptor subtype to the pharmacological actions of benzodiazepine site inverse agonists. *Neuropharmacology* 43, 679-684 (2002).

15 Gurney, M. E. et al. Motor neuron degeneration in mice that express a human Cu,Zn superoxide dismutase mutation. *Science* 264, 1772-1775 (1994).

16 Pokrishevsky, E. et al. Aberrant localization of FUS and TDP43 is associated with misfolding of SOD1 in amyotrophic lateral sclerosis. *PLoS One* 7, e35050, doi: 10.1371/journal.pone.0035050 (2012).

17 Brander, D. et al. Phase II open label study of the oral vascular endothelial growth factor-receptor inhibitor PTK787/ZK222584 (vatalanib) in adult patients with refractory or relapsed diffuse large B-cell lymphoma. *Leuk Lymphoma* 54, 2627-2630, doi:10.3109/10428194.2013.784969 (2013).

18 Raizer, J. J. et al. A phase II trial of PTK787/ZK 222584 in recurrent or progressive radiation and surgery refractory meningiomas. *J Neurooncol* 117, 93-101, doi: 10.1007/s11060-014-1358-9 (2014).

19 Dragovich, T. et al. Phase II trial of vatalanib in patients with advanced or metastatic pancreatic adenocarcinoma after first-line gemcitabine therapy (PCRT 04-001). *Cancer Chemother Pharmacol* 74, 379-387, doi:10.1007/s00280-014-2499-4 (2014).

20 Gupta, P. et al. A phase II study of the oral VEGF receptor tyrosine kinase inhibitor vatalanib (PTK787/ZK222584) in myelodysplastic syndrome: Cancer and Leukemia Group B study 10105 (Alliance). *Invest New Drugs* 31, 1311-1320, doi:10.1007/s10637-013-9978-z (2013).

21 Jain, R. K., Duda, D. G., Clark, J. W. & Loeffler, J. S. Lessons from phase III clinical trials on anti-VEGF therapy for cancer. *Nat Clin Pract Oncol* 3, 24-40, doi: 10.1038/ncponc0403 (2006).

22 Remko, M., Bohác, A. & Kovácikova, L. Molecular structure, pKa, lipophilicity, solubility, absorption, polar surface area, and blood brain barrier penetration of some antiangiogenic agents. *Struct Chem* 22, 635-648 (2011).

23 Bold, G. et al. New anilinophthalazines as potent and orally well absorbed inhibitors of the VEGF receptor tyrosine kinases useful as antagonists of tumor-driven angiogenesis. *J Med Chem* 43, 3200 (2000).

24 Bold, G. et al. Phthalazines with angiogenesis inhibiting activity. WO 98/35958. (1998).

25 Pronto-Laborinho, A. C., Pinto, S. & de Carvalho, M. Roles of vascular endothelial growth factor in amyotrophic lateral sclerosis. *Biomed Res Int* 2014, 947513, doi:10.1155/2014/947513 (2014).

26 Ruiz de Almodovar, C., Lambrechts, D., Mazzone, M. & Carmeliet, P. Role and therapeutic potential of VEGF in the nervous system. *Physiol Rev* 89, 607-648, doi: 10.1152/physrev.00031.2008 (2009).

27 Storkebaum, E. et al. Treatment of motoneuron degeneration by intracerebroventricular delivery of VEGF in a rat model of ALS. *Nat Neurosci* 8, 85-92, doi:10.1038/nn1360 (2005).

28 Zheng, C., Nennesmo, I., Fadeel, B. & Henter, J. I. Vascular endothelial growth factor prolongs survival in a transgenic mouse model of ALS. *Ann Neurol* 56, 564-567, doi:10.1002/ana.20223 (2004).

29 Yasuhara, T. et al. Neuroprotective effects of vascular endothelial growth factor (VEGF) upon dopaminergic neurons in a rat model of Parkinson's disease. *Eur J Neurosci* 19, 1494-1504, doi:10.1111/j.1460-9568.2004.03254.x (2004).

30 Piltonen, M. et al. Vascular endothelial growth factor C acts as a neurotrophic factor for dopamine neurons in vitro and in vivo. *Neuroscience* 192, 550-563, doi: 10.1016/j.neuroscience.2011.06.084 (2011).

31 Sorrentino, V. et al. Enhancing mitochondrial proteostasis reduces amyloid-beta proteotoxicity. *Nature* 552, 187-193, doi:10.1038/nature25143 (2017).

32 Hou, Y. et al. NAD(+) supplementation normalizes key Alzheimer's features and DNA damage responses in a new AD mouse model with introduced DNA repair deficiency. *Proc Natl Acad Sci USA* 115, E1876-E1885, doi:10.1073/pnas.1718819115 (2018).

33 Massudi, H. et al. Age-associated changes in oxidative stress and NAD+metabolism in human tissue. *PLoS One* 7, e42357, doi:10.1371/journal.pone.0042357 (2012).

34 Zhu, X. H., Lu, M., Lee, B. Y., Ugurbil, K. & Chen, W. In vivo NAD assay reveals the intracellular NAD contents and redox state in healthy human brain and their age dependences. *Proc Natl Acad Sci USA* 112, 2876-2881, doi:10.1073/pnas.1417921112 (2015).

35 Zhang, H. et al. NAD(+) repletion improves mitochondrial and stem cell function and enhances life span in mice. *Science* 352, 1436-1443, doi:10.1126/science.aaf2693 (2016).

36 Mouchiroud, L. et al. The NAD(+)/Sirtuin Pathway Modulates Longevity through Activation of Mitochondrial UPR and FOXO Signaling. Cell 154, 430-441, doi:10.1016/j.cell.2013.06.016 (2013).

37 Penberthy, W. T. & Tsunoda, I. The importance of NAD in multiple sclerosis. *Curr Pharm Des* 15, 64-99 (2009).

38 Brown, K. D. et al. Activation of SIRT3 by the NAD(+) precursor nicotinamide riboside protects from noise-induced hearing loss. *Cell Metab* 20, 1059-1068, doi:10.1016/j.cmet.2014.11.003 (2014).

39 Lin, J. B. et al. NAMPT-Mediated NAD(+) Biosynthesis Is Essential for Vision In Mice. *Cell Rep* 17, 69-85, doi:10.1016/j.celrep.2016.08.073 (2016).

40 Satchell, M. A. et al. A dual role for poly-ADP-ribosylation in spatial memory acquisition after traumatic brain injury in mice involving NAD+depletion and ribosylation of 14-3-3gamma. *J Neurochem* 85, 697-708 (2003).

41 Vaur, P. et al. Nicotinamide riboside, a form of vitamin B3, protects against excitotoxicity-induced axonal degeneration. *FASEB J* 31, 5440-5452, doi:10.1096/fj.201700221RR (2017).

42 Ralto, K. M., Rhee, E. P. & Parikh, S. M. NAD(+) homeostasis in renal health and disease. *Nat Rev Nephrol* 16, 99-111, doi:10.1038/s41581-019-0216-6 (2020).

43 Ying, W. et al. Intranasal administration with NAD+ profoundly decreases brain injury in a rat model of transient focal ischemia. *Front Biosci* 12, 2728-2734, doi:2267 [pii] (2007).

44 Hsu, C. P., Oka, S., Shao, D., Hariharan, N. & Sadoshima, J. Nicotinamide phosphoribosyltransferase regulates cell survival through NAD+ synthesis in cardiac myocytes. *Circ Res* 105, 481-491, doi:10.1161/CIRCRESAHA.109.203703 (2009).

45 Yamamoto, T. et al. Nicotinamide mononucleotide, an intermediate of NAD+ synthesis, protects the heart from ischemia and reperfusion. *PLoS One* 9, e98972, doi:10.1371/journal.pone.0098972 (2014).

46 Yoshino, J., Mills, K. F., Yoon, M. J. & Imai, S. Nicotinamide mononucleotide, a key NAD(+) intermediate, treats the pathophysiology of diet- and age-induced diabetes in mice. *Cell Metab* 14, 528-536, doi:10.1016/j.cmet.2011.08.014 (2011).

47 Trammell, S. A. et al. Nicotinamide Riboside Opposes Type 2 Diabetes and Neuropathy in Mice. *Sci Rep* 6, 26933, doi:10.1038/srep26933 (2016).

48 Costes, S. Targeting protein misfolding to protect pancreatic beta-cells in type 2 diabetes. *Curr Opin Pharmacol* 43, 104-110, doi:10.1016/j.coph.2018.08.016 (2018).

49 Ueberberg, S. et al. Islet amyloid in patients with diabetes due to exocrine pancreatic disorders, type 2 diabetes and non-diabetic patients. *J Clin Endocrinol Metab*, doi:10.1210/clinem/dgaa176 (2020).

50 Liu, M. et al. Proinsulin misfolding and diabetes: mutant INS gene-induced diabetes of youth. *Trends Endocrinol Metab* 21, 652-659, doi:10.1016/j.tem.2010.07.001 (2010).

51 Sun, J. et al. Proinsulin misfolding and endoplasmic reticulum stress during the development and progression of diabetes. *Mol Aspects Med* 42, 105-118, doi:10.1016/j.mam.2015.01.001 (2015).

52 Atouf, F., Scharfmann, R., Lasmézas, C. & Czernichow, P. Tight hormonal control of PrP gene expression in endocrine pancreatic cells. *Biochem and Biophys Res Commun* 201, 1220-1226 (1994).

53 Green, A. D., Vasu, S. & Flatt, P. R. Cellular models for beta-cell function and diabetes gene therapy. *Acta Physiol (Oxf)* 222, doi:10.1111/apha.13012 (2018).

54 Al-Awar, A. et al. Experimental Diabetes Mellitus in Different Animal Models. *J Diabetes Res* 2016, 9051426, doi:10.1155/2016/9051426 (2016).

55 Lenzen, S. Animal models of human type 1 diabetes for evaluating combination therapies and successful translation to the patient with type 1 diabetes. *Diabetes Metab Res Rev* 33, doi:10.1002/dmrr.2915 (2017).

56 Cheta, D. Animal models of type I (insulin-dependent) diabetes mellitus. *J Pediatr Endocrinol Metab* 11, 11-19, doi:10.1515/jpem.1998.11.1.11 (1998).

What is claimed is:

1. A method for one or more selected from (i) inhibiting NAD consumption and/or increasing NAD synthesis in a patient, (ii) preventing or inhibiting NAD depletion in a patient, (iii) improving a condition linked to alterations of NAD metabolism in a patient, wherein the condition is a synucleinopathy or amyotrophic lateral sclerosis, (iv) providing protection from toxicity of misfolded proteins in a patient, or (v) treating a protein misfolding neurodegenerative disease in a patient, wherein the protein misfolding neurodegenerative disease is a synucleinopathy or amyotrophic lateral sclerosis, the method comprising administering to the patient an effective dose of a triazolophthalazine compound of Formula (I)

(I)

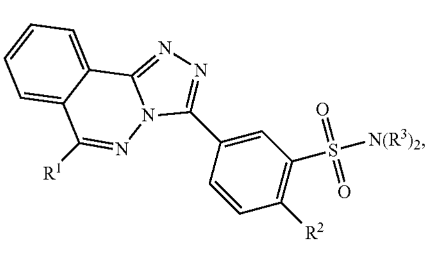

or a pharmaceutically acceptable salt thereof, wherein in Formula (I):

each $R^1$ and $R^2$ are independently hydrogen $(C_1-C_4)$alkyl, or $(C_1-C_4)$alkoxy; and each $R^3$ is independently selected hydrogen, $(C_1-C_4)$alkyl optionally substituted with OH, $(C_1-C_4)$alkoxy, or heteroaryl, and provided that both $R^3$ are not hydrogen; or, both $R^3$ together with the nitrogen atom to which they are bonded form a 5- to 7-membered heterocyclyl ring comprising at least an additional heteroatom selected from O, S, S—O, S(=O)—O, or NR, wherein R is ($C_1$-$C_4$)alkyl optionally substituted with —OH or ($C_1$-$C_4$)alkoxyl, or, an effective dose of a pyrazolopyrimidine compound of Formula (II)

(II)

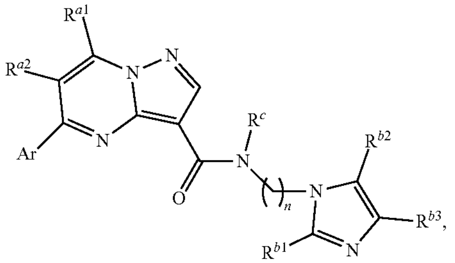

or a pharmaceutically acceptable salt thereof, wherein in Formula (II):

each $R^{a1}$ and $R^{a2}$ is independently hydrogen, ($C_1$-$C_4$) alkyl, ($C_1$-$C_4$)haloalkyl, ($C_1$-$C_4$)alkoxyl, ($C_1$-$C_4$)haloalkoxyl, 2 to 4 membered heteroalkyl, cycloalkyl, heterocycloalkyl, aryl, or heteroaryl;

each $R^{b1}$, $R^{b2}$, and $R^{b3}$ is independently hydrogen, halo, ($C_1$-$C_4$)alkyl,—$S(O)_2R^d$,—$S(O)^2OR^d$, or ($C_1$-$C_4$)haloalkyl; or $R^{b2}$ and $R^{b3}$ are joined together to form an aryl or heteroaryl;

each $R^c$ and $R^d$ is independently hydrogen or ($C_1$-$C_4$) alkyl;

Ar is mono- or bi-cyclic aryl or heteroaryl, optionally substituted with one or more halo, ($C_1$-$C_4$)alkyl, ($C_1$-$C_4$)haloalkyl, ($C_1$-$C_4$)alkoxyl, ($C_1$-$C_4$)haloalkoxyl, or heteroaryl; and n=2, 3, 4, or 5, or, an effective dose of a compound of Formula (III)

(III)

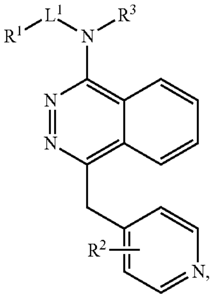

or a pharmaceutically acceptable salt thereof, wherein in Formula (III):

$L^1$ is a bond, $C_1$-$C_4$ alkylene, or 2 to 4-membered heteroalkylene;

$R^1$ is mono- or bi-cyclic cycloalkyl, heterocycloalkyl, aryl, alkylaryl, or heteroaryl, wherein the cycloalkyl, heterocycloalkyl, aryl, alkylaryl or heteroaryl is optionally substituted with one or more selected from halo, ($C_1$-$C_4$)alkyl, hydroxy ($C_1$-$C_4$)alkyl, ($C_1$-$C_4$) alkoxyl,—C(=O) ($C_1$-$C_4$)alkyl,—C(=O)N(R)$_2$, or —C(=NR) ($C_1$-$C_4$)alkyl, wherein the ($C_1$-$C_4$)alkyl is unsubstituted or substituted with heterocycloalkyl;

each R is independently H,—OH, ($C_1$-$C_4$)alkyl, or ($C_1$-$C_4$)alkoxyl, or two R together with the nitrogen atom to which it is bonded form a heterocycloalkyl, optionally further comprising an O atom in the heterocyclyl ring;

$R^2$ occurs 0, 1, or 2 times, and is ($C_1$-$C_4$)alkyl, ($C_1$-$C_4$) haloalkyl, or $SO_2N(R^4)_2$; and each $R^3$ and $R^4$ is independently H, or ($C_1$-$C_4$)alkyl, or, an effective dose of a compound of Formula (IV)

(IV)

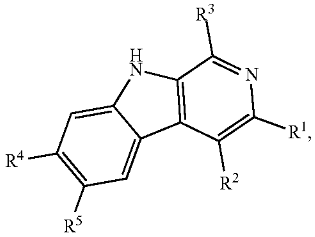

or a pharmaceutically acceptable salt thereof;

wherein in Formula (IV):

$R^1$ is hydrogen, ($C_1$-$C_4$)alkyl,—C(O) OH,—C(O)O—($C_1$-$C_4$)alkyl,—C(O) NHNHR$^6$,—C(O) NR$^6$—(($C_1$-$C_4$)alkylene)-NHR$^6$,—C(O) NR$^6$ ($C_1$-$C_4$)alkyl, or —C(O) NR$^6$-cycloalkylene-NHR$^6$;

$R^3$ is hydrogen or ($C_1$-$C_4$)alkyl;

each $R^2$, $R^4$, $R^5$ is independently hydrogen, halo, ($C_1$-$C_4$) alkyl,—C(O)O—($C_1$-$C_4$)alkyl, ($C_1$-$C_4$)alkoxyl, ($C_1$-$C_4$)haloalkyl, or CN; and each $R^6$ is hydrogen or ($C_1$-$C_4$)alkyl;

or, an effective dose of a compound of Formula (V)

(V)

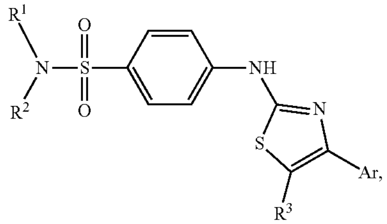

or a pharmaceutically acceptable salt thereof, wherein in Formula (V):

Ar is mono- or bi-cyclic aryl or heteroaryl, optionally substituted one or more with halo, ($C_1$-$C_4$)alkyl, ($C_1$-$C_4$)haloalkyl, CN,—$S(O)_2NH_2$, oxo,—$NH_2$, ($C_1$-$C_4$) alkoxyl, or —NHC(O) ($C_1$-$C_4$)alkyl;

each $R^1$ and $R^2$ is independently hydrogen, ($C_1$-$C_4$)alkyl, aryl or heteroaryl, wherein the aryl or heteroaryl is optionally substituted with halo or ($C_1$-$C_4$)alkyl, or $R^1$ and $R^2$ attached to nitrogen join together to form a 5 to 6 membered heterocycloalkyl; and $R^3$ is hydrogen, or hydroxy-($C_1$-$C_4$)alkyl, or, an effective dose of a compound of formula (VI)

(VI)

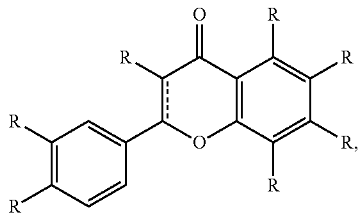

wherein in formula (VI), the indicated dashed double bond is optionally present, each R is independently selected from H, OH, or (C1-C4)alkoxyl, or O-glycosyl, provided that at least two R groups are non-hydrogen, or, an effective dose of a compound of formulas (VII)—(XV), or demethylated derivatives (phenolic analogs) thereof, or methyl ethers thereof, in the case of phenols or other alcohols:

(VII)

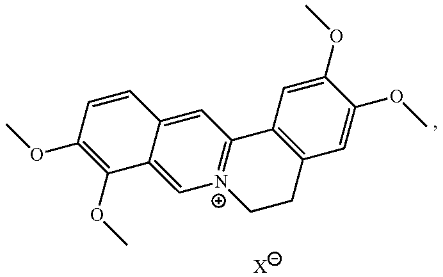

wherein in formula (VII), X is a pharmaceutically acceptable salt;

(VIII)

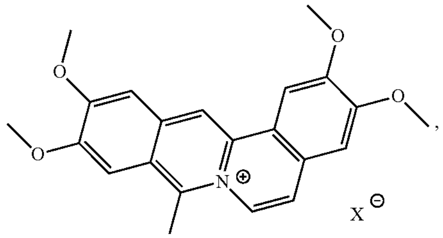

wherein in formula (VIII), X is a pharmaceutically acceptable salt;

(IX)

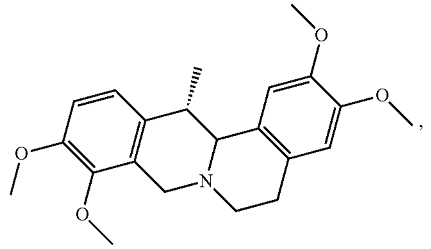

and including all pharmaceutically acceptable salt forms, (X)

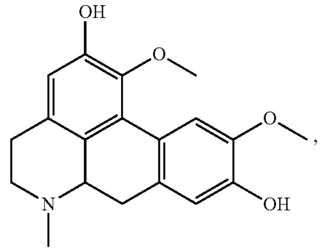

and including all pharmaceutically acceptable salt forms, (XI)

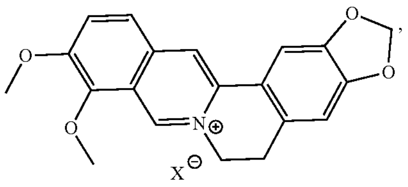

wherein in formula (XI), X is a pharmaceutically acceptable salt;

(XII)

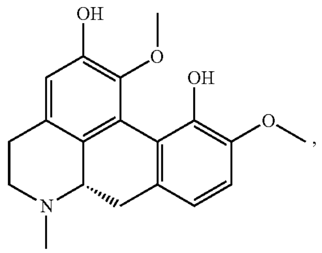

and including all pharmaceutically acceptable salt forms, (XIII)

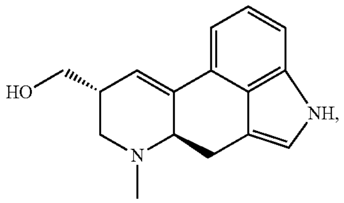

and including all pharmaceutically acceptable salt forms, (XIV)

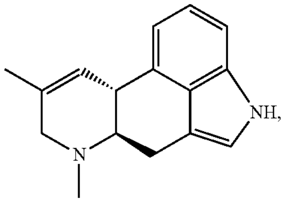

(XV)

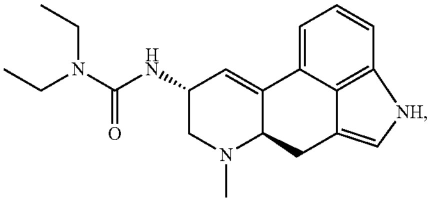

and including all pharmaceutically acceptable salt forms, or, an effective dose of a compound of formula (XVI)

(XVI)

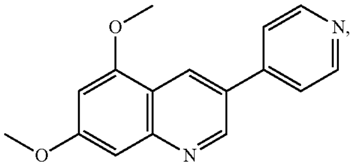

and including all pharmaceutically acceptable salt forms.

2. The method of claim 1, wherein compounds of Formula (I) to (XVI) inhibit protein ADP-ribosylation reactions, inhibit NAD cleavage by protein deacetylases or glycohydrolases, or increase NAD synthesis.

3. The method of claim 1 wherein the patient is afflicted with a metabolic disorder, aging, a degenerative disease, a neurodegenerative disease, neuronal degeneration associated with multiple sclerosis, hearing loss, retinal damage or multiple sclerosis, brain or cardiac ischemia, kidney failure, kidney disease, traumatic brain injury, or an axonopathy.

4. The method of claim 1, wherein the patient is afflicted with a prion disease, Parkinson's disease or other synucleinopathy, Alzheimer's disease, amyotrophic lateral sclerosis, a tauopathy or diabetes mellitus.

5. The method of claim 1, wherein the compound of Formula (I) is any one of these structures, including their pharmaceutically acceptable salt forms:

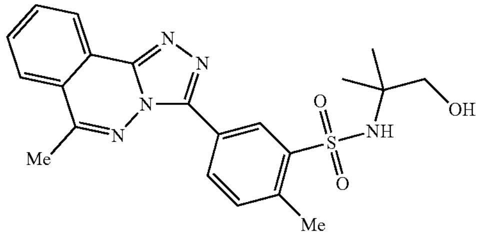

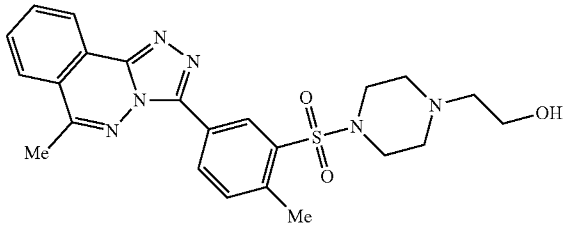

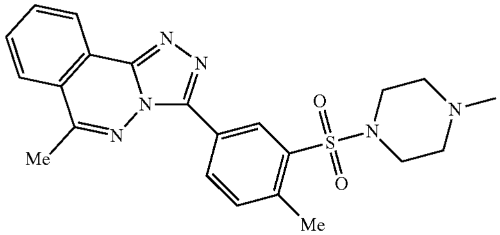

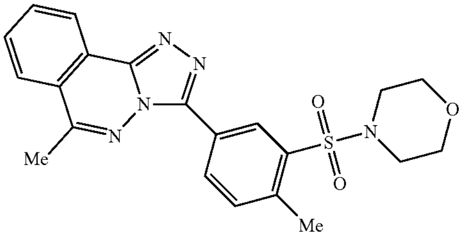

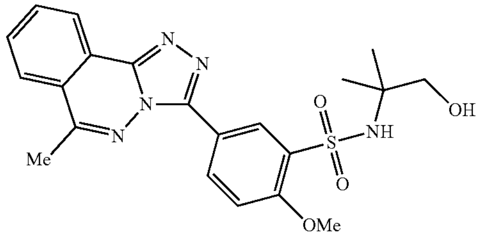

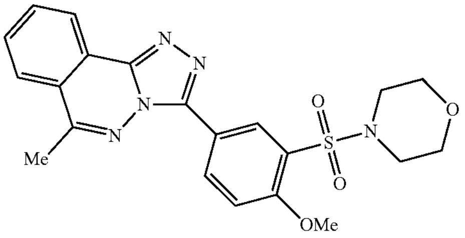

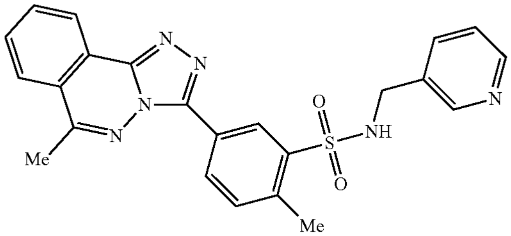

-continued
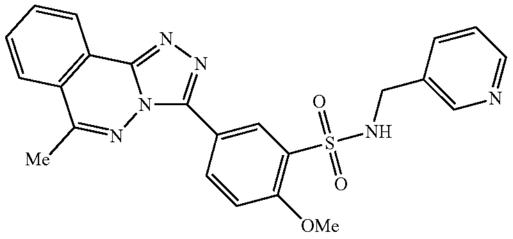
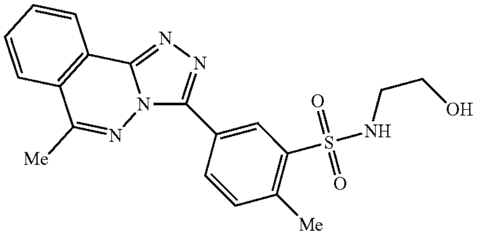
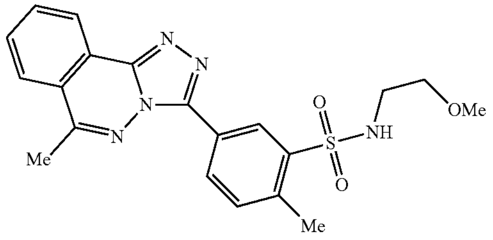
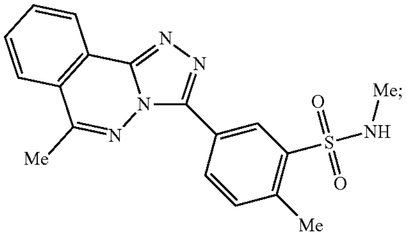
or, the compound of Formula (II) is any one these structures, including their pharmaceutically acceptable salt forms:
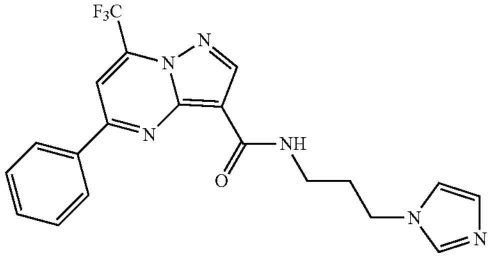
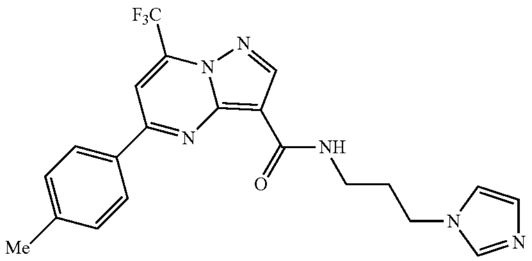
-continued
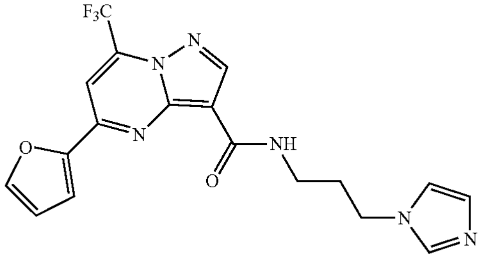
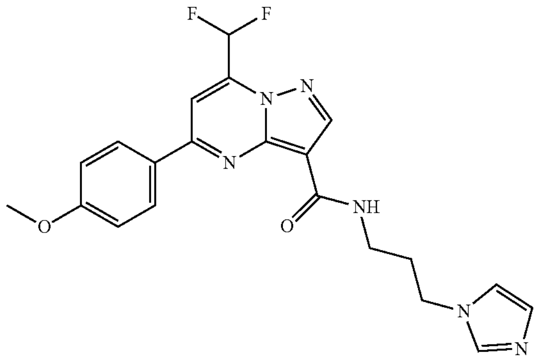
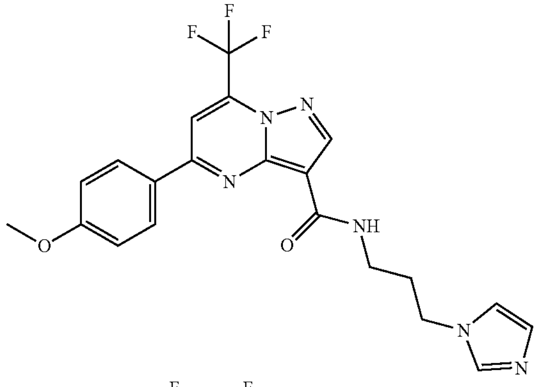
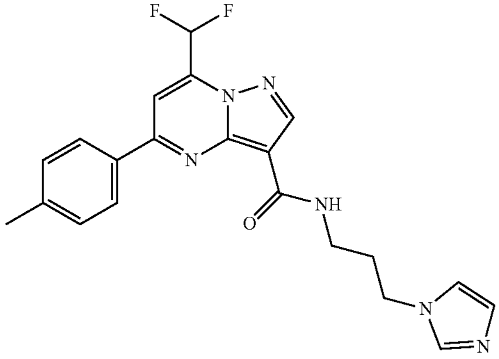
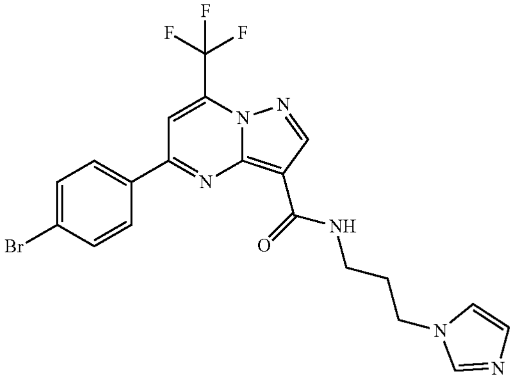

-continued
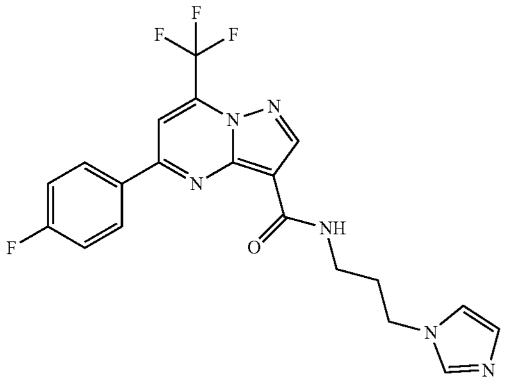
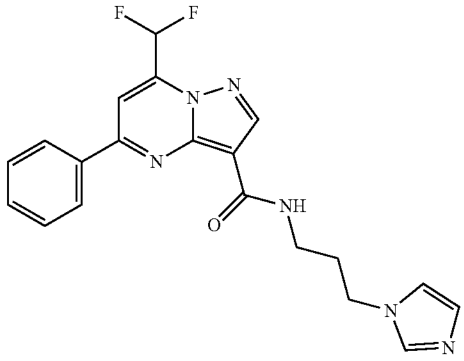
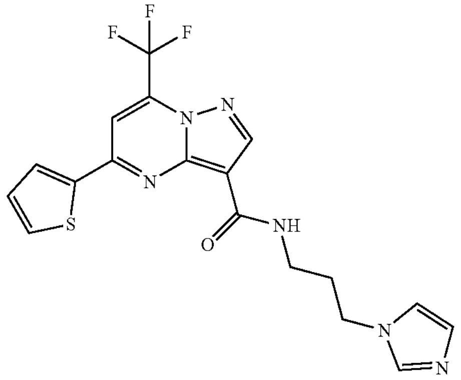
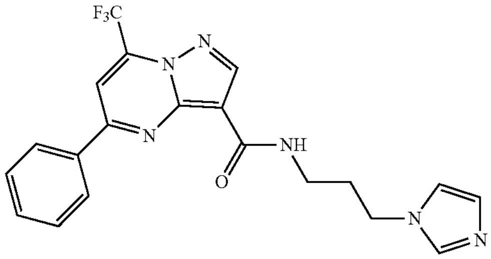
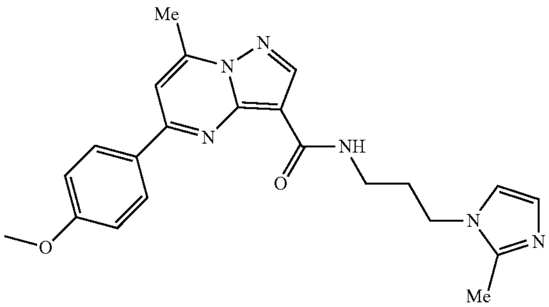
-continued
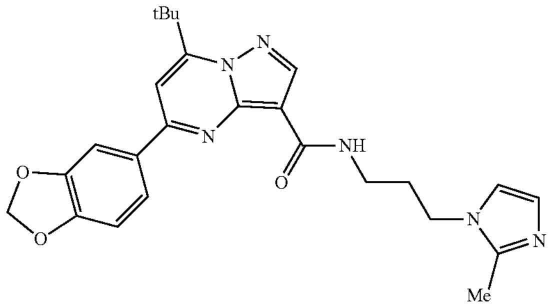
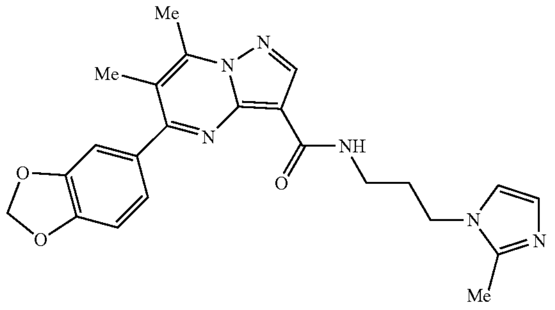
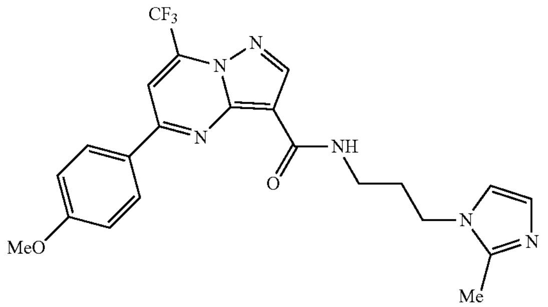
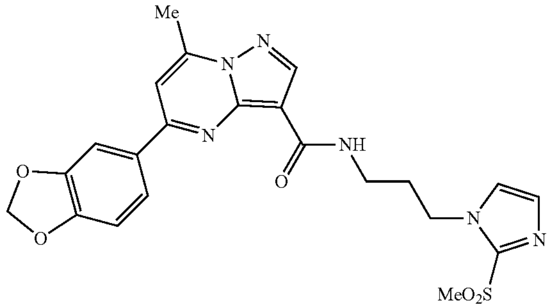
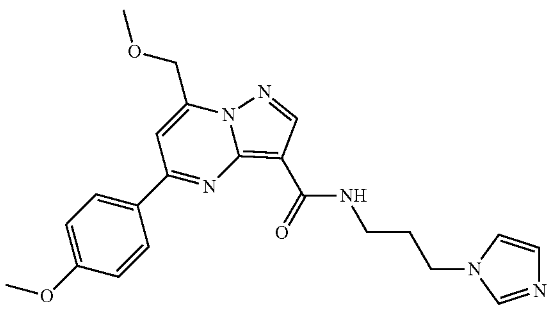

-continued
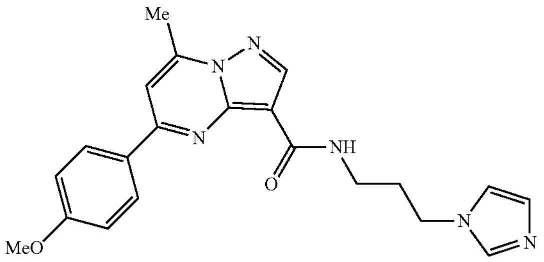
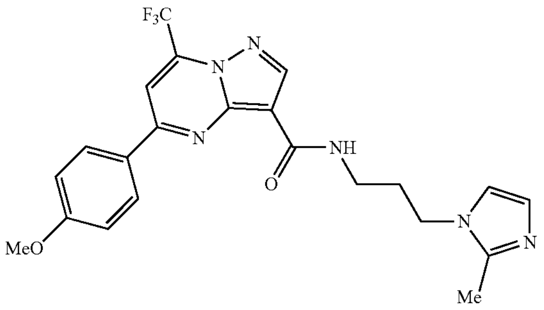
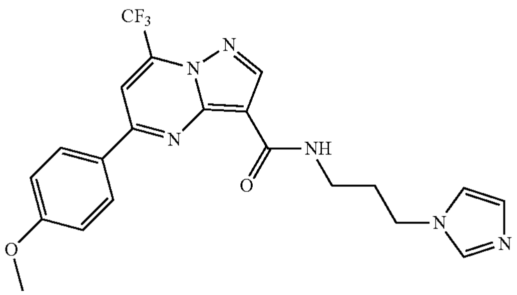
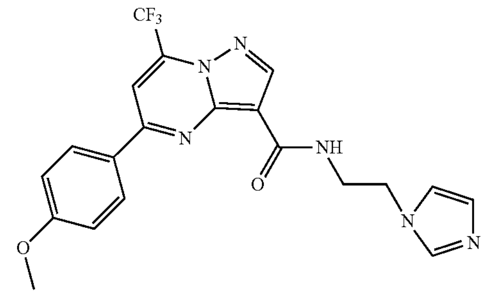
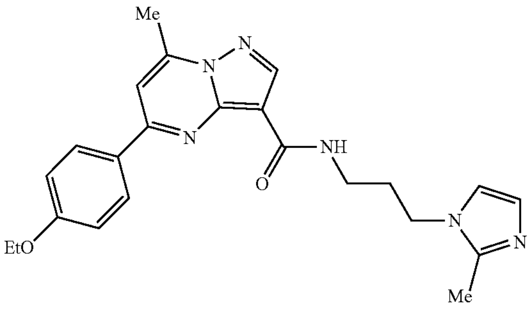
-continued
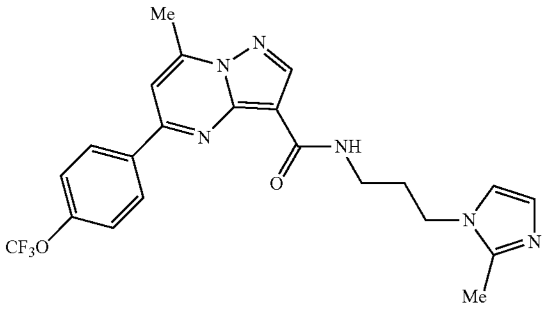
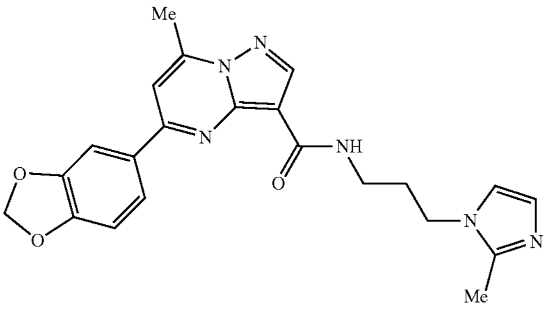
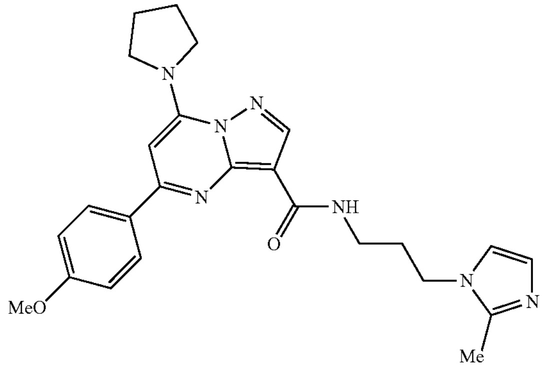
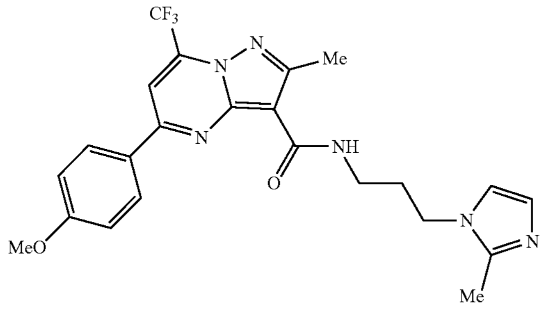
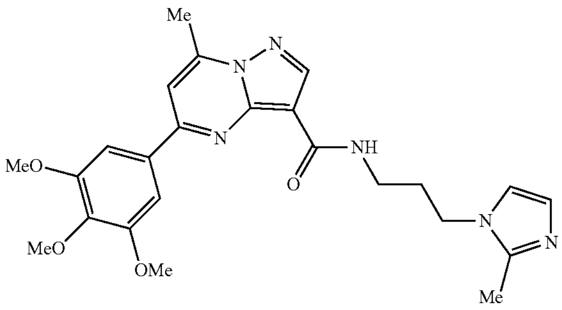

-continued
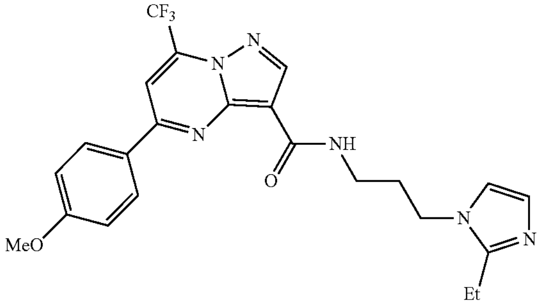
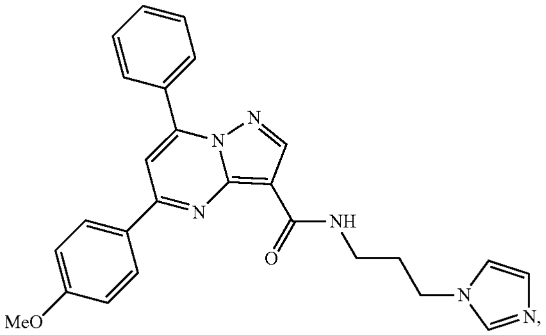
,
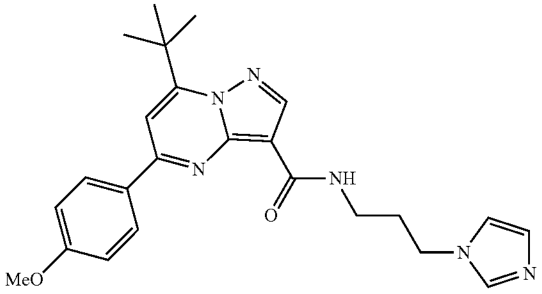
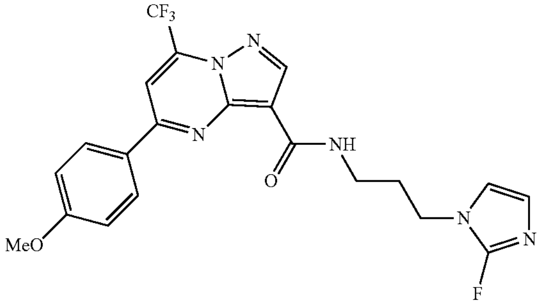
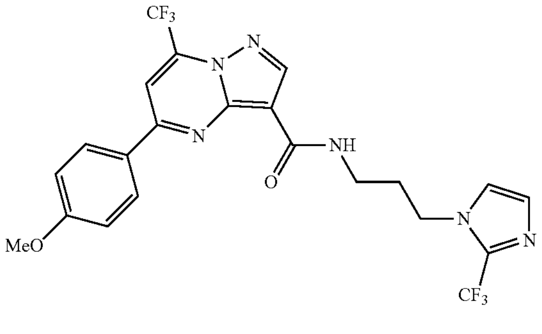
-continued
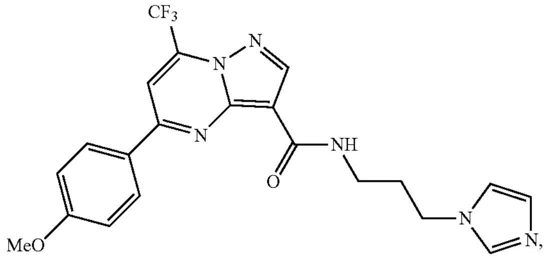
,
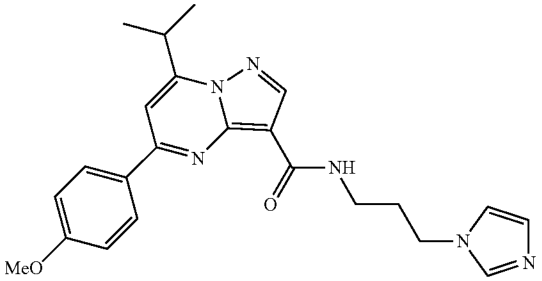
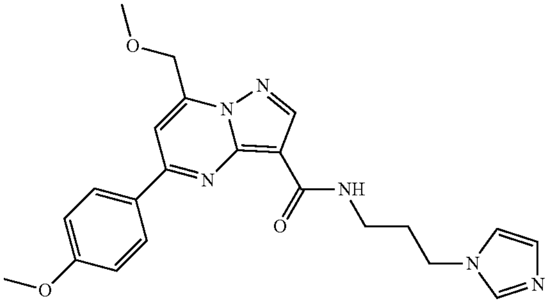
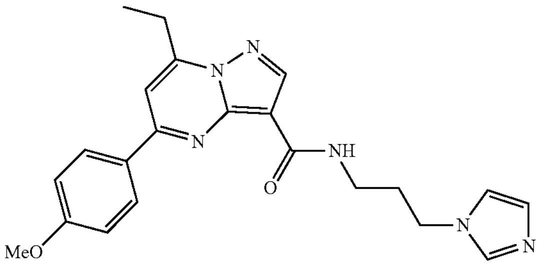
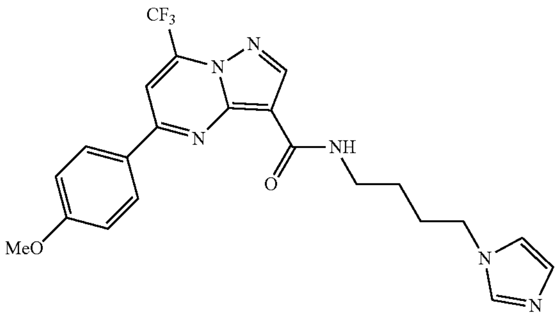
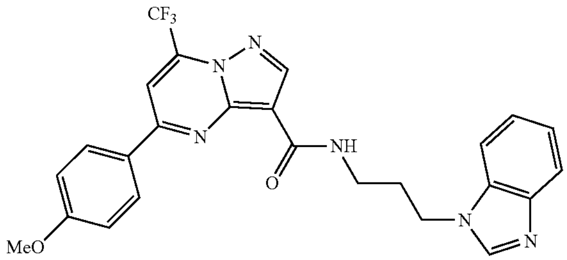

-continued
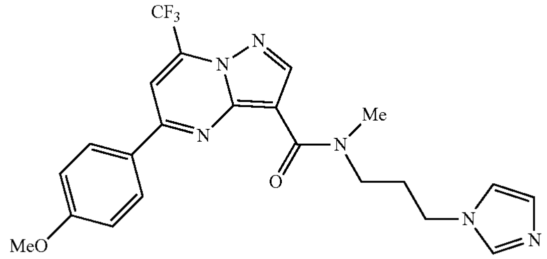
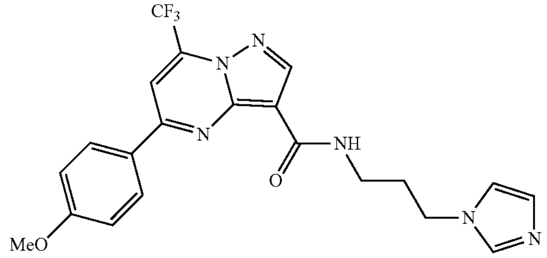
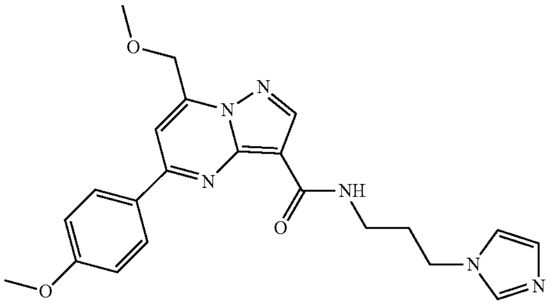
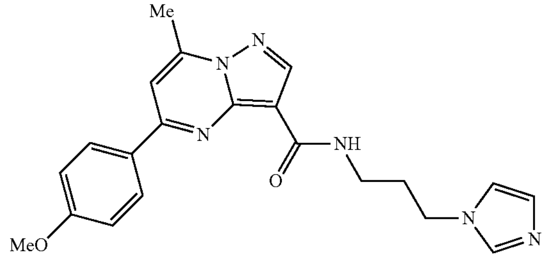
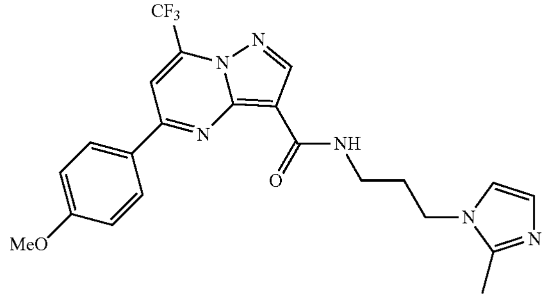
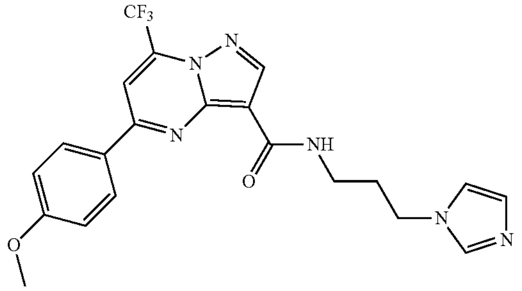
-continued
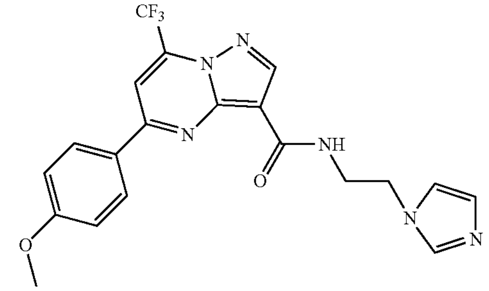
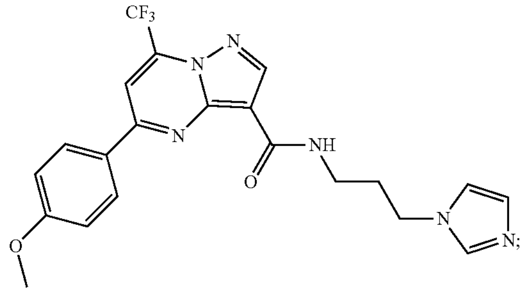 [SMILES: COc1ccc(-c2cc(C(F)(F)F)n3ncc(C(=O)NCCCn4ccnc4)c3n2)cc1]
or, the compound of Formula (III) is any one of these structures, including their pharmaceutically acceptable salt forms:
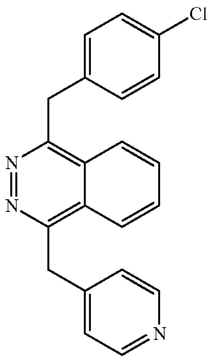
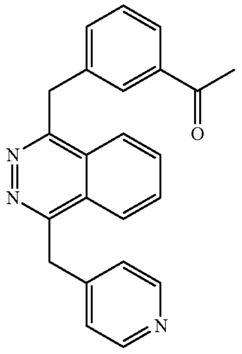
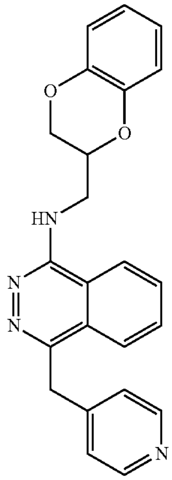
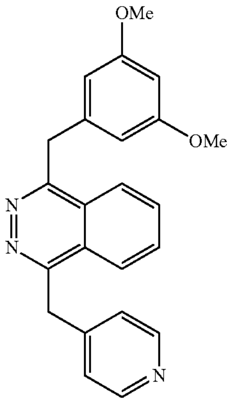

-continued
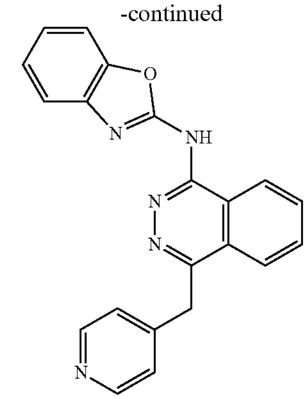
,
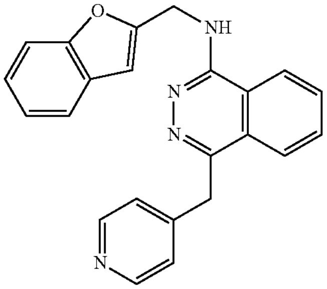
,
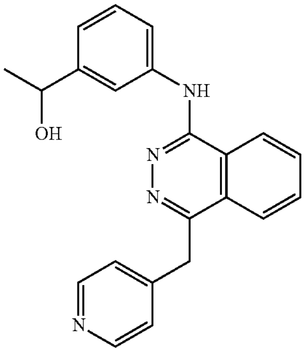
,
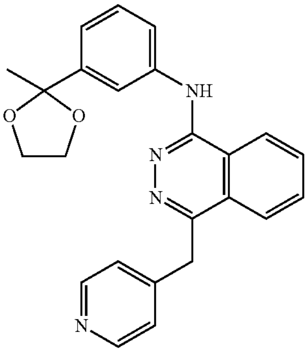
,
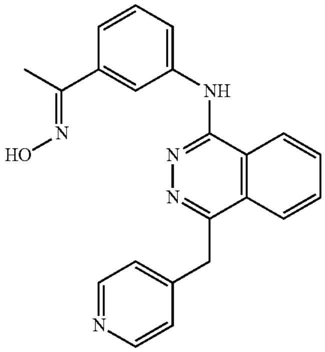
,
-continued
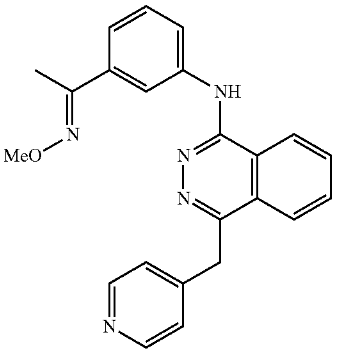
,
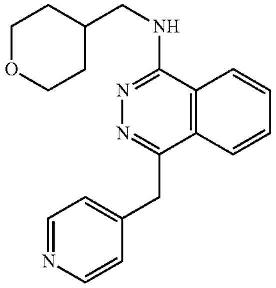
,
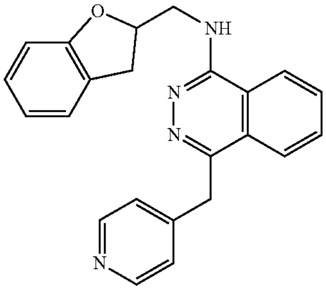
,
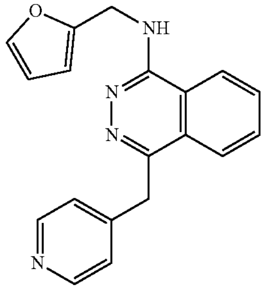
,
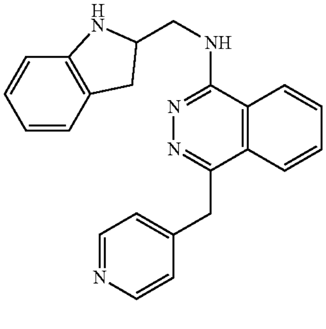
, -continued
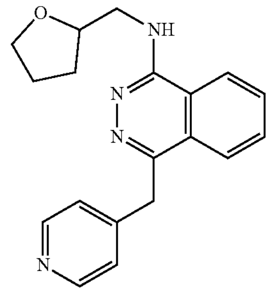
,
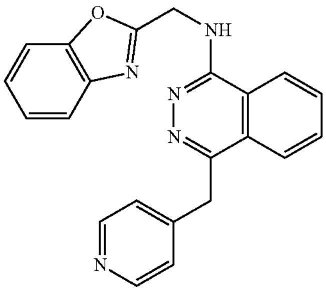
,
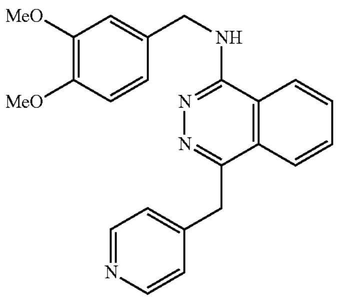
,
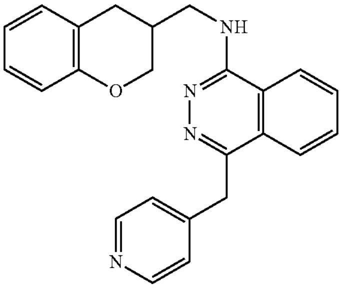
,
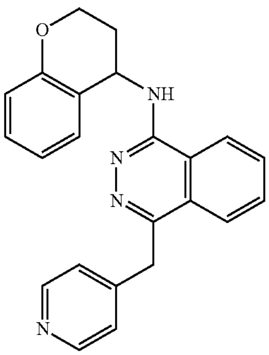
,
-continued
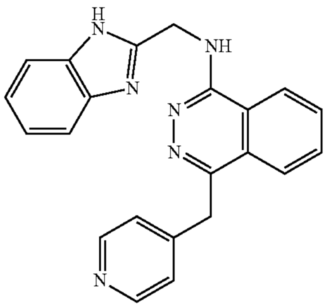
,
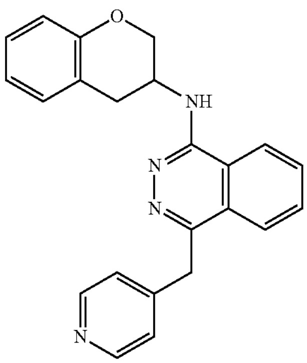
,
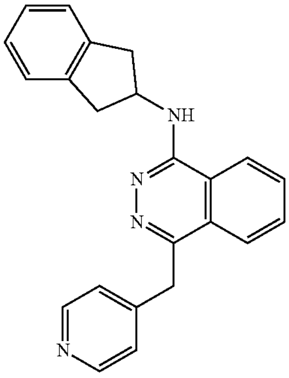
,
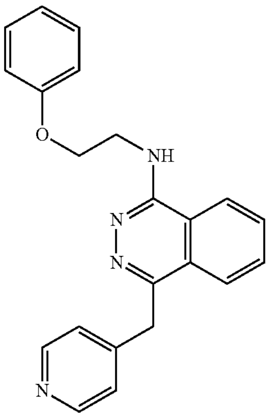
, -continued
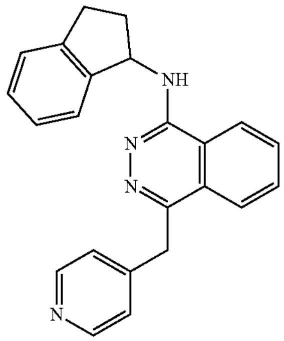
;
or, the compound of Formula (IV) is any one of these structures, including their pharmaceutically acceptable salt forms:
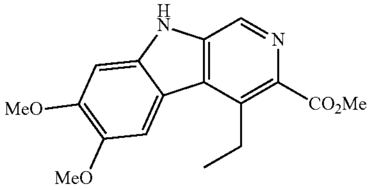
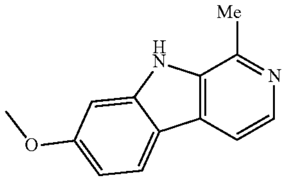
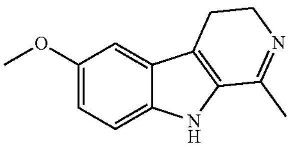
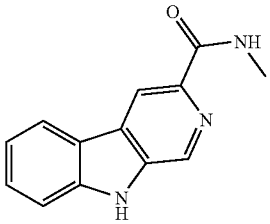
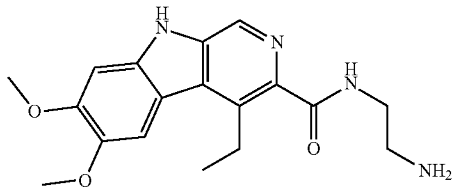
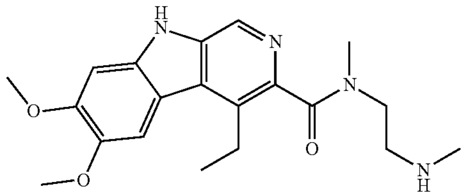
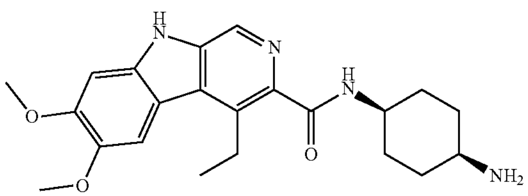
-continued
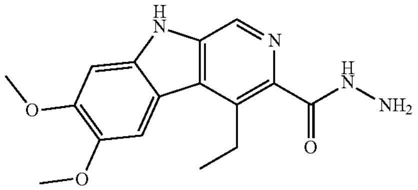
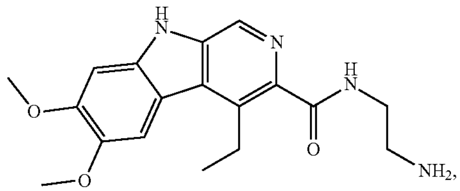
,
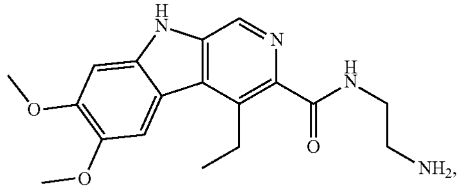
,
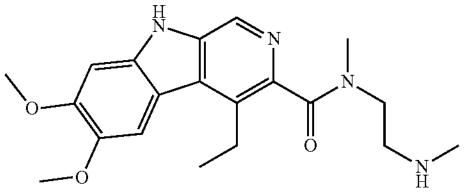
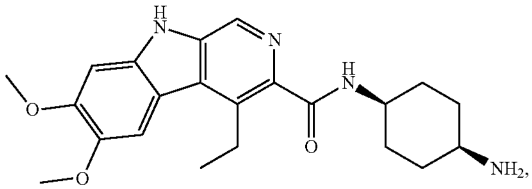
,
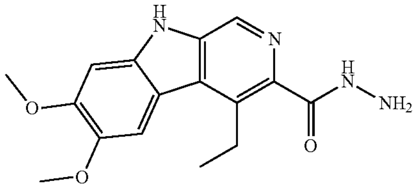
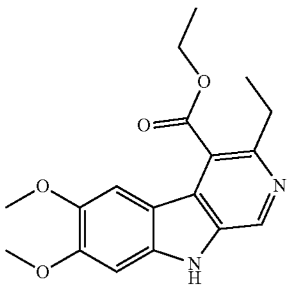
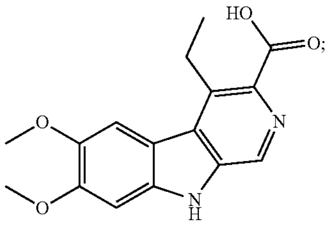
;

or, the compound of Formula (V) is any one of:
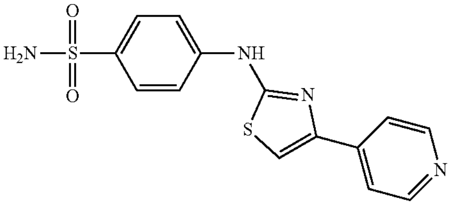
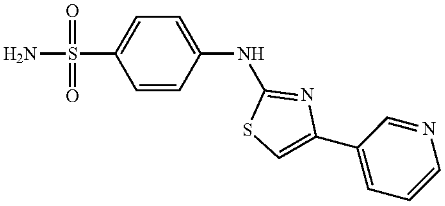
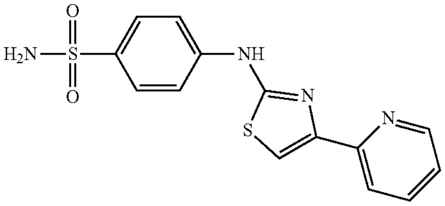
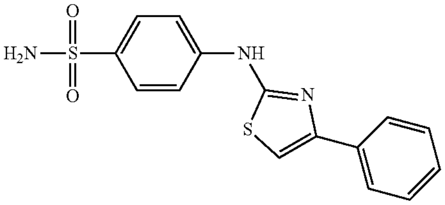
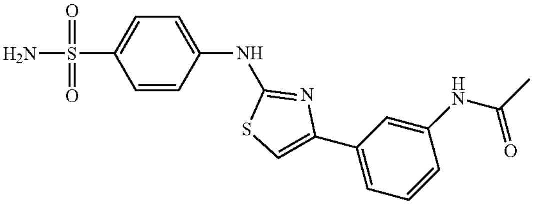
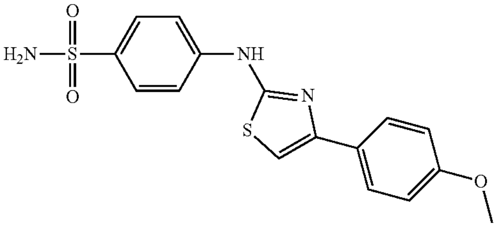
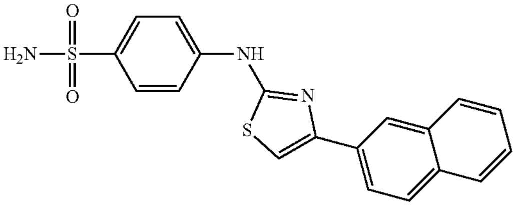
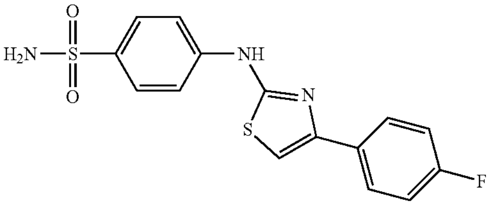
-continued
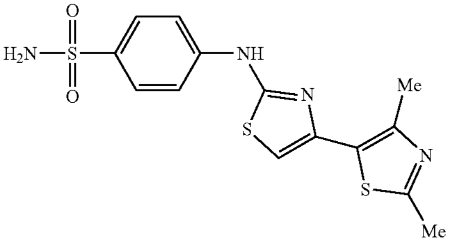
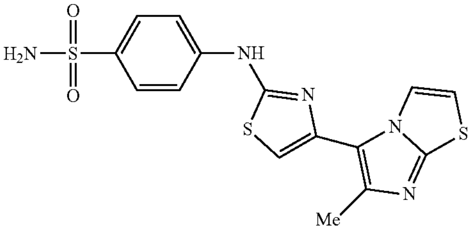
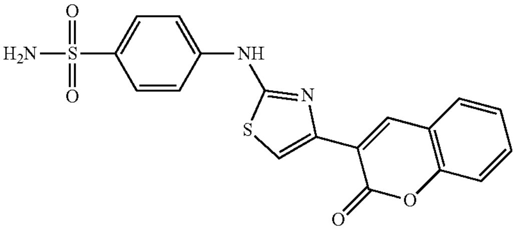
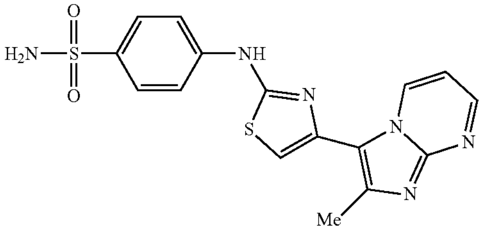
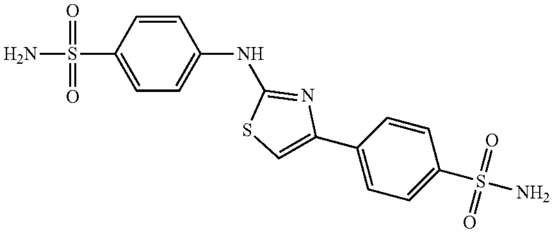
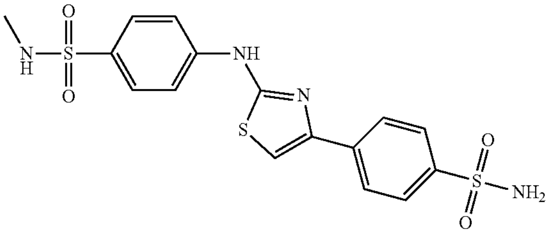
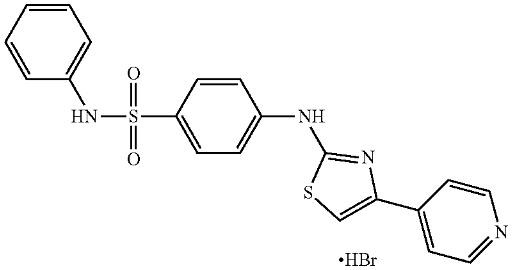
•HBr -continued
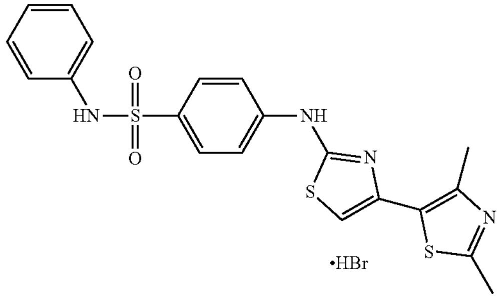
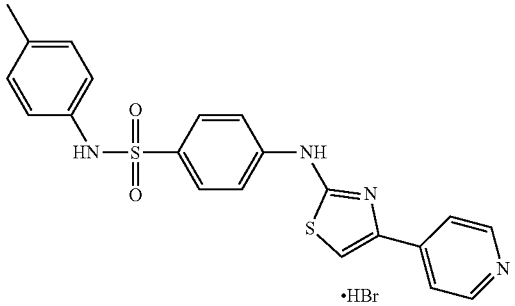
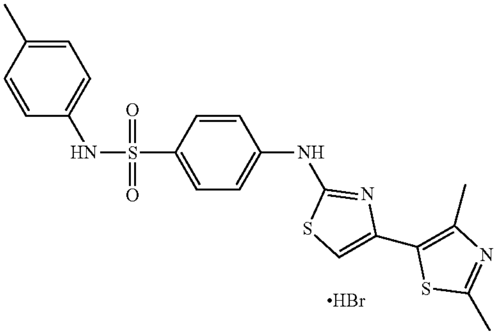
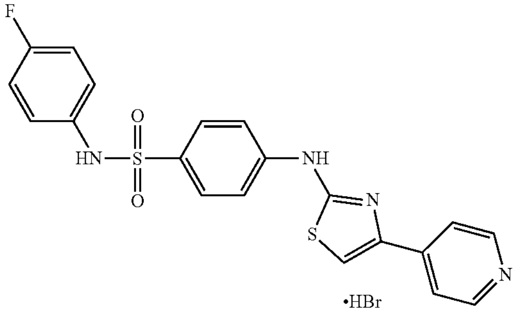
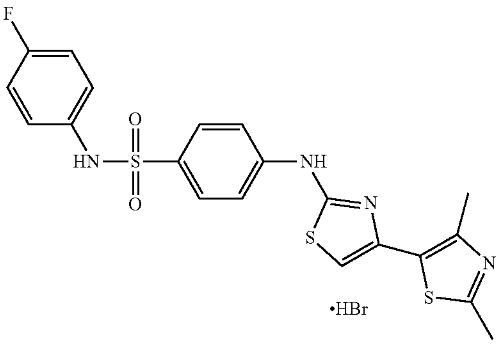
-continued
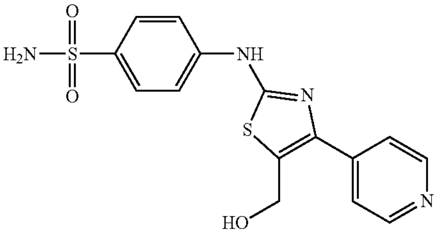
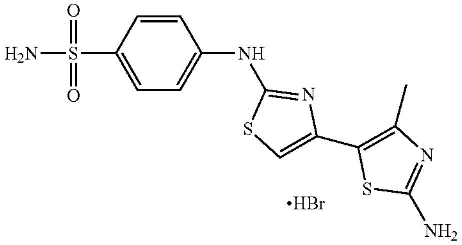
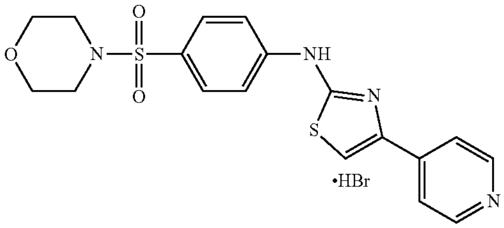
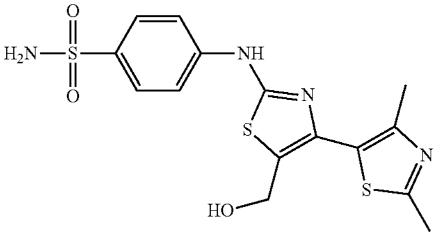
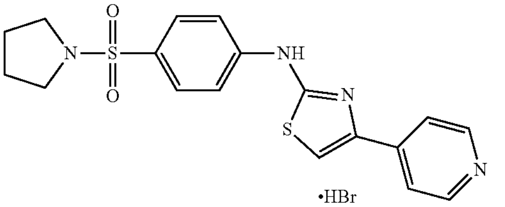
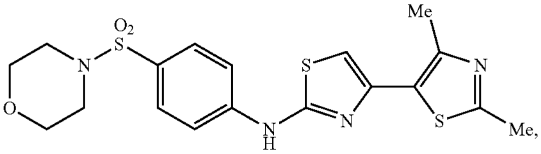
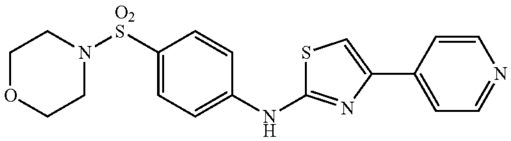
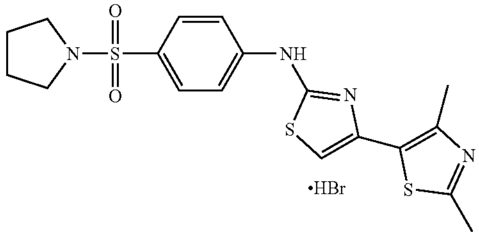

-continued
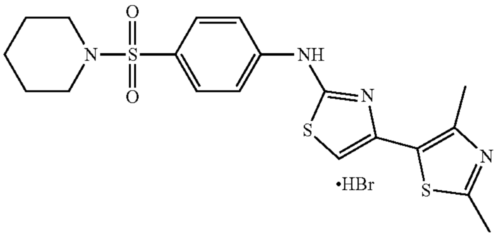
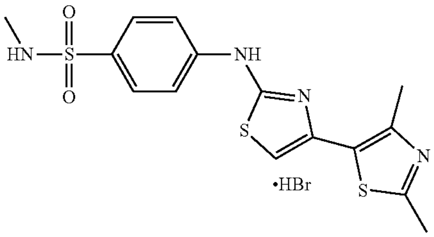
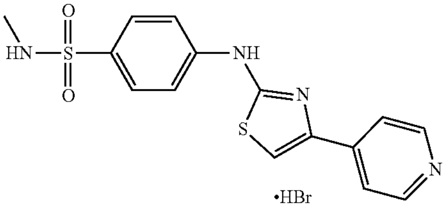
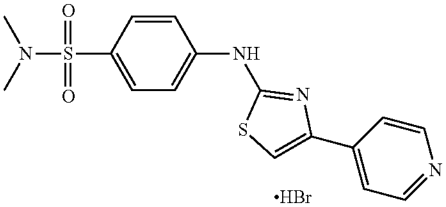
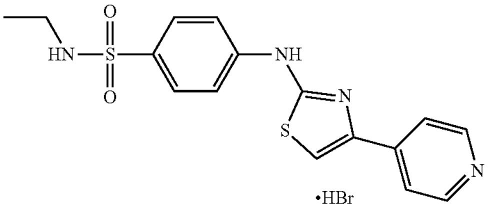
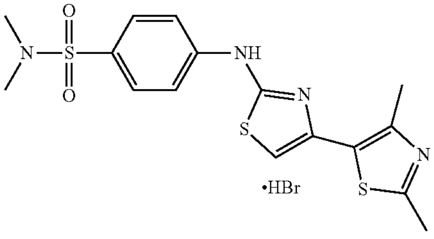
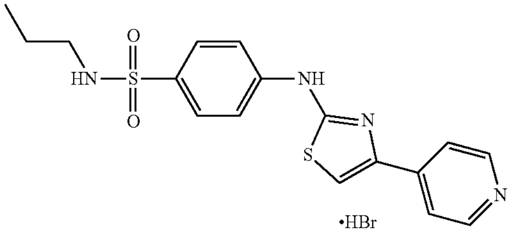
-continued
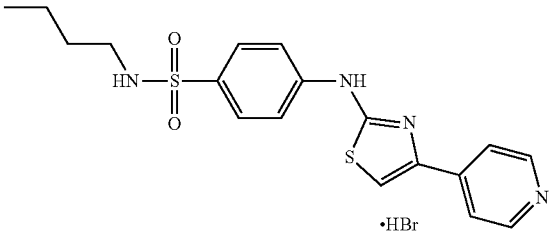
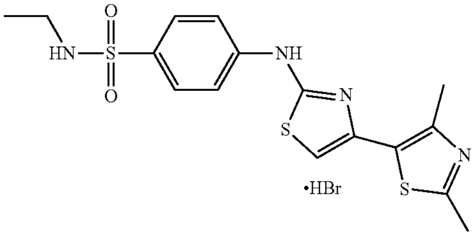
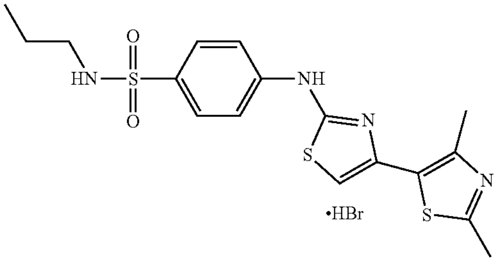
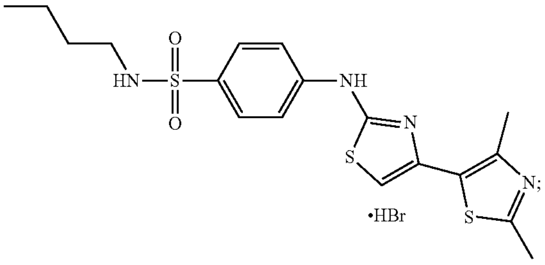
or, the compound of formula (VI) is any one of:
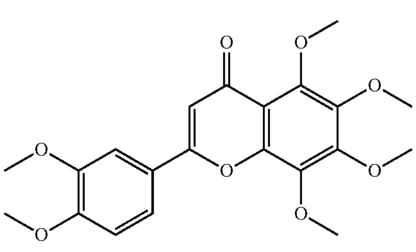
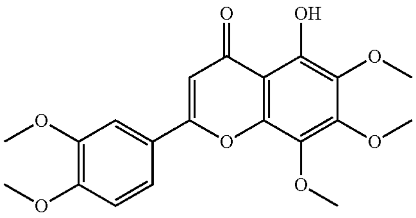

-continued
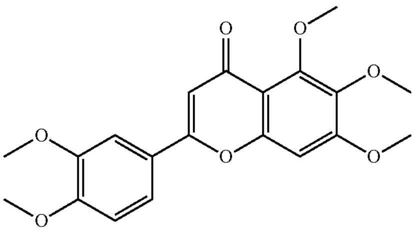
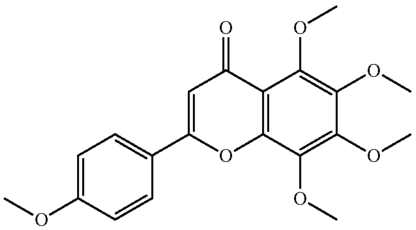
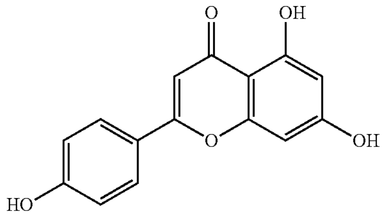
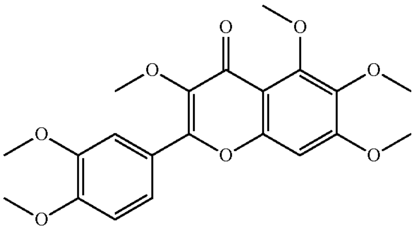
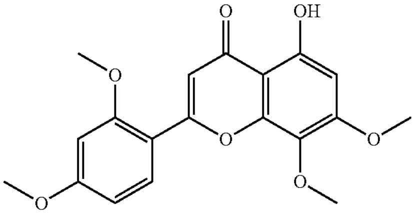
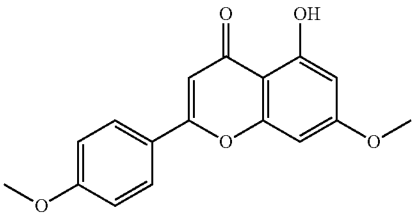
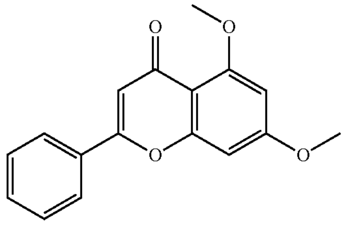
-continued
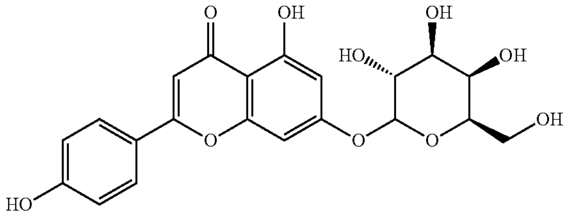
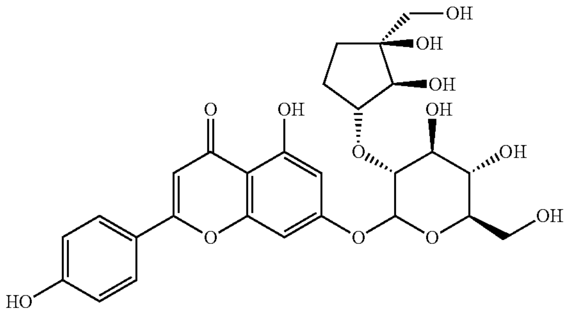
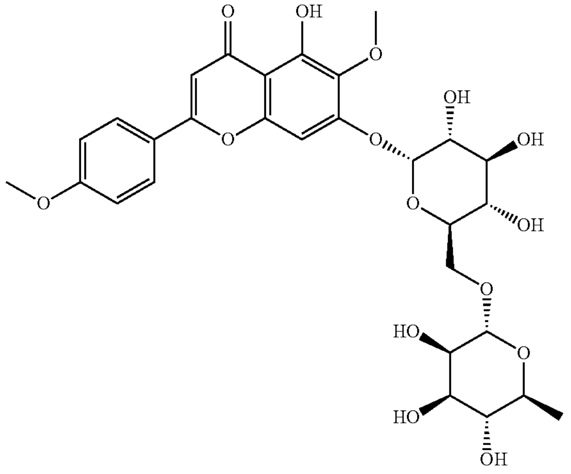
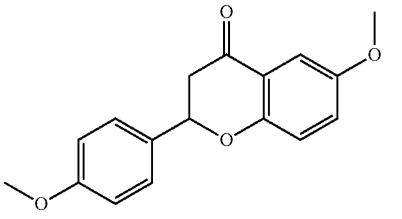
or, the compound of formulas (VII)—(XVI) is any one of these structures, including their pharmaceutically acceptable salt forms:
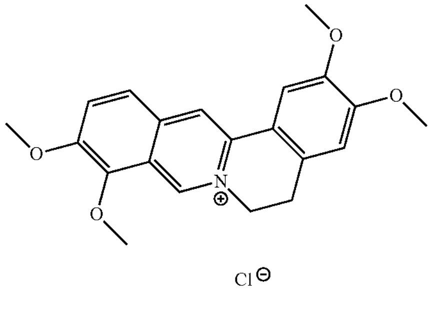

-continued
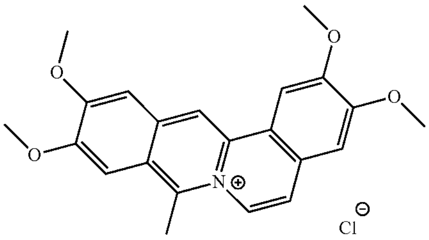
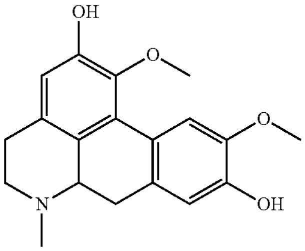
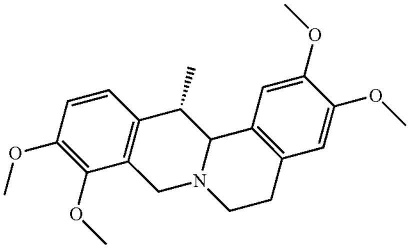
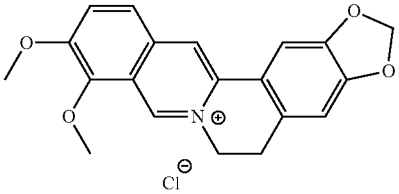
-continued
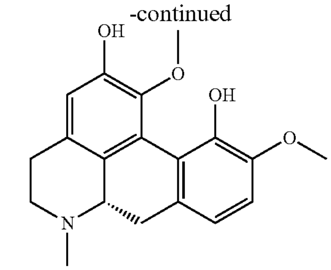
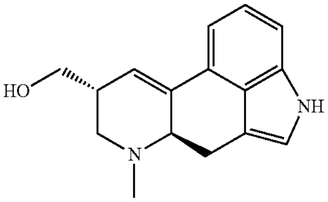
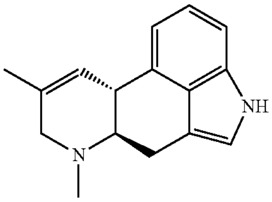
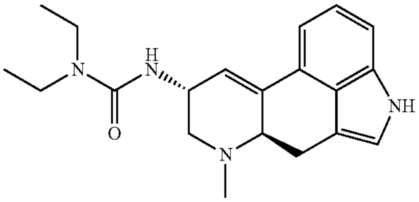
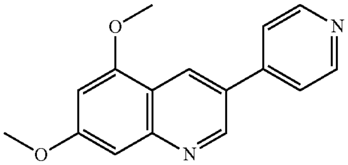
.
* * * * *